United States Patent
Ootsuki et al.

(10) Patent No.: US 8,404,316 B2
(45) Date of Patent: Mar. 26, 2013

(54) POLYMERIZABLE LIQUID CRYSTAL COMPOUND AND ITS POLYMER

(75) Inventors: Daisuke Ootsuki, Chiba (JP); Junichi Inagaki, Chiba (JP)

(73) Assignees: JNC Corporation, Tokyo (JP); JNC Petrochemical Corporation, Tokyo (JP)

( * ) Notice: Subject to any disclaimer, the term of this patent is extended or adjusted under 35 U.S.C. 154(b) by 128 days.

(21) Appl. No.: 12/894,543

(22) Filed: Sep. 30, 2010

(65) Prior Publication Data

US 2011/0086185 A1 Apr. 14, 2011

(30) Foreign Application Priority Data

Oct. 13, 2009 (JP) ................... 2009-236113
May 20, 2010 (JP) ................... 2010-116178
Sep. 6, 2010 (JP) ................... 2010-198817

(51) Int. Cl.
*C09K 19/34* (2006.01)
*C07D 303/06* (2006.01)
*C07D 303/10* (2006.01)

(52) U.S. Cl. .................... 428/1.1; 252/299.61; 549/546; 549/547

(58) Field of Classification Search ............. 252/299.66, 252/299.67, 299.61, 299.62; 549/510, 512, 549/547, 557, 560, 546; 428/1.1, 1.3
See application file for complete search history.

(56) References Cited

U.S. PATENT DOCUMENTS 5,773,178 A 6/1998 Shiota et al.

FOREIGN PATENT DOCUMENTS

| JP | 07-017910 | 1/1995 |
| JP | 09-316032 | 12/1997 |
| JP | 2008-110948 | 5/2008 |
| JP | 2008214449 A * | 9/2008 |
| JP | 2008-239567 | 10/2008 |
| JP | 2008-239569 | 10/2008 |
| JP | 2010-083781 | 4/2010 |

OTHER PUBLICATIONS

CAPLUS 2008: 1119429.*
Mallon et al., Synthesis and Charaterization of Novel Epoxy Monomers and Liquid Crystal Thermosets, Journal of Polymer Science: Part A: Polymer Chemistry, 1993, vol. 31, pp. 2249-2260.
Jahromi et al., Synthesis and Photoinitiated polymerization of liquid crystalline diepoxides, Polymer,1994, vol. 35, No. 3, pp. 622-629.

* cited by examiner

*Primary Examiner* — Shean C Wu
(74) *Attorney, Agent, or Firm* — J.C. Patents

(57) ABSTRACT

A polymerizable liquid crystal compound represented by formula (1):

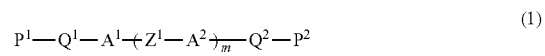

wherein $A^1$ and $A^2$ are each a cyclic-structure group; $Z^1$ is a bonding group; m is an integer from 0 to 5; $P^1$ is a polymerizable group represented by formula (2-1); $Q^1$ is alkylene having 1 to 20 carbons; $P^2$ is a polymerizable group represented by any one of formula (2-1) to formula (2-4), hydrogen, fluorine, chlorine, —CN, —CF$_3$, —OCF$_3$, alkyl having 1 to 20 carbons or alkoxy having 1 to 20 carbons; $Q^2$ is a group defined in $Q^1$ when $P^2$ is a polymerizable group and, and $Q^2$ is a single bond when $P^2$ is not a polymerizable group; and in formula (2-2) to formula (2-4), Ra is hydrogen, halogen or alkyl having 1 to 5 carbons.

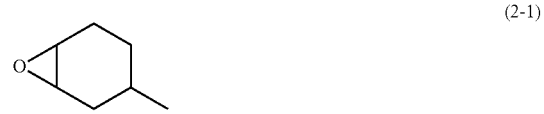

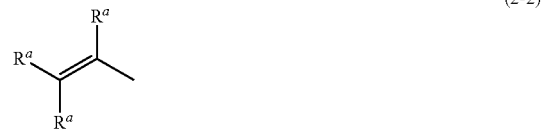

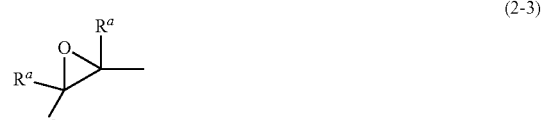

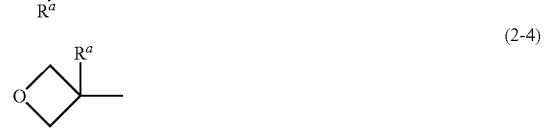

14 Claims, No Drawings

POLYMERIZABLE LIQUID CRYSTAL COMPOUND AND ITS POLYMER

BACKGROUND OF THE INVENTION

1. Field of the Invention

The invention relates to a liquid crystal compound having a cyclohexene oxide moiety as a polymerizable group, its polymer and a film having optical anisotropy.

2. Related Art

A polymerizable liquid crystal compound has recently been utilized for an optically anisotropic substance such as a polarizing plate and an optical retardation plate. This is because the compound exhibits optical anisotropy in the liquid crystal state and then the liquid crystal molecules in this state are fixed by polymerization. The kinds of optical characteristics required for a polymer having optical anisotropy depends on a purpose for use, and a compound having characteristics that suits the purpose is necessary. In the compound used for such a purpose, characteristics regarding its polymer are important in addition to the characteristic of optical anisotropy. Characteristics required for the polymerizable liquid crystal compound, its composition and their polymer include compatibility, solubility, clearing points, applicability, the rate of polymerization, transparency, melting points, the degree of crystallinity, glass transition temperature, shrinkage, water permeability, water absorptivity, mechanical strength, chemical resistance and thermal resistance.

A compound having an acryloyloxy group as a polymerizable group among polymerizable liquid crystal compounds is used for such purposes (patent documents Nos. 1 and 2). The acrylate has a high reactivity and the polymer derived from it has a high transparency. However, it is necessary to carry out the reaction in an atmosphere of an inert gas and to increase energy of ultraviolet irradiation, because the mode of polymerization is radical polymerization. Thus, an improvement of workability on curing in air and also of characteristics such as heat resistance, shrinkage, adhesive properties, adhesion and mechanical strength is required. Furthermore, a polymerizable liquid crystal compound (or its composition) is diluted with an organic solvent for the purpose of adjusting applicability and can be used as ink. The ink in which the viscosity, the leveling properties and so forth are adjusted is prepared by dissolution of the polymerizable liquid crystal compound (or its composition), a photopolymerization initiator, a surfactant and so forth in an organic solvent in the case where a film having optical anisotropy is produced from the polymerizable liquid crystal compound (or its composition). The ink is applied to a transparent substrate film that is aligned, the solvent is dried, and then the polymerizable liquid crystal compound (or its composition) is oriented. Next, the compound is polymerized with ultraviolet irradiation or heat and thus the oriented state is fixed. An organic solvent such as propylene glycol monoethyl ether acetate (PGMEA) is desirable for a solvent used in this procedure in view of environmental load and safety (mutagenicity and toxicity). However, the compounds disclosed in non-patent documents Nos. 1 and 2 have not a large solubility in such a solvent for preparing the ink with a suitable concentration. Incidentally, although compounds similar to the compound of the invention are disclosed in claims of the patent documents Nos. 3 to 6, there are no specific descriptions of the compound of the invention and its effect in any of these documents.

Conventional compounds are disclosed in the following patent documents: No. 1, JP H07-017910 A (1995); No. 2, JP H09-316032 A (1997); No. 3, JP 2008-239567 A; No. 4, JP 2008-110948 A; No. 5, JP 2008-239569 A; and No. 6, JP 2010-083781 A.

Conventional compounds are also disclosed in the following non-patent documents: No. 1, Polymer Chemistry, 1993, 31(9), 2249-60 and No. 2, Polymer, 1994, 35(3), 622-9.

SUMMARY OF THE INVENTION

The invention concerns a polymerizable liquid crystal compound shown in the following item [1], and concerns a composition including the compound, a film formed from the composition and a liquid crystal display device containing the film.

[1] A polymerizable liquid crystal compound represented by formula (1):

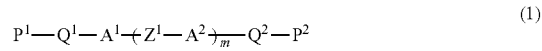

wherein $A^1$ and $A^2$ are each independently 1,4-cyclohexylene, 1,4-phenylene, pyridine-2,5-diyl, pyrimidine-2,5-diyl, naphthalene-2,6-diyl, tetrahydronaphthalene-2,6-diyl, 1,3-dioxane-2,5-diyl or fluorene-2,7-diyl, and in the 1,4-phenylene and fluorene-2,7-diyl, arbitrary hydrogen may be replaced by fluorine, chlorine, cyano, methyl, ethyl, methoxy, hydroxy, formyl, acetoxy, acetyl, trifluoroacetyl, difluoromethyl or trifluoromethyl;

$Z^1$ is a single bond, —O—, —COO—, —OCO—, —CH=CH—COO—, —OCO—CH=CH—, —OCO—CH$_2$CH$_2$—, —CH$_2$CH$_2$—COO—, —C≡C—COO—, —OCO—C≡C—, —CH$_2$O—, —OCH$_2$—, —CF$_2$O—, —OCF$_2$—, —CONH—, —NHCO—, —(CH$_2$)$_4$—, —CH$_2$CH$_2$—, —CF$_2$CF$_2$—, —CH=CH—, —CF=CF— or —C≡C—;

m is an integer from 0 to 5, where arbitrary two of $A^2$ may be the same rings or different rings and arbitrary two of $Z^1$ may be the same bonding groups or different bonding groups, when m is 2 or more;

$P^1$ is a polymerizable group represented by formula (2-1);

$Q^1$ is alkylene having 1 to 20 carbons, and in the alkylene arbitrary hydrogen may be replaced by fluorine and arbitrary —CH$_2$— may be replaced by —O—, —COO—, —OCO—, —CH=CH— or —C≡C—;

$P^2$ is a polymerizable group represented by any one of formula (2-1) to formula (2-4), hydrogen, fluorine, chlorine, cyano, trifluoromethyl, trifluoromethoxy, alkyl having 1 to 20 carbons or alkoxy having 1 to 20 carbons;

$Q^2$ is a group defined in $Q^1$ when $P^2$ is a polymerizable group and $Q^2$ is a single bond when $P^2$ is not a polymerizable group:

-continued

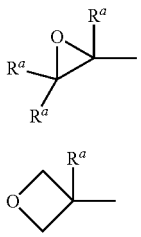
(2-3)

(2-4)

wherein $R^a$ is independently hydrogen, halogen or alkyl having 1 to 5 carbons.

DETAILED DESCRIPTION OF THE INVENTION

The terms used in the invention will be explained first. The meaning of the term "liquid crystal" or "liquid crystalline" in this specification is not limited to characteristics having a liquid crystal phase, and includes also characteristics in which a compound can be used as a component of a liquid crystal composition when mixed with another liquid crystal compound, even though the compound itself does not have a liquid crystal phase. A polymerizable liquid crystal compound represented by formula (1) may be abbreviated to "the compound (1)", and the same applies to a compound represented by another formula. The term "arbitrary" used for the explanation of the symbols in chemical formulas means that "not only the position of an element (or a functional group) but also its number can be selected without restriction". For example, the expression "arbitrary A may be replaced by B, C or D," means that one A may be replaced by any one of B, C and D, and that arbitrary two of A may be replaced by two of B, C or D, and also that arbitrary two of A may be replaced by B and C, B and D, or C and D. In the cases where arbitrary —$CH_2$— may be replaced by —O—, a replacement that forms a bonding group —O—O— is excluded. Incidentally, the unit, gram (g), in Examples means a value of gram displayed in a digital analytical balance. Values of percentage by weight or parts by weight are based on values thus measured.

One of the advantages of the invention is to provide a polymerizable liquid crystal compound that has a liquid crystal phase with a wide temperature range centering at room temperature, has an excellent compatibility with another polymerizable liquid crystal compound, has an excellent solubility in an organic solvent and is polymerizable even in air by heat or light. Another advantage is to provide a polymer that has optical anisotropy and has a plurality of excellent characteristics among characteristics such as transparency, mechanical strength, shrinkage, water permeability, water absorptivity, melting points, glass transition temperature, clearing points, chemical resistance and thermal resistance. A further advantage is to provide a liquid crystal display device containing the polymer having optical anisotropy.

The polymerizable liquid crystal compound of the invention satisfied a plurality of characteristics among characteristics such as a liquid crystal phase with a wide temperature range centering at room temperature, an excellent compatibility with another polymerizable liquid crystal compound, an excellent solubility in organic solvent, polymerizability at room temperature, polymerizability even in air, polymerizability by heat, a high polymerizability, chemical stability and colorlessness. The solubility in a solvent that was highly safe was excellent when used especially for ink. A polymer formed from this polymerizable liquid crystal compound as a starting material satisfied a plurality of characteristics among characteristics such as a suitable optical anisotropy, a high peel adhesion to a supporting substrate, a sufficient hardness, transparent colorlessness, a high heat resistance, a high weather resistance, a low photoelasticity. Thus, the polymer of the invention can be utilized, for example, for elements of a liquid crystal display device, such as an optical retardation plate, a polarizer, an antireflection film, a selective reflection film, a brightness enhancement film and a viewing angle-compensation film.

The invention includes item [1] described above and items [2] to [29] described below.

[2] The polymerizable liquid crystal compound according to item [1], wherein $A^1$ and $A^2$ are each independently 1,4-cyclohexylene, 1,4-phenylene, naphthalene-2,6-diyl or fluorene-2,7-diyl, and in the 1,4-phenylene and fluorene-2,7-diyl, arbitrary one or two hydrogens may be replaced by fluorine, methyl or trifluoromethyl.

[3] The polymerizable liquid crystal compound according to item [1] or [2], wherein $Z^1$ is a single bond, —COO—, —OCO—, —CH=CH—COO—, —$CH_2CH_2$—COO—, —OCO—CH=CH—, —OCO—$CH_2CH_2$——$CH_2CH_2$— or —C≡C—; and m is an integer from 1 to 3.

[4] The polymerizable liquid crystal compound according to item [1] or [2], wherein $Z^1$ is a single bond, —COO— or —OCO—; and m is 1 or 2.

[5] The polymerizable liquid crystal compound according to any one of items [1] to [4], wherein $P^2$ is a polymerizable group represented by any one of formula (2-1) to formula (2-4); $Q^1$ is —COO—, —OCO— or alkylene having 2 to 14 carbons, and in the alkylene arbitrary hydrogen may be replaced by fluorine and arbitrary —$CH_2$— may be replaced by —O—, —COO—, —OCO—, —CH=CH— or —C≡C—; $Q^2$ is alkylene having 1 to 14 carbons in which arbitrary —$CH_2$— may be replaced by —O— and arbitrary hydrogen may be replaced by fluorine when $P^2$ is a polymerizable group represented by formula (2-2), and $Q^2$ is a group defined in $Q^1$ when $P^2$ is a polymerizable group represented by formula (2-1), formula (2-3) or formula (2-4).

[6] The polymerizable liquid crystal compound according to any one of items [1] to [4], wherein $P^2$ is a polymerizable group represented by any one of formula (2-1) to formula (2-4); $Q^1$ is —COO—, —OCO— or alkylene having 2 to 14 carbons, and in the alkylene arbitrary —$CH_2$—may be replaced by —O—, —COO— or —OCO—; $Q^2$ is alkylene having 1 to 14 carbons in which arbitrary —$CH_2$— may be replaced by —O— when $P^2$ is a polymerizable group represented by formula (2-2), and $Q^2$ is a group defined in $Q^1$ when $P^2$ is a polymerizable group represented by formula (2-1), formula (2-3) or formula (2-4).

[7] The polymerizable liquid crystal compound according to any one of items [1] to [6], wherein $R^a$ in formula (2-2) to formula (2-4) is independently hydrogen, methyl or ethyl.

[8] The polymerizable liquid crystal compound according to item [1], wherein $A^1$ and $A^2$ are each independently 1,4-cyclohexylene, 1,4-phenylene, naphthalene-2,6-diyl or fluorene-2,7-diyl, and in the 1,4-phenylene and fluorene-2,7-diyl, arbitrary hydrogen may be replaced by fluorine, methyl or trifluoromethyl; $Z^1$ is a single bond, —COO—, —OCO—, —CH=CH—COO—, —$CH_2CH_2$—COO—, —OCO—CH=CH—, —OCO—$CH_2CH_2$—$CH_2CH_2$— or —C≡C—; m is an integer from 1 to 3; $P^2$ is a polymerizable group represented by any one of formula (2-1) to formula (2-4); $Q^1$ is —COO—, —OCO— or alkylene having 2 to 14 carbons, and in the alkylene arbitrary hydrogen may be replaced by fluorine and arbitrary —$CH_2$— may be replaced by —O—, —COO—, —OCO—, —CH═CH— or —CH≡C—; Q² is alkylene having 1 to 14 carbons in which arbitrary —CH₂— may be replaced by —O— and arbitrary hydrogen may be replaced by fluorine when P² is a polymerizable group represented by formula (2-2) and Q² is a group defined in Q¹ when P² is a polymerizable group represented by formula (2-1), formula (2-3) or formula (2-4); and R^a in formula (2-2) to formula (2-4) is independently hydrogen, methyl or ethyl.

[9] The polymerizable liquid crystal compound according to item [1], wherein A¹ and A² are each independently 1,4-cyclohexylene or 1,4-phenylene, and in the 1,4-phenylene arbitrary one or two hydrogens may be replaced by fluorine or methyl; Z¹ is a single bond, —OCO— or —COO—; m is 1 or 2; P² is a polymerizable group represented by any one of formula (2-1) to formula (2-4); Q¹ is —COO—, —OCO— or alkylene having 2 to 14 carbons, and in the alkylene arbitrary —CH₂— may be replaced by —O—, —COO— or —OCO—; Q² is alkylene having 1 to 14 carbons in which arbitrary —CH₂— may be replaced by —O— when P² is a polymerizable group represented by formula (2-2) and Q² is a group defined in Q¹ when P² is a polymerizable group represented by formula (2-1), formula (2-3) or formula (2-4); and R^a in formula (2-2) to formula (2-4) is independently hydrogen, methyl or ethyl.

[10] The polymerizable liquid crystal compound according to item [1], wherein and A² are each independently 1,4-cyclohexylene or 1,4-phenylene, and in the 1,4-phenylene arbitrary one or two hydrogens may be replaced by fluorine or methyl; Z¹ is a single bond, —COO— or —OCO—; m is 1 or 2; P² is a polymerizable group represented by formula (2-1); Q¹ and Q² are each independently —COO—, —COO—, or alkylene having 2 to 14 carbons in which arbitrary —CH₂— may be replaced by —O—, —COO— or —OCO—.

[11] The polymerizable liquid crystal compound according to item [1], wherein A¹ and A² are each independently 1,4-cyclohexylene or 1,4-phenylene, and in the 1,4-phenylene arbitrary one or two hydrogens may be replaced by fluorine or methyl; Z¹ is a single bond, —COO— or —OCO—; in is 1 or 2; P² is a polymerizable group represented by formula (2-2); Q¹ is —COO—, —OCO— or alkylene having 2 to 14 carbons, and in the alkylene arbitrary —CH₂— may be replaced by —O—, —COO— or —OCO—; Q² is alkylene having 1 to 14 carbons in which arbitrary —CH₂— may be replaced by —O—; and R^a in formula (2-2) is hydrogen.

[12] The polymerizable liquid crystal compound according to item [1], wherein A¹ and A² are each independently 1,4-cyclohexylene or 1,4-phenylene, and in the 1,4-phenylene arbitrary one or two hydrogens may be replaced by fluorine or methyl; Z¹ is a single bond, —COO— or —OCO—; m is 1 or 2; P² is a polymerizable group represented by formula (2-3); Q¹ and Q² are each independently —COO—, —OCO— or alkylene having 2 to 14 carbons, and in the alkylene arbitrary —CH₂— may be replaced by —O—, —COO— or —OCO—; and R^a in formula (2-3) is hydrogen.

[13] The polymerizable liquid crystal compound according to item [1], where A¹ and A² are each independently 1,4-cyclohexylene or 1,4-phenylene, and in the 1,4-phenylene arbitrary one or two hydrogens may be replaced by fluorine or methyl; Z¹ is a single bond, —COO— or —OCO—; m is 1 or 2; P² is a polymerizable group represented by formula (2-4); Q¹ and Q² are each independently —COO—, —OCO— or alkylene having 2 to 14 carbons, and in the alkylene arbitrary —CH₂— may be replaced by —O—, —COO— or —OCO—; and R^a in formula (2-4) is methyl or ethyl.

[14] A polymerizable liquid crystal composition, including at least one of polymerizable liquid crystal compounds represented by formula (1) and at least one compound selected from the group of polymerizable liquid crystal compounds represented by formula (M1) and formula (M2):

$$P^1—Q^1—A^1-(Z^1—A^2)_m—Q^2—P^2 \quad (1)$$

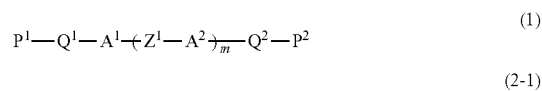

(2-1)

(2-2)

(2-3)

(2-4)

wherein

A¹ and A² are each independently 1,4-cyclohexylene, 1,4-phenylene, pyridine-2,5-diyl, pyrimidine-2,5-diyl, naphthalene-2,6-diyl, tetrahydronaphthalene-2,6-diyl, 1,3-dioxane-2,5-diyl or fluorene-2,7-diyl, and in the 1,4-phenylene and fluorene-2,7-diyl arbitrary hydrogen may be replaced by fluorine, chlorine, cyano, methyl, ethyl, methoxy, hydroxy, formyl, acetoxy, acetyl, trifluoroacetyl, difluoromethyl or trifluoromethyl;

Z¹ is a single bond, —O—, —COO—, —OCO—, —CH═CH—COO—, —OCO—CH═CH—, —OCO—CH₂CH₂—, —CH₂CH₂—COO—, —C≡C—COO—, —OCO—C≡C—, —CH₂O—, —OCH₂—, —CF₂O—, —OCF₂—, —CONH—, —NHCO—, —(CH₂)₄—, —CH₂CH₂—, —CF₂CF₂—, —CH═CH—, —CF═CF— or —C≡C—;

m is an integer from 0 to 5, where arbitrary two of A² may be the same rings or different rings and arbitrary two of Z¹ may be the same bonding groups or different bonding groups, when m is 2 or more;

P¹ is a polymerizable group represented by formula (2-1);

Q¹ is alkylene having 1 to 20 carbons, and in the alkylene arbitrary hydrogen may be replaced by fluorine and arbitrary —CH₂— may be replaced by —O—, —COO—, —OCO—, —CH═CH— or —C≡C—;

P² is a polymerizable group represented by any one of formula (2-1) to formula (2-4), hydrogen, fluorine, cyano, trifluoromethyl, trifluoromethoxy, alkyl having 1 to 20 carbons or alkoxy having 1 to 20 carbons;

$Q^2$ is a group defined in $Q^1$ when $P^2$ is a polymerizable group, and $Q^2$ is a single bond when $P^2$ is not a polymerizable group:

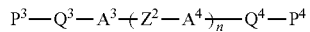 (M1)

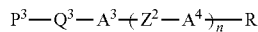 (M2)

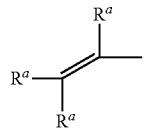 (2-2)

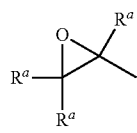 (2-3)

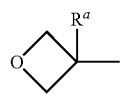 (2-4)

wherein $A^3$ and $A^4$ are each independently 1,4-cyclohexylene, 1,4-phenylene, naphthalene-2,6-diyl, fluorene-2,7-diyl or 1,3-dioxane-2,5-diyl, and in the 1,4-phenylene and fluorene-2,7-diyl, arbitrary hydrogen may be replaced by fluorine or chlorine and arbitrary hydrogen may be replaced by cyano, methyl, ethyl, methoxy, hydroxy, formyl, acetoxy, acetyl, trifluoroacetyl, difluoromethyl or trifluoromethyl;

$Z^2$ is independently a single bond, —O—, —COO—, —OCO—, —CH=CH—COO—, —OCO—CH=CH—, —OCO—CH$_2$CH$_2$—, —CH$_2$CH$_2$—COO—, —C≡C—COO—, —OCO—C≡C—, —CH$_2$O—, —OCH$_2$—, —CF$_2$O—, —CONH—, —NHCO—, —(CH$_2$)$_4$—, —CH$_2$CH$_2$—, —CF$_2$CF$_2$—, —CH=CH—, —CF=CF— or —C≡C—;

n is an integer from 0 to 5, where arbitrary two of $A^4$ may be the same rings or different rings and arbitrary two of $Z^2$ may be the same bonding groups or different bonding groups, when n is 2 or more;

$Q^3$ and $Q^4$ are each independently alkylene having 1 to 20 carbons, and in the alkylene arbitrary hydrogen may be replaced by fluorine and arbitrary —CH$_2$— may be replaced by —O—, —COO—, —OCO—, —CH=CH— or —C≡C—;

R is fluorine, cyano, trifluoromethyl, trifluoromethoxy, alkyl having 1 to 20 carbons or alkoxy having 1 to 20 carbons;

$P^3$ and $P^4$ are each independently a polymerizable group represented by any one of formula (2-2) to formula (2-4); and $R^a$ in formula (2-2) to formula (2-4) is independently hydrogen, halogen or alkyl having 1 to 5 carbons.

The polymerizable liquid crystal composition according to item [14], wherein in formula (1), $A^1$ and $A^2$ are each independently 1,4-cyclohexylene, 1,4-phenylene, naphthalene-2,6-diyl or fluorene-2,7-diyl, and in the 1,4-phenylene and fluorene-2,7-diyl, arbitrary hydrogen may be replaced by fluorine, methyl or trifluoromethyl; $Z^1$ is a single bond, —COO—, —OCO—, —CH=CH—COO—, —CH$_2$ CH$_2$ —COO—, —OCO—CH=CH—, —OCO—CH$_2$ CH$_2$ —, —CH$_2$ CH$_2$ — or —C≡C—; m is an integer from 1 to 3; $P^2$ is a polymerizable group represented by any one of formula (2-1) to formula (2-4); $Q^1$ is —COO—, —OCO— or alkylene having 2 to 14 carbons, and in the alkylene arbitrary hydrogen may be replaced by fluorine and arbitrary —CH$_2$— may be replaced by —O—, —COO—, —OCO—, —CH=CH— or —C≡C—; $Q^2$ is alkylene having 1 to 14 carbons in which arbitrary —CH$_2$— may be replaced by —O— and arbitrary hydrogen may be replaced by fluorine when $P^2$ is a polymerizable group represented by formula (2-2), and $Q^2$ is a group defined in $Q^1$ when $P^2$ is a polymerizable group represented by formula (2-1), formula (2-3) or formula (2-4); $R^a$ in formula (2-2) to formula (2-4) is independently hydrogen, methyl or ethyl; and in formula (M1) and formula (M2), $A^3$ and $A^4$ are each independently 1,4-cyclohexylene or 1,4-phenylene, and in the 1,4-phenylene arbitrary one or two hydrogens may be replaced by fluorine, methyl or trifluoromethyl; $Z^2$ is independently a single bond, —O—, —COO— or —OCO—; n is an integer from 1 to 3; $Q^3$ and $Q^4$ are each independently alkylene having 1 to 14 carbons, and in the alkylene arbitrary hydrogen may be replaced by fluorine and arbitrary —CH$_2$— may be replaced by —O—, —COO— or —OCO—; $R^a$ in formula (2-2) to formula (2-4) is independently hydrogen, methyl or ethyl; and the ratio of a polymerizable liquid crystal compound represented by formula (1) is in the range of approximately 5% to approximately 95% by weight, and the ratio of a compound selected from the group of polymerizable liquid crystal compounds represented by formula (M1) and formula (M2) is in the range of approximately 5% to approximately 95% by weight, based on the total amount of the polymerizable liquid crystal compound represented by formula (1) and the compound selected from the group of polymerizable liquid crystal compounds represented by formula (M1) and formula (M2).

[16] The polymerizable liquid crystal composition according to item [14], wherein in formula (1), $A^1$ and $A^2$ are each independently 1,4-cyclohexylene or 1,4-phenylene, and in the 1,4-phenylene arbitrary one or two hydrogens may be replaced by fluorine or methyl; $Z^1$ is a single bond, —OCO— or —OCO—; m is 1 or 2; $P^2$ is a polymerizable group represented by any one of formula (2-1) to formula (2-4); $Q^1$ is —COO—, —OCO— or alkylene having 2 to 14 carbons, and in the alkylene arbitrary —CH$_2$— may be replaced by —O—, —COO— or —OCO—; $Q^2$ is alkylene having 1 to 14 carbons in which arbitrary —CH$_2$— may be replaced by —O— when $P^2$ is a polymerizable group represented by formula (2-2), and $Q^2$ is a group defined in $Q^1$ when $P^2$ is a polymerizable group represented by formula (2-1), formula (2-3) or formula (2-4); $R^a$ in formula (2-2) to formula (2-4) is independently hydrogen, methyl or ethyl;

in formula (M1) and formula (M2), $A^3$ and $A^4$ are each independently 1,4-cyclohexylene or 1,4-phenylene, and in the 1,4-phenylene arbitrary one or two hydrogens may be replaced by fluorine, methyl or trifluoromethyl; $Z^2$ is independently a single bond, —O—, —COO— or —OCO—; n is 1 or 2; $Q^3$ and $Q^4$ are each independently alkylene having 1 to 14 carbons, and in the alkylene arbitrary hydrogen may be replaced by fluorine and arbitrary —CH$_2$— may be replaced by —O—, —COO— or —OCO—; $R^a$ in formula (2-2) to formula (2-4) is independently hydrogen, methyl or ethyl; and the ratio of a polymerizable liquid crystal compound represented by formula (1) is in the range of approximately 10% to approximately 90% by weight, and the ratio of a compound selected from the group of polymerizable liquid crystal compounds represented by formula (M1) and formula (M2) is in the range of approximately 10% to approximately 90% by weight, based on the total amount of the polymerizable liquid crystal compound represented by formula (1) and the compound selected from the group of polymerizable liquid crystal compounds represented by formula (M1) and formula (M2).

The polymerizable liquid crystal composition according to any one of items [14] to [16], wherein the ratio of a polymerizable liquid crystal compound represented by formula (1) is in the range of approximately 30% to approximately 80% by weight, and the ratio of a compound selected from the group of polymerizable liquid crystal compounds represented by formula (M1) and formula (M2) is in the range of approximately 20% to approximately 70% by weight, based on the total amount of the polymerizable liquid crystal compound represented by formula (1) and the compound selected from the group of polymerizable liquid crystal compounds represented by formula (M1) and formula (M2).

[18] The polymerizable liquid crystal composition according to any one of items [14] to [16], wherein the ratio of a polymerizable liquid crystal compound represented by formula (1) is in the range of approximately 40% to approximately 70% by weight, and the ratio of a compound selected from the group of polymerizable liquid crystal compounds represented by formula (M1) and formula (M2) is in the range of approximately 30% to approximately 60% by weight, based on the total amount of the polymerizable liquid crystal compound represented by formula (1) and the compound selected from the group of polymerizable liquid crystal compounds represented by formula (M1) and formula (M2).

[19] The polymerizable liquid crystal composition according to any one of items [14] to [18], further including another polymerizable liquid crystal compound.

[20] The polymerizable liquid crystal composition according to any one of items [14] to [19], further including a polymerizable and optically active compound.

[21] The polymerizable liquid crystal composition according to any one of items [14] to [20], further including a non-polymerizable liquid crystal compound.

[22] The polymerizable liquid crystal composition according to any one of items [14] to [21], further including a non-polymerizable and optically active compound.

[23] A film having optical anisotropy, including a polymer formed by polymerization of at least one of compounds according to any one of items [1] to [13].

[24] A film having optical anisotropy that is formed by polymerization of the polymerizable liquid crystal composition according to any one of [14] to [22].

[25] The film having optical anisotropy according to item 23 or 24, wherein the film has optical properties of an A-plate.

[26] The film having optical anisotropy according to item 23 or 24, wherein the film has optical properties of a C-plate.

[27] The film having optical anisotropy according to item 23 or 24, wherein the film has optical properties of a negative C-plate.

[28] The film having optical anisotropy according to item 23 or 24, wherein the film has optical properties of an O-plate.

[29] A liquid crystal display device containing the film having optical anisotropy according to any one of items [23] to [28].

The compound (1) of the invention is characterized by an extremely high chemical and physical stability under the conditions usually used and a high solubility in a polar solvent. The rise and fall of optical anisotropy (Δn), viscosity and so forth can be adjusted by a suitable selection of the ring, the bonding group and the side chain constituting the compound of the invention. Even when atoms constituting the compound of the invention are isotopes, the compound can be used desirably because its characteristics are equivalent to those of the original compound.

The compound (1) is easily cured in air because a polymerizing mode belongs to cationic polymerization. In the monofunctional compound, optical properties of the composition and solubility in a solvent can easily be adjusted because of a high degree of freedom for selecting a substituent. A polymer formed from the bifunctional compound has a more rigid cross-link structure in comparison with that formed from the monofunctional compound, and thus it has a higher heat resistance, a lower water-absorptivity, a lower water-permeability, a lower gas-permeability and a higher mechanical strength (especially in hardness). Furthermore, the compound having a cyclohexene oxide moiety as a polymerizable group is characterized that it has a high solubility in a safety solvent in comparison with an epoxy compound. The safety solvent includes, but not limited to PGMEA (polyethylene glycol monomethyl ether acetate).

The polymerizable liquid crystal compound of the invention is represented by formula (1).

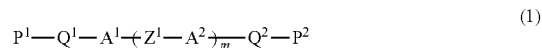

(1)

$A^1$ and $A^2$ are each independently 1,4-cyclohexylene, 1,4-phenylene, pyridine-2,5-diyl, pyrimidine-2,5-diyl, naphthalene-2,6-diyl, tetrahydronaphthalene-2,6-diyl, 1,3-dioxane-2,5-diyl or fluorene-2,7-diyl. In the 1,4-phenylene and fluorene-2,7-diyl, arbitrary hydrogen may be replaced by fluorine, chlorine, cyano, methyl, ethyl, methoxy, hydroxy, formyl, acetoxy, acetyl, trifluoroacetyl, difluoromethyl or trifluoromethyl. Desirable $A^1$ and $A^2$ are each independently 1,4-cyclohexylene, 1,4-phenylene, naphthalene-2,6-diyl or fluorene-2,7-diyl, and in the 1,4-phenylene and fluorene-2,7-diyl one or two hydrogens may be replaced by fluorine, methyl or trifluoromethyl. More desirable and $A^2$ are each independently 1,4-cyclohexylene or 1,4-phenylene, and in the 1,4-phenylene arbitrary one or two hydrogens may be replaced by fluorine or methyl. A desirable example of $A^1$ and $A^2$ includes 1,4-cyclohexylene, 1,4-phenylene, 2-fluoro-1,4-phenylene, 2,3-difluoro-1,4-phenylene, 2,5-difluoro-1,4-phenylene, 2,6-difluoro-1,4-phenylene, 2-methyl-1,4-phenylene, 3-methyl-1,4-phenylene and 2,3-dimethyl-1,4-phenylene.

The compound shows a tendency to increase the melting point, increase the clearing point and increase the temperature range of a liquid crystal phase when both of and $A^2$ are 1,4-phenylene, and the compound shows a tendency to decrease the temperature range of a liquid crystal phase and decrease the optical anisotropy when at least one of $A^1$ and $A^2$ is 1,4-cyclohexylene.

The bonding group $Z^1$ is a single bond, —O—, —COO—, —COO—, —CH=CH—COO—, —OCO—CH=CH—, —OCO—CH$_2$CH$_2$—, —CH$_2$CH$_2$—COO—, —C≡C—COO—, —OCO—C≡C—, —CH$_2$O—, —OCH$_2$—, —CF$_2$O—, —OCF$_2$—, —CONH—, —NHCO—, —(CH$_2$)$_4$—, —CH$_2$CH$_2$—, —CF$_2$CF$_2$—CH=CH—, —CF=CF— or —C≡C—. The compound (1) shows a tendency to decrease the viscosity when $Z^1$ is a single bond, —CH$_2$CH$_2$—, —CH$_2$O—, —OCH$_2$— —CF$_2$O—, —OCF$_2$—CH=CH—, —CF=CF— or —(CH$_2$)$_4$. The compound (1) shows a tendency to increase the temperature range of a liquid crystal phase and increase the ratio of the elastic constants when $Z^1$ is —CH=CH— or —CF=CF—.

A film formed by polymerization of the compound (1) shows a tendency to increase its optical anisotropy when $Z^1$ is —C≡C—.

m is an integer from 0 to 5, and desirable m is an integer from 1 to 3. An especially desirable m is 1 or 2. When in is 2 or more, arbitrary two of $A^2$ may be the same rings or different rings and arbitrary two of $Z^1$ may be the same bonding groups or different bonding groups.

$P^1$ is a polymerizable group represented by formula (2-1). $P^2$ is a polymerizable group represented by any one of formula (2-1) to formula (2-4), hydrogen, fluorine, cyano, trifluoromethyl, trifluoromethoxy, alkyl having 1 to 20 carbons or alkoxy having 1 to 20 carbons. Desirable $P^1$ is a polymerizable group represented by any one of formula (2-1) to formula (2-4).

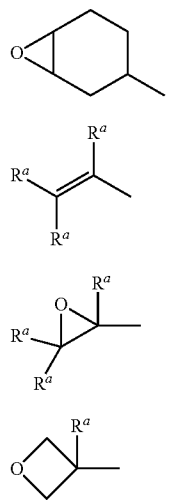

$R^a$ in formula (2-2) to formula (2-4) is independently hydrogen, halogen or alkyl having 1 to 5 carbons, and desirable $R^a$ is independently hydrogen, methyl or ethyl. The compound (1) shows a tendency to increase solubility in an organic solvent and increase a polymerization rate of the compound (1) when both $P^1$ and $P^2$ are a polymerizable group represented by formula (2-1). The compound (1) shows a tendency to increase hardness of a film formed by polymerization of the compound (1) when $P^2$ is formula (2-3). The compound (1) shows a tendency to increase solubility in an organic solvent and decrease a melting point or a clearing point when $P^2$ is a polymerizable group represented by formula (2-4).

$Q^1$ is alkylene having 1 to 20 carbons, and in the alkylene arbitrary hydrogen may be replaced by fluorine and arbitrary —CH$_2$— may be replaced by —O—, —COO—, —OCO—, —CH═CH— or —C≡C—. Desirable $Q^1$ is —COO—, —OCO— or alkylene having 2 to 14 carbons, and in the alkylene arbitrary hydrogen may be replaced by fluorine and arbitrary —CH$_2$— may be replaced by —O—, —COO—, —OCO—, —CH═CH— or —C≡C—. More desirable $Q^1$ is —COO—, —OCO— or alkylene having 2 to 14 carbons in which arbitrary —CH$_2$— may be replaced by —O—, —COO— or —OCO—. Straight-chain alkylene is preferable to branched-chain alkylene when $Q^1$ is alkylene.

$Q^2$ is a group defined in $Q^1$ when $P^2$ is a polymerizable group and $Q^2$ is a single bond when $P^2$ is not a polymerizable group. Desirable $Q^2$ is alkylene having 1 to 14 carbons in which arbitrary —CH$_2$— may be replaced by —O— and arbitrary hydrogen may be replaced by fluorine, and more desirable $Q^2$ is alkylene having 1 to 14 carbons in which arbitrary —CH$_2$— may be replaced by —O— when $P^2$ is a polymerizable group represented by formula (2-2).

$Q^2$ is a group defined in $Q^1$ as described above when $P^2$ is a polymerizable group represented by formula (2-1), formula (2-3) or formula (2-4). The compound (1) shows a tendency to exhibit a wide liquid crystal temperature range when the chain length of alkylene in $Q^1$ and $Q^2$ is long, and increase solubility in a polar solvent when oxygen is incorporated in alkylene. The compound (1) shows a tendency to exhibit a high liquid crystal temperature range when $Q^1$ is —COO—.

As described above, the compound (1) having objective physical properties can be obtained by the suitable selection of the kinds of polymerizable groups, rings and bonding groups, and of the number of the rings. The compound (1) can be prepared by means of a combination of techniques in synthetic organic chemistry. Methods for an introduction of objective terminal groups, rings and bonding groups to starting materials are described in books such as Houben-Weyl, Methods of Organic Chemistry, Georg Thieme Verlag, Stuttgart; Organic syntheses, John Wily & Sons, Inc.; Organic Reactions, John Wily & Sons Inc.; Comprehensive Organic Synthesis, Pergamon Press; and New Experimental Chemistry Course (Shin Jikken Kagaku Kouza, in Japanese title), Maruzen Co., LTD. In the following scheme, the meanings of symbols that are not explained are the same with those described before.

Formation of the bonding group $Z^1$ will be explained in Schemes 1 to 13. In these schemes, $MSG^1$ and $MSG^2$ are an organic monovalent group having at least one ring. A plurality of $MSG^1$ (or $MSG^2$) may be the same or different. The compounds (1A) to (1L) correspond to the compound (1) of the invention. These synthetic methods are applicable to an optically active compound (1) and an optically inactive compound (1)

Scheme 1: Compounds where Bonding Group $Z^1$ is Single Bond

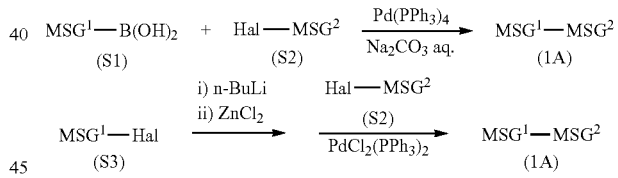

As shown below, the compound (1A) can be prepared by the reaction of the arylboronic acid (S1) with the compound (S2), which is prepared by a known method, in an aqueous solution of carbonate in the presence of catalyst such as tetrakis(triphenylphosphine)palladium. The compound (1A) can also be prepared by the reaction of the compound (S3) that is prepared by a known method, with n-butyllithium, and then with zinc chloride and by the reaction of the product with the compound (S2) in the presence of a catalyst such as dichlorobis(triphenylphosphine)palladium.

Scheme 2: Compounds where Bonding Group $Z^1$ is —CH═CH—

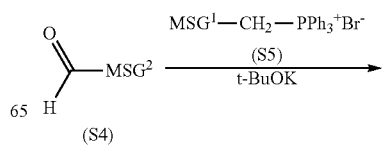

MSG¹—CH═CH—MSG²
(1B)

As shown below, the compound (1B) can be prepared by the reaction of the aldehyde (S4) with a phosphorus ylide generated by the addition of a base such as potassium t-butoxide to the phosphonium salt (S5) that is prepared by a known method. Since a cis-isomer may be formed depending on the reaction conditions and the kind of substrate, the cis-isomer is isomerized to the corresponding trans-isomer by a known method as requested.

Scheme 3: Compounds where Bonding Group $Z^1$ is —(CH$_2$)$_2$—

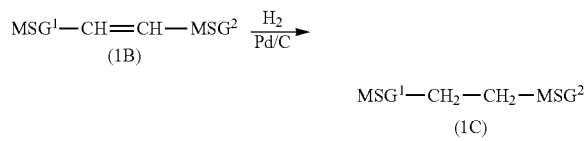

As Scheme 3 shows, the compound (1C) can be prepared by hydrogenation of the compound (1B) in the presence of a catalyst such as palladium on carbon.

Scheme 4: Compounds where Bonding Group $Z^1$ is —(CF$_2$)$_2$—

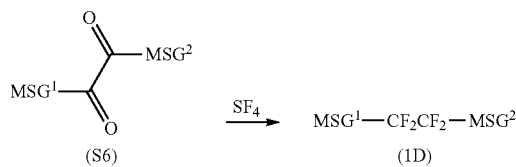

As shown below, the compound (1D) having —(CF$_2$)$_2$— can be prepared by fluorination of the diketone (S6) with sulfur tetrafluoride in the presence of a hydrogen fluoride catalyst, according to the method described in J. Am. Chem. Soc., 2001, 123, 5414.

Scheme 5: Compounds where Bonding Group $Z^1$ is —(CH$_2$)$_4$—

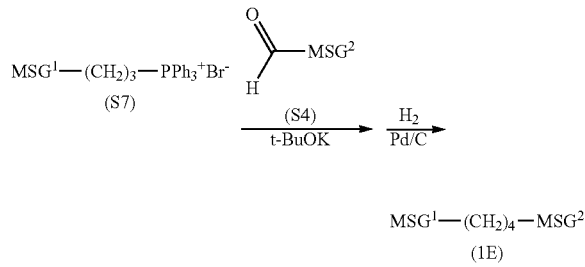

As shown below, the compound (1E) can be prepared by catalytic hydrogenation of the compound having —(CH$_2$)$_2$—CH═CH—, which is prepared using the phosphonium salt (S7) instead of the phosphonium salt (S5) according to the method in Scheme 2.

Scheme 6: Compounds where Bonding Group $Z^1$ is —CH$_2$O— or —OCH$_2$—

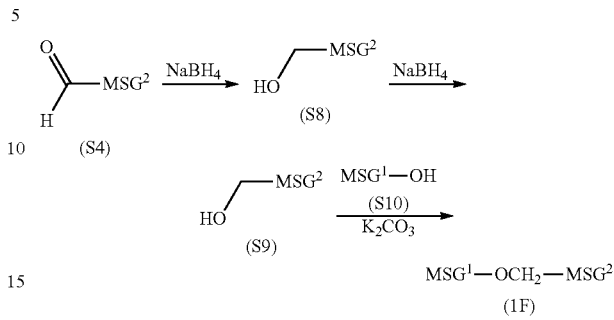

As shown below, the compound (S4) is reduced with a reducing agent such as sodium borohydride, giving the compound (S8). Then, the compound (S8) is halogenated with hydrobromic acid or the like, giving the compound (S9). The compound (1F) can be prepared by the reaction of the compound (S9) with the compound (S10) in the presence of potassium carbonate or the like. The compound having —CH$_2$O— can also be prepared in the same manner.

Scheme 7: Compounds where Bonding Group $Z^1$ is —COO— or —OCO—

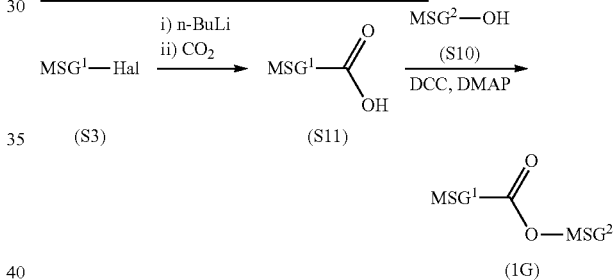

As shown below, the compound (S3) is reacted with n-butyllithium and then with carbon dioxide, giving the carboxylic acid (S11). The compound (1G) having —COO— can be prepared by the dehydration of the compound (S11) and phenol (S10) in the presence of DCC (1,3-dicyclohexylcarbodiimide) and DMAP (4-dimethylaminopyridine). The compound having —OCO— can also be prepared in the same manner. The compound (1G) can also be prepared by the action of thionyl chloride or oxalyl chloride on the compound (S11), giving the corresponding acid chloride, and then by the action of the aldehyde (S10) on the acid chloride in the presence of a base such as pyridine or triethylamine.

Scheme 8: Compounds where Bonding Group $Z^1$ is —CF═CF—

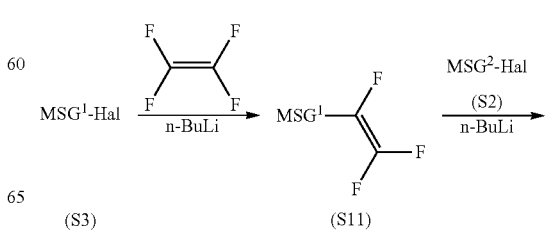

-continued

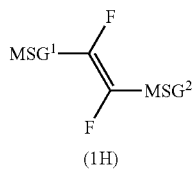

(1H)

As shown below, the compound (S3) is treated with n-butyllithium, and then reacted with tetrafluoroethylene, giving the compound (S12). The compound (1H) can be prepared by the treatment of the compound (S2) with n-butyllithium, and then by the reaction with the compound (S12). A cis-isomer of the compound (1H) can also be produced by selecting the reaction conditions.

Scheme 9: Compounds where Bonding Group $Z^1$ is —C≡C—

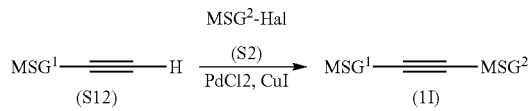

As shown below, the compound (1I) can be prepared by the reaction of the compound (S12) with the compound (S2) in the presence of a catalyst of dichloropalladium and a copper halide.

As shown below, the compound (S12) is lithiated with n-butyllithium, and then reacted with carbon dioxide, giving the carboxylic acid (S13). The compound (1J) having —C≡C—COO— can be prepared by the dehydration of the carboxylic acid (S13) and the phenol (S10) in the presence of DCC and DMAP. The compound having —OCO—C≡C— can also be prepared in the same manner. The compound (1J) can also be prepared via an acid chloride in the same way as described in the derivation of the compound (1G) from the compound (S11) in Scheme 7.

Scheme 10: Compounds where Bonding Group $Z^1$ is —C≡C—COO—

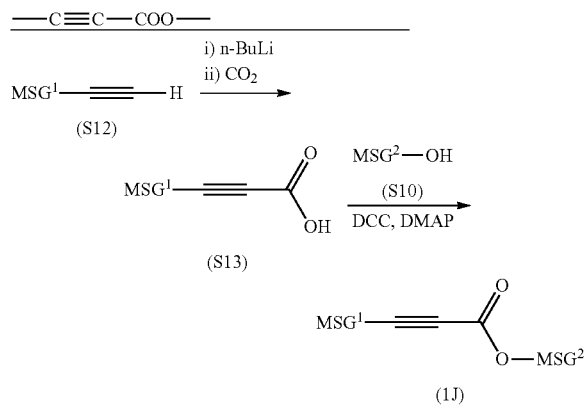

As shown below, the compound (1G) is treated with a thionating agent such as Lawesson's reagent, giving the compound (S14). The compound (1K) having —CF$_2$O— can be prepared by fluorination of the compound (S14) with a hydrogen fluoride-pyridine complex and NBS (N-bromosuccinimide). The compound (1K) can also be prepared by fluorination of the compound (S14) with (diethylamino) sulfurtrifluoride (DAST). The compound having —OCF$_2$— can also be prepared in the same manner. These bonding groups can also be formed by the method described in P. Kirsch et al., Angew. Chem. Int. Ed. 2001, 40, 1480.

Scheme 11: Compound where Bonding Group $Z^1$ is —CF$_2$O— or —OCF$_2$—

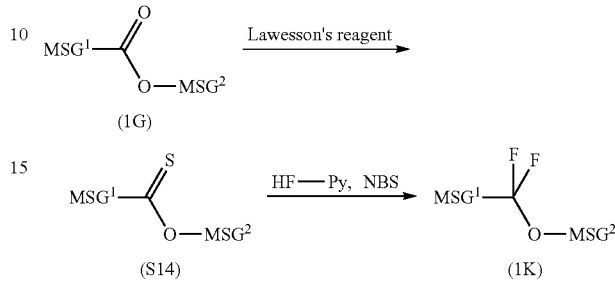

Methods for introducing a polymerizable group will be explained in Schemes 12 and 13. In these Schemes, MSG is an organic monovalent group having at least one ring. A plurality of MSG may be the same or different. Y is alkylene having 1 to 21 carbons, and in the alkylene, arbitrary hydrogen may be replaced by fluorine or chlorine and arbitrary —CH$_2$— may be replaced by —O—, —COO—, —OCO—, —CH=CH— or —C≡C—. P is a polymerizable group represented by any one of formula (2-1) to formula (2-4). The compound (1L) corresponds to the compound (1) of the invention.

Scheme 12: Earlier Introduction of Polymerizable Group

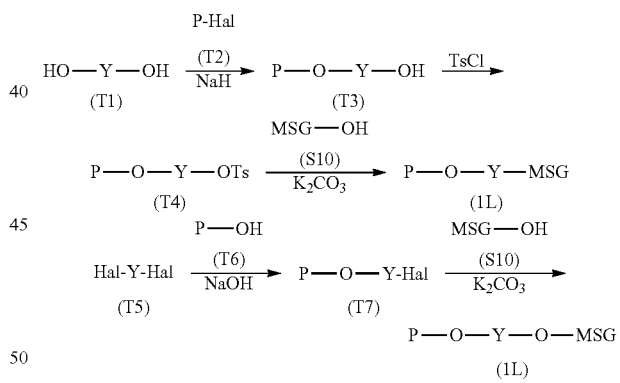

As shown below, the reaction of the diol (T1) with the compound (T2) that is prepared by a known method, in the presence of a base such as sodium hydride, gives the monoether (T3). This compound is tosylated with p-toluenesulfonyl chloride or the like, giving the tosylate (T4). The compound (1L) can be prepared by the reaction of the tosylate (T4) with the phenol (S10) in the presence of a base such as potassium carbonate. The compound (1L) can also be prepared by the reaction of the compound (T5) that is prepared by a known method, with the alcohol (T6) having a polymerizable group in the presence of a base such as sodium hydroxide, giving the monoether (T7), and then by the reaction of the monoether (T7) with the phenol (S10) in the presence of a base such as potassium carbonate.

As shown below, the reaction of the phenol (S10) with the compound (T8) that is prepared by a known method, in the presence of a base such as potassium carbonate, gives the monoether (T9). The compound (1L) can be prepared by the reaction of the monoether (T9) with the compound (T2) in the presence of a base such as sodium hydroxide.

Scheme 13: Later Introduction of Polymerizable Group

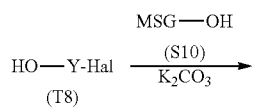

-continued

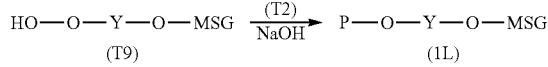

The compound (1) can be produced by way of a combination of the methods described above. However, production methods are not limited to the methods described above. An example of the compound (1) prepared by the method described above is as follows. Incidentally, the structures of compounds prepared in the manner described above can be characterized by means of, for example, proton NMR spectroscopy.

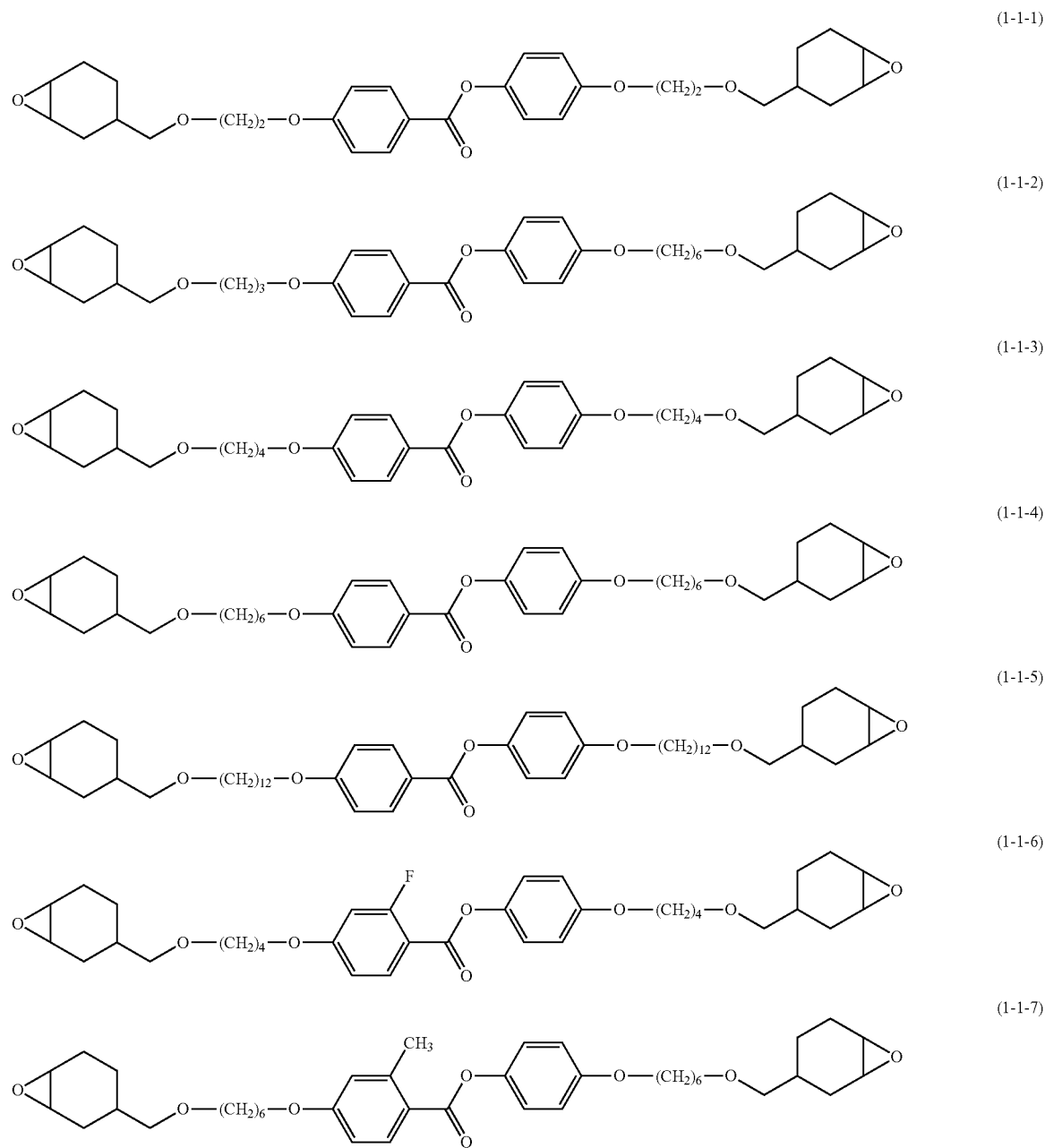

-continued
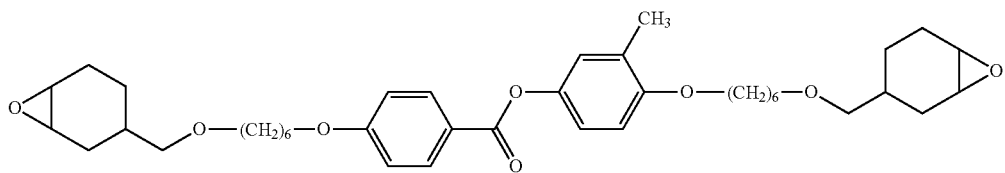
(1-1-8)
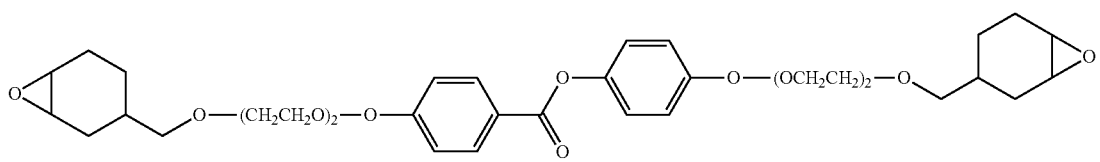
(1-1-9)
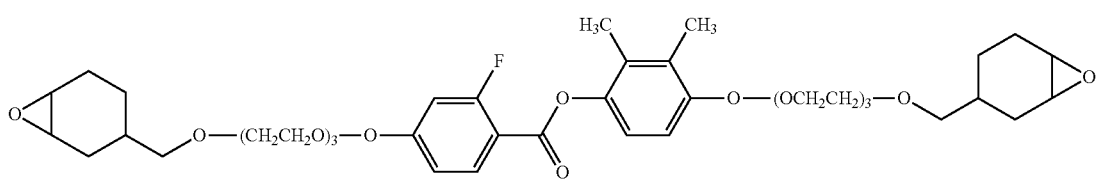
(1-1-10)
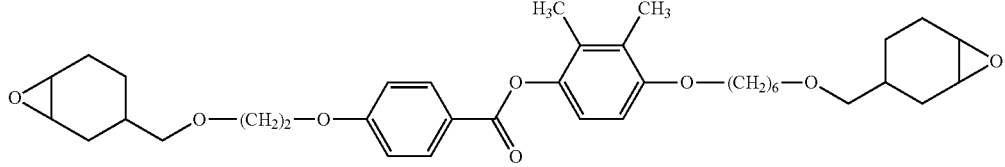
(1-1-11)
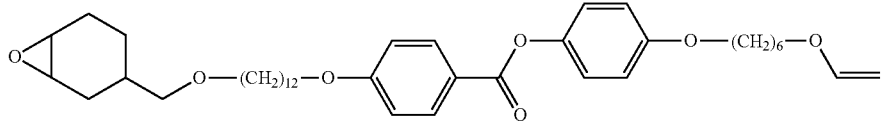
(1-1-12)
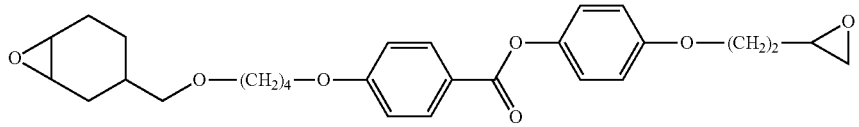
(1-1-13)
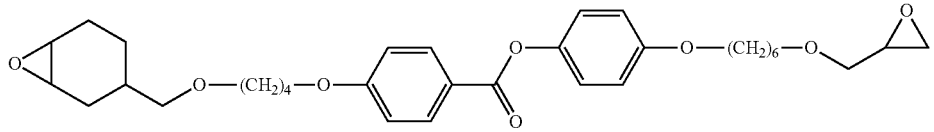
(1-1-14)
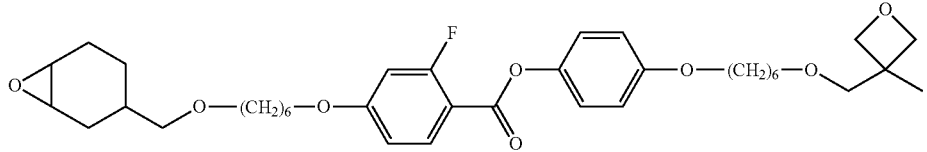
(1-1-15)
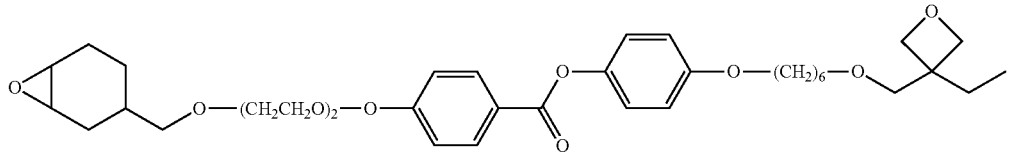
(1-1-16)

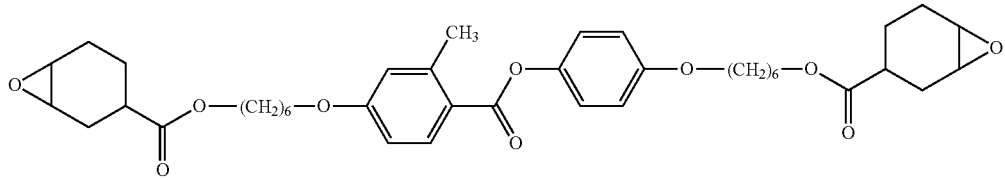
(1-1-17)
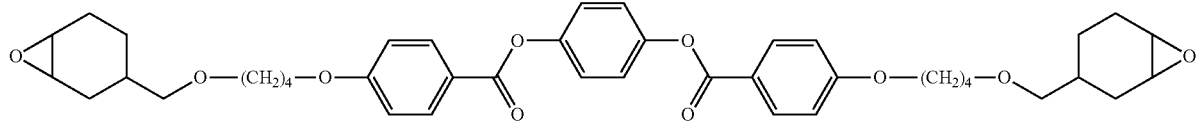
(1-1-18)
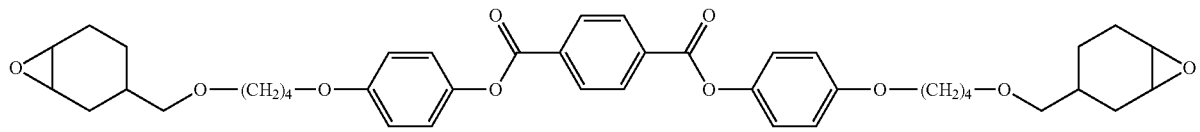
(1-1-19)
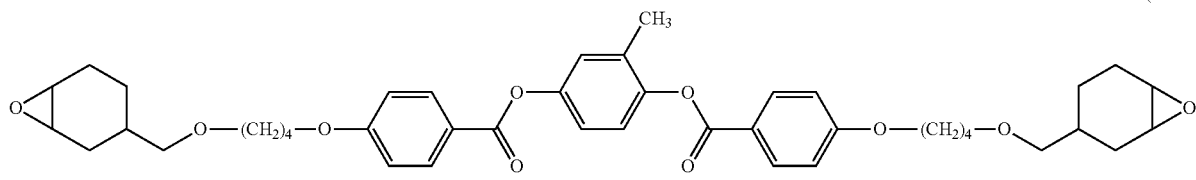
(1-1-20)
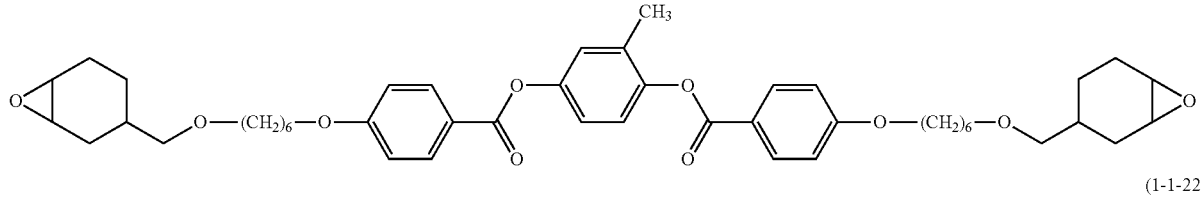
(1-1-21)
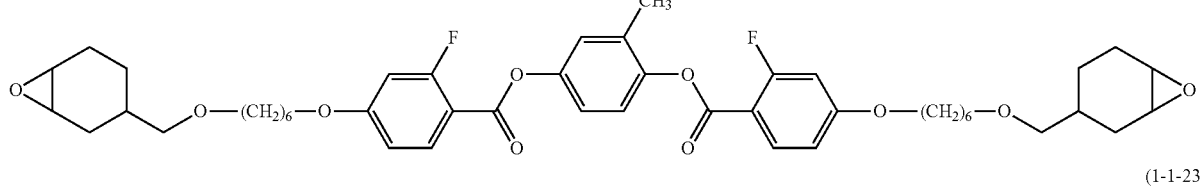
(1-1-22)
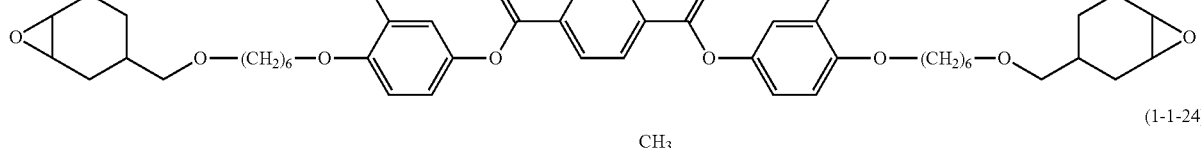
(1-1-23)
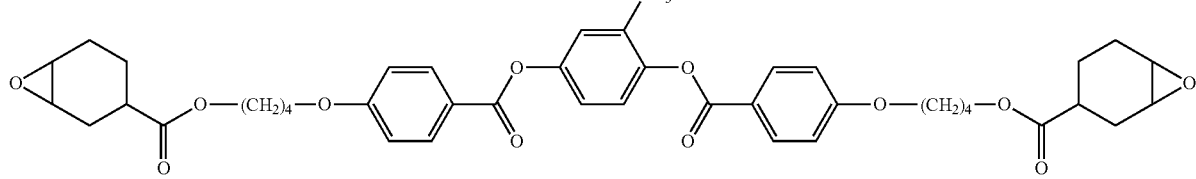
(1-1-24)
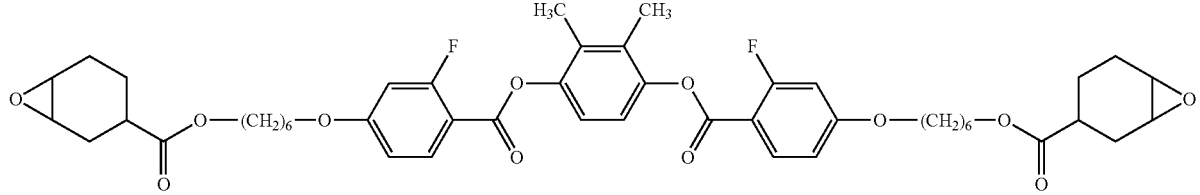
(1-1-25)

-continued
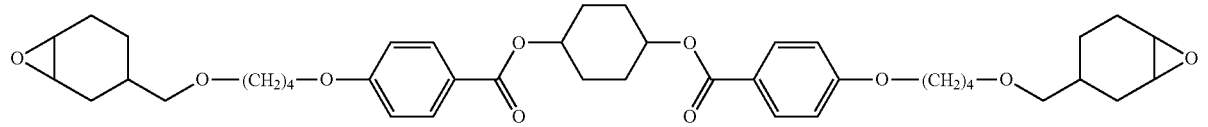
(1-1-26)
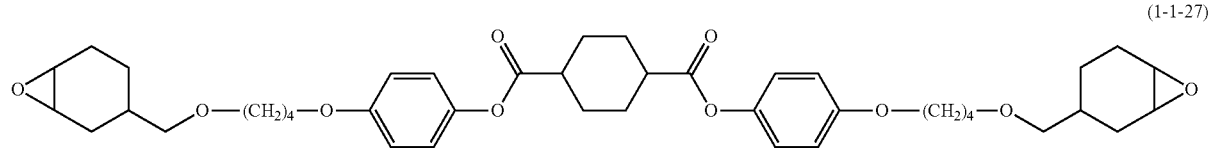
(1-1-27)
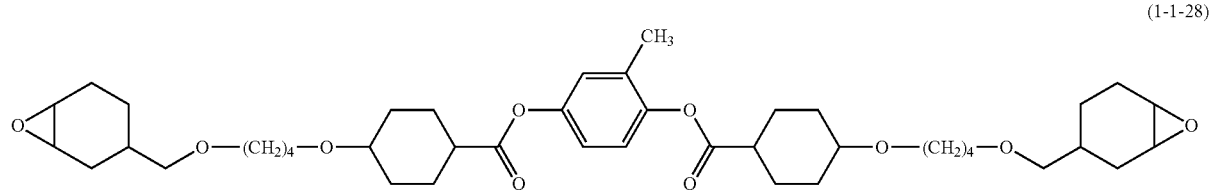
(1-1-28)
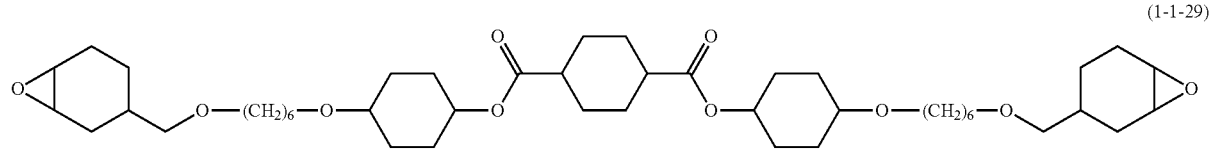
(1-1-29)
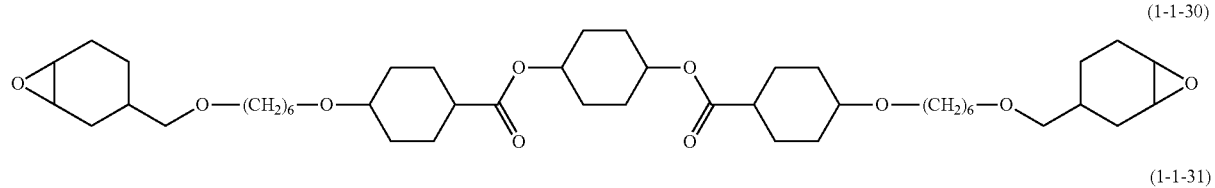
(1-1-30)
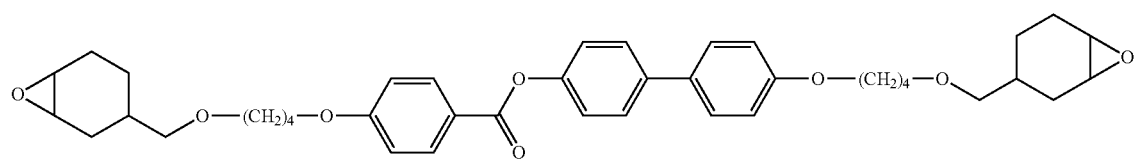
(1-1-31)
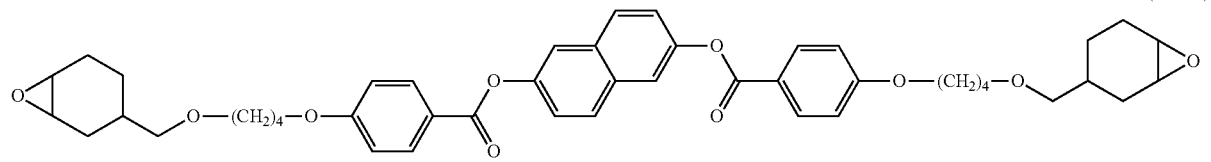
(1-1-32)
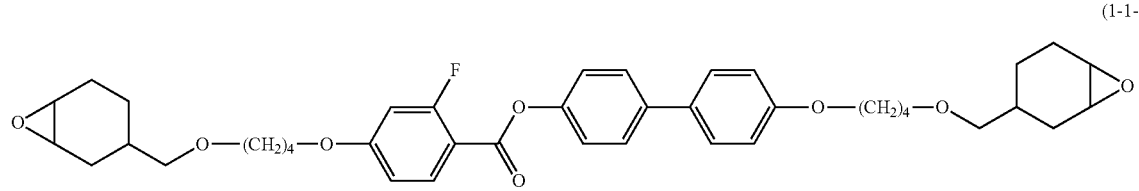
(1-1-33)
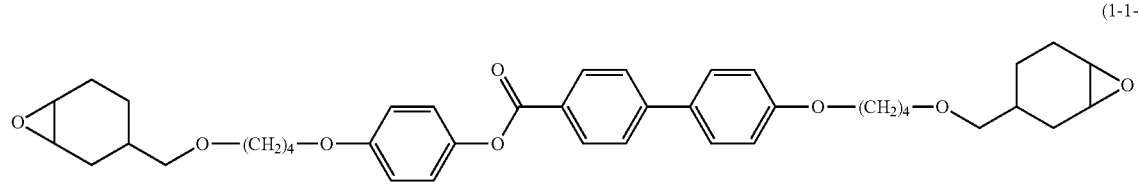
(1-1-34)

(1-3-35)
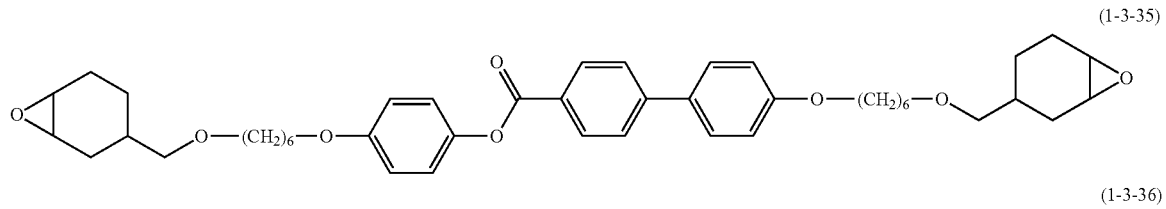
(1-3-36)
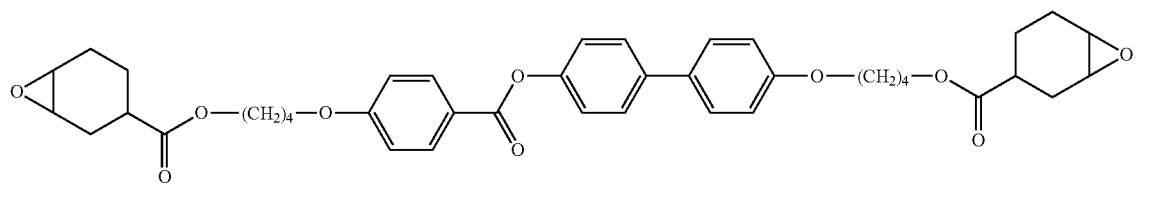
(1-3-37)
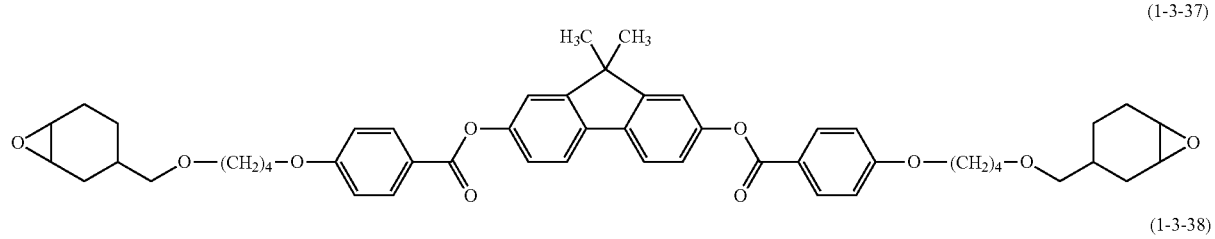
(1-3-38)
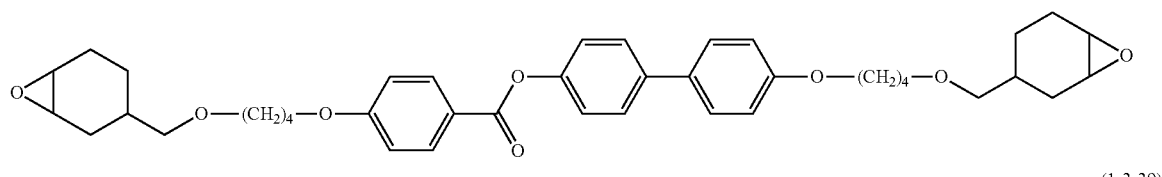
(1-3-39)
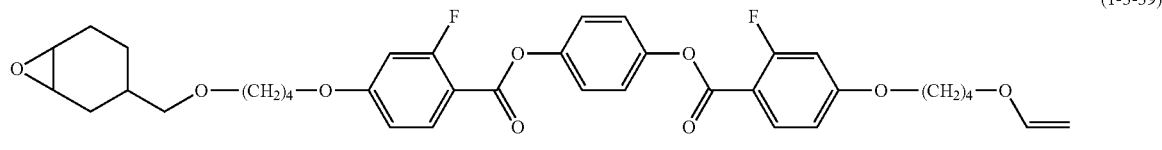
(1-3-40)
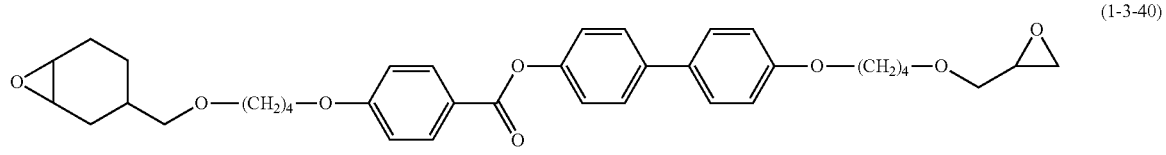
(1-3-41)
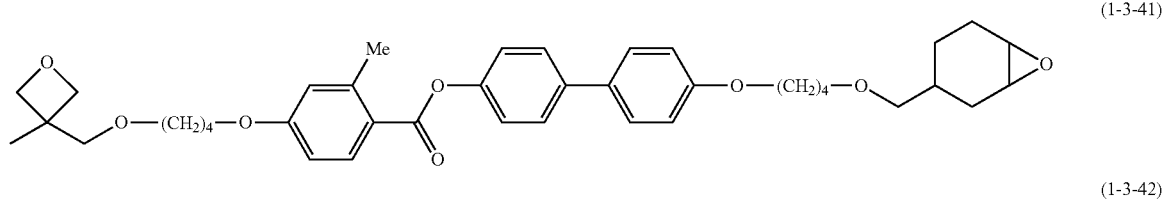
(1-3-42)
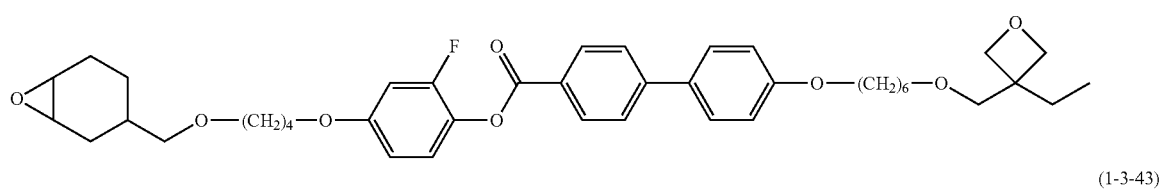
(1-3-43)
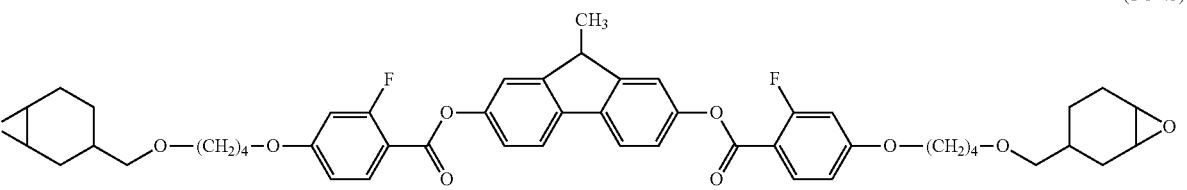

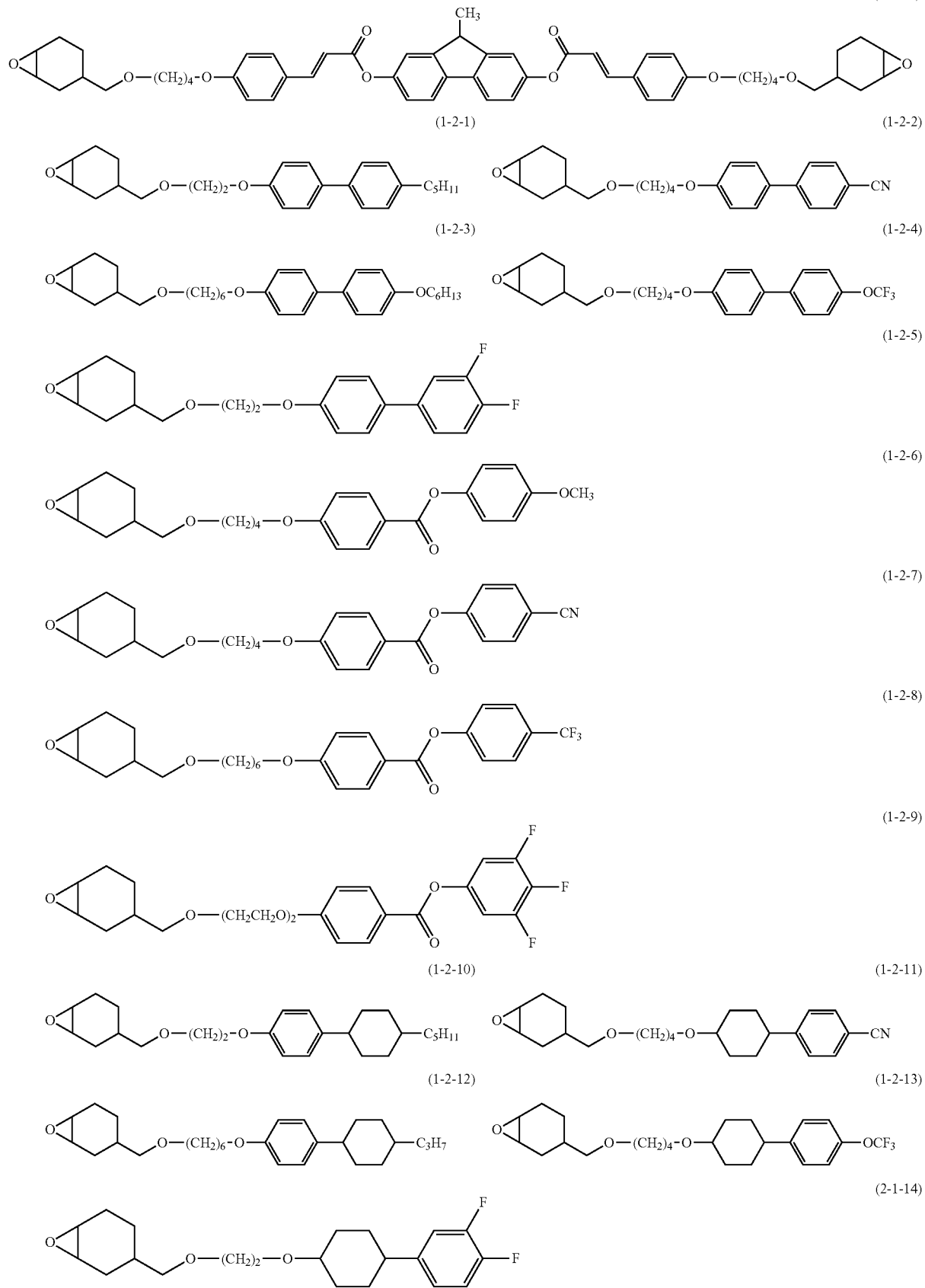

-continued
(2-1-15)
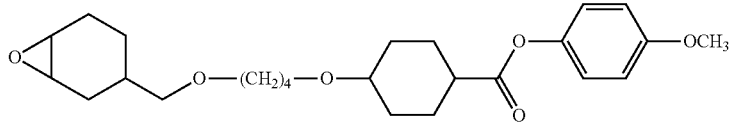
(1-2-16)
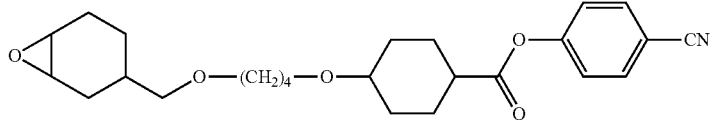
(2-1-17)
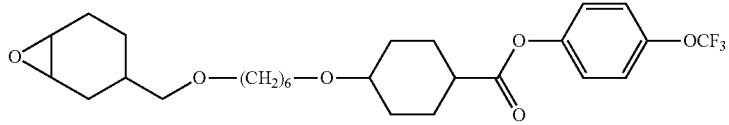
(2-1-18)
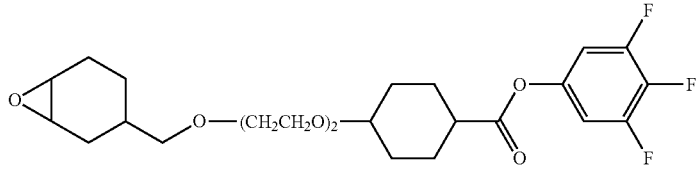
(2-1-19)
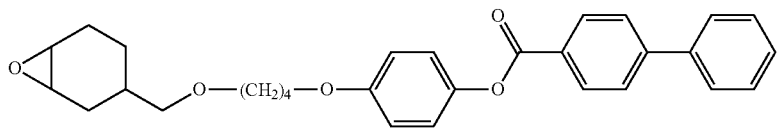
(1-3-1) (1-3-2)
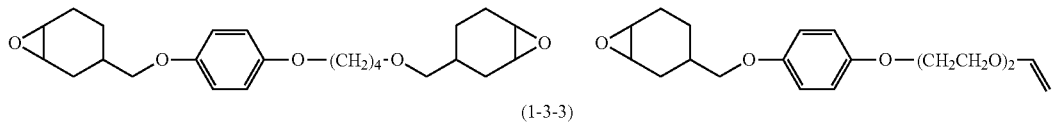
(1-3-3) (1-3-4)
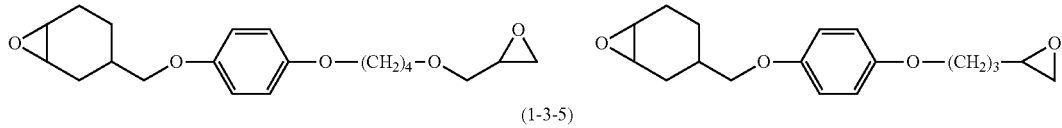
(1-3-5) (1-3-6)
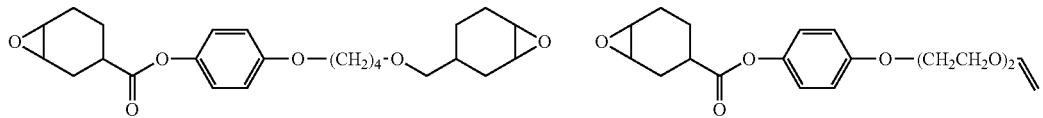
(1-3-7) (1-3-8)
(1-3-9)
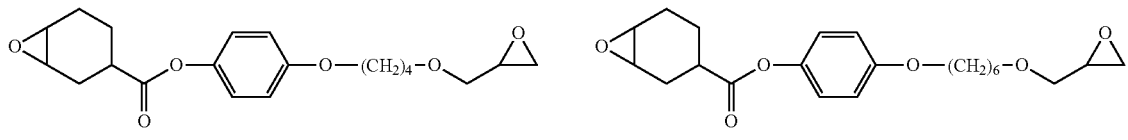
(1-3-10)
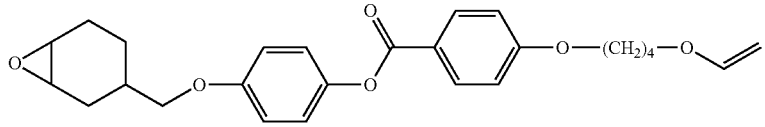

-continued
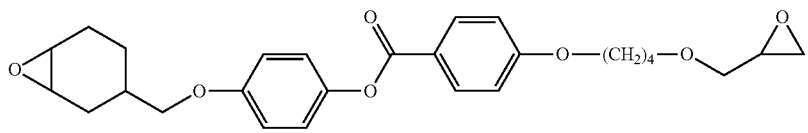
(1-3-11)
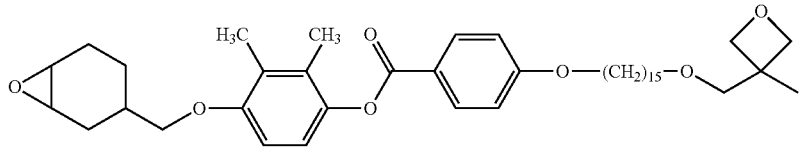
(1-3-12)
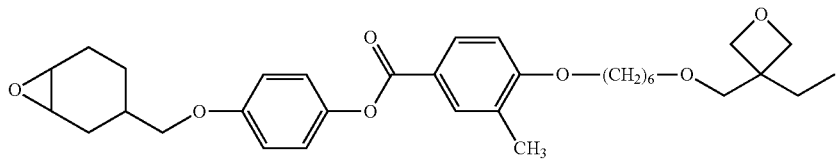
(1-3-13)
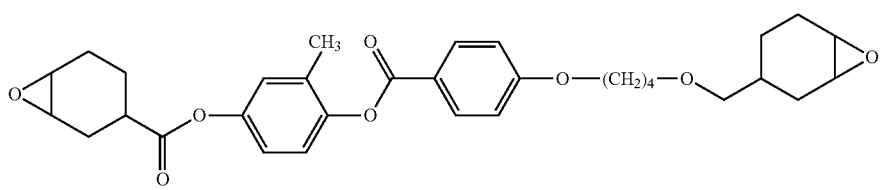
(1-3-14)
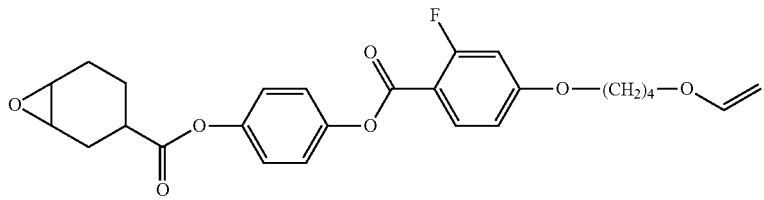
(1-3-15)
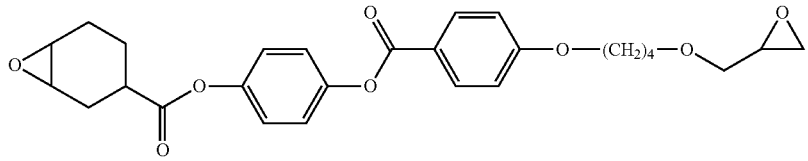
(1-3-16)
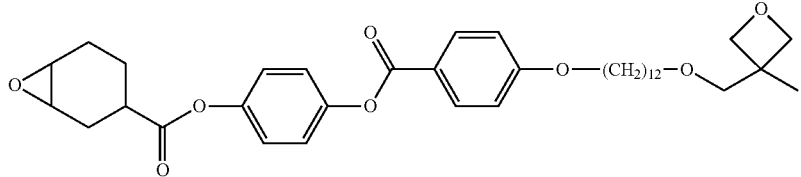
(1-3-17)
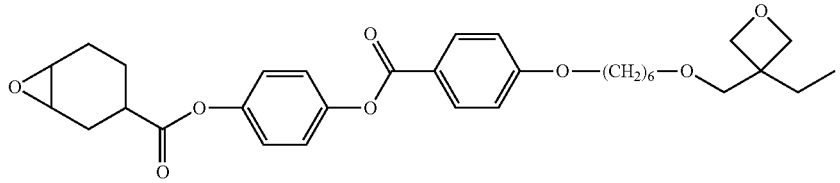
(1-3-18)
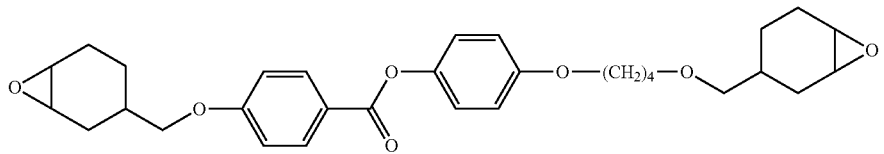
(1-3-19)

-continued
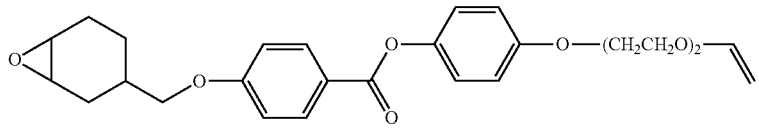
(1-3-20)
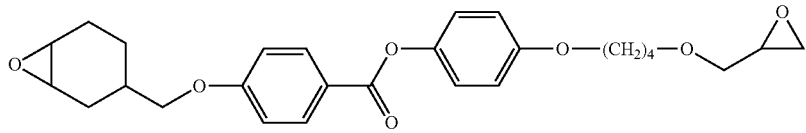
(1-3-21)
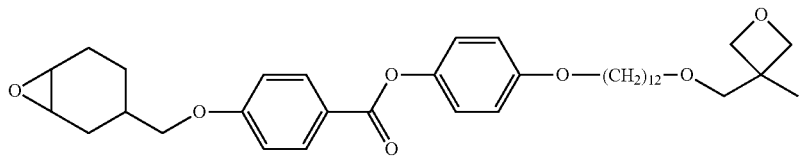
(1-3-22)
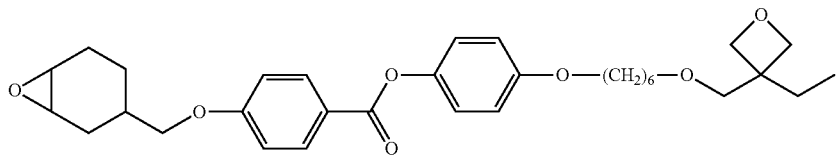
(1-3-23)
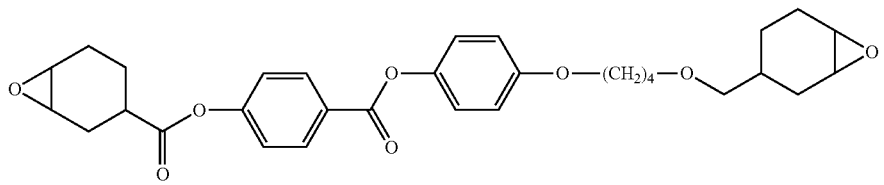
(1-3-24)
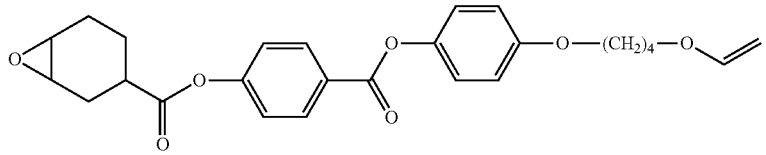
(1-3-25)
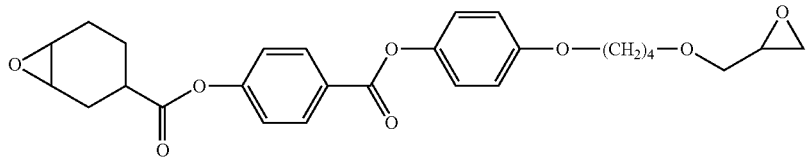
(1-3-26)
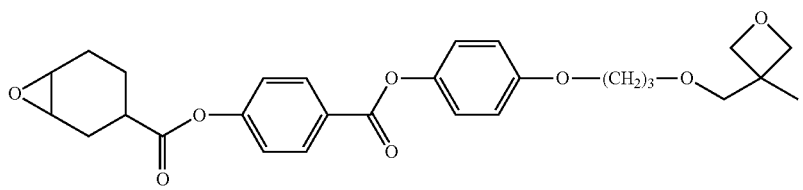
(1-3-27)
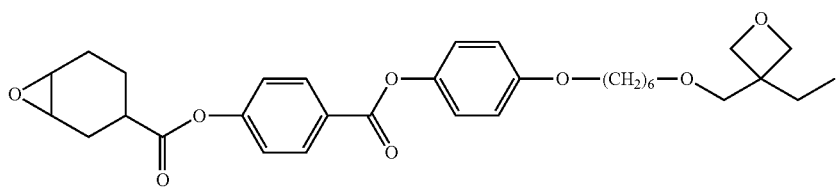
(1-3-28)

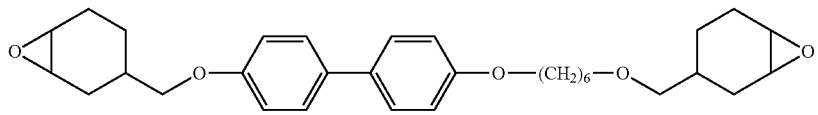 (1-3-29)
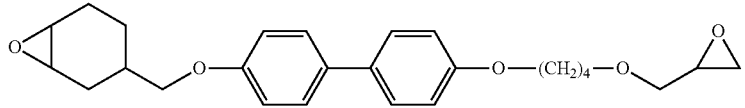 (1-3-30)
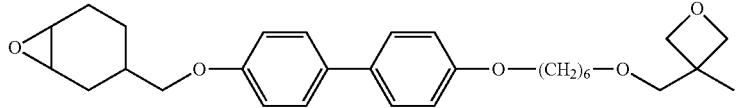 (1-3-31)
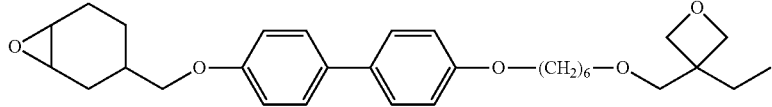 (1-3-32)
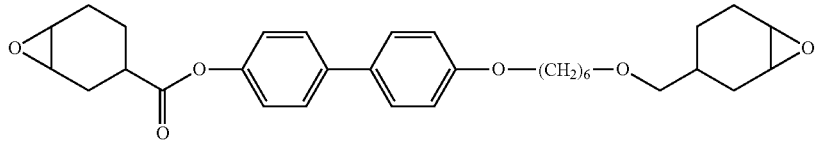 (1-3-33)
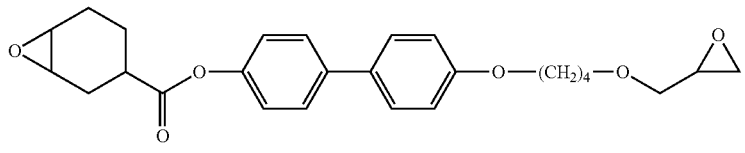 (1-3-34)
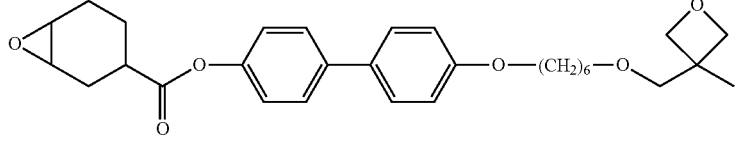 (1-3-35)
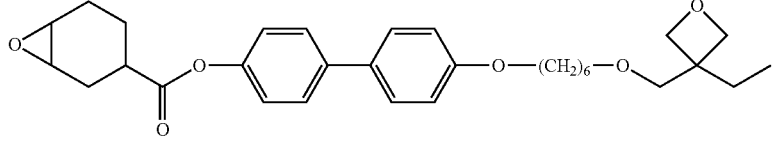 (1-3-36)
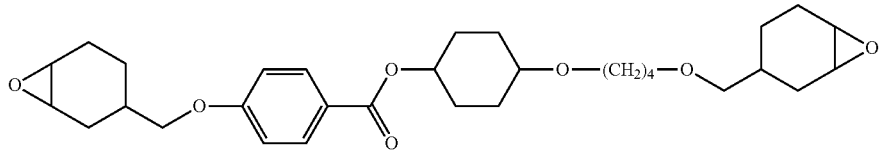 (1-3-37)
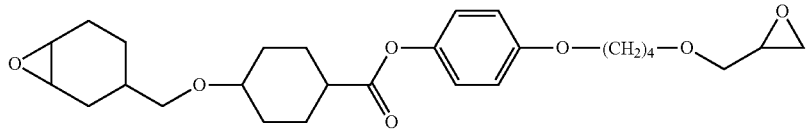 (1-3-38)
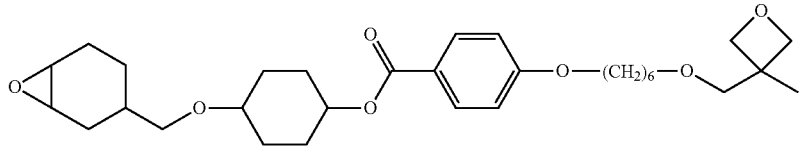 (1-3-39)

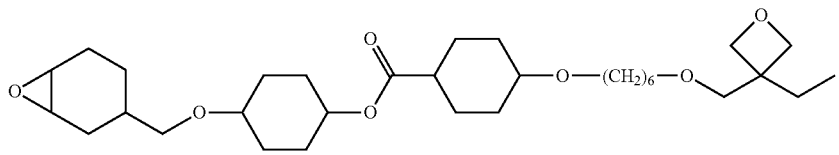
(1-3-40)
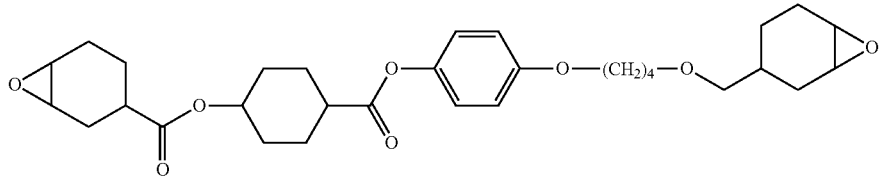
(1-3-41)
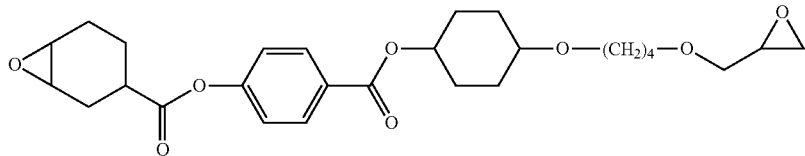
(1-3-42)
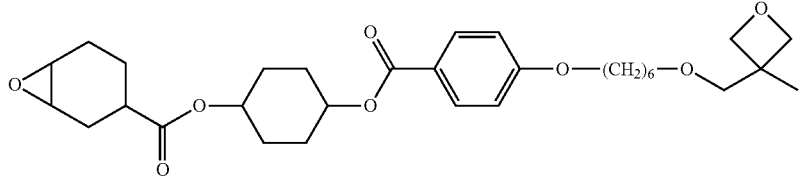
(1-3-43)
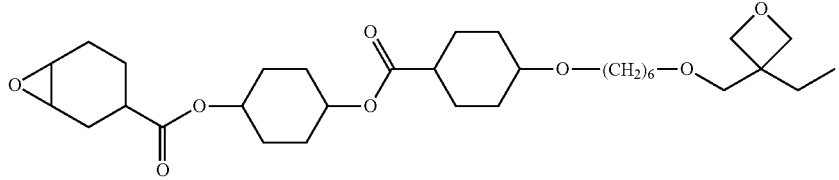
(1-3-44)
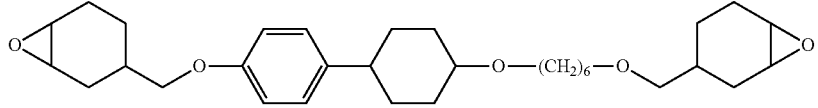
(1-3-45)
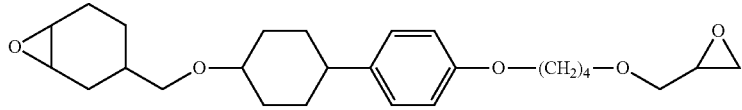
(1-3-46)
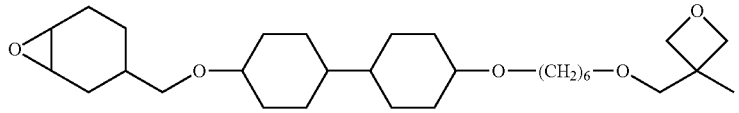
(1-3-47)
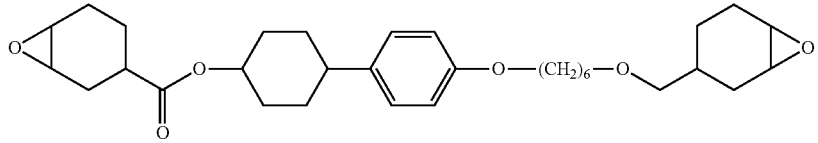
(1-3-48)
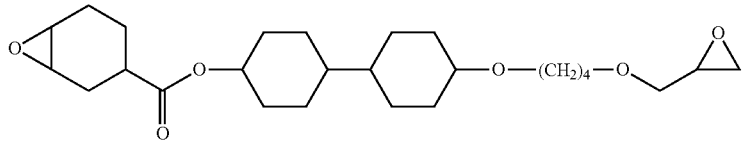
(1-3-49)

-continued
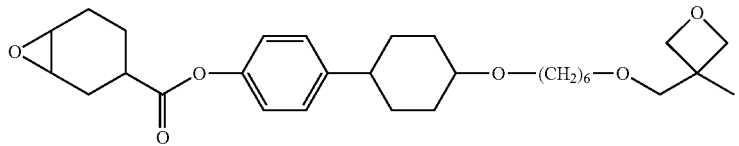
(1-3-50)
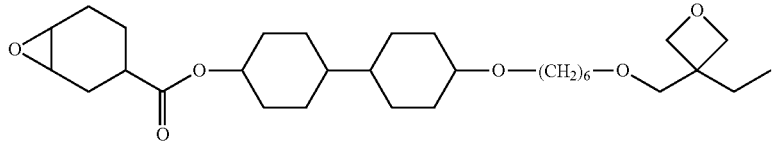
(1-3-51)
(1-4-1)
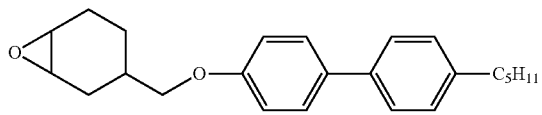
(1-4-2)
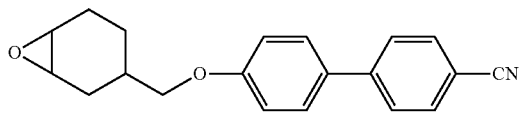
(1-4-3)
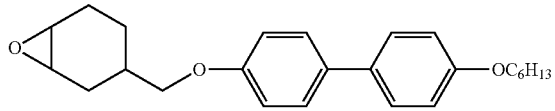
(1-4-4)
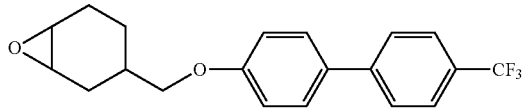
(1-4-5)
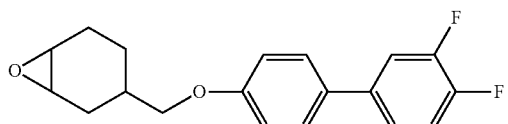
(1-4-6)
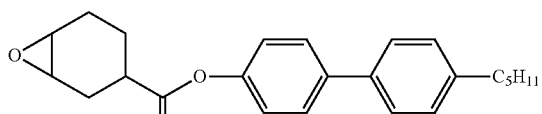
(1-4-7)
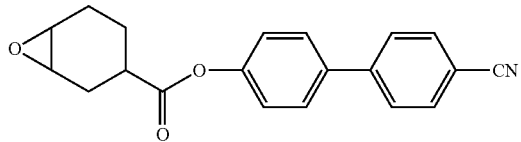
(1-4-8)
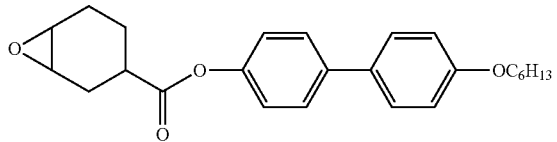
(1-4-9)
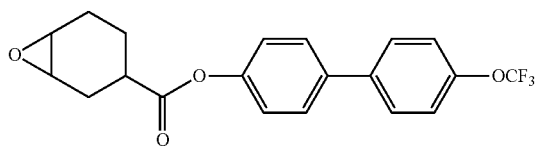
(1-4-10)
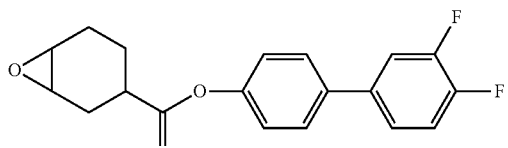
(1-4-11)
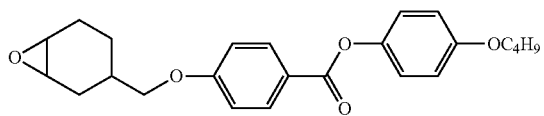
(1-4-12)
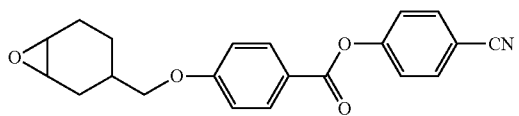
(1-4-13)
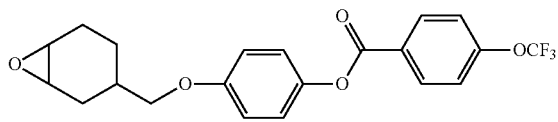
(1-4-14)
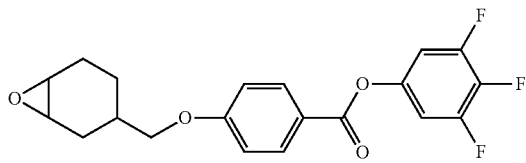

-continued
(1-4-15)
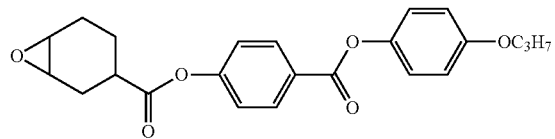
(1-4-16)
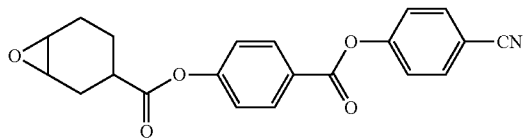
(1-4-17)
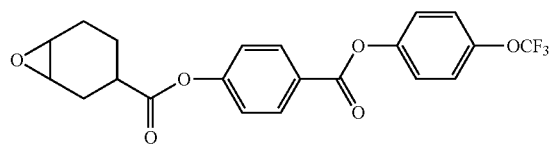
(1-4-18)
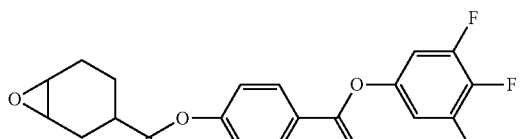
(1-4-19)
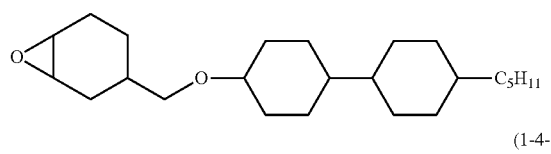
(1-4-20)
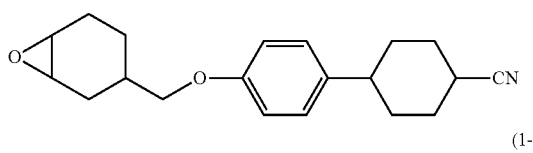
(1-4-21)
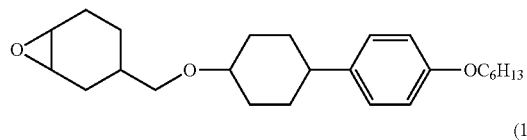
(1-4-22)
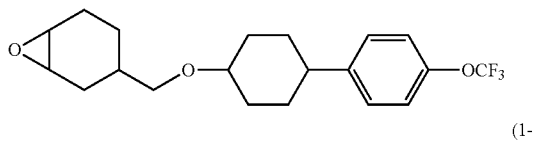
(1-4-23)
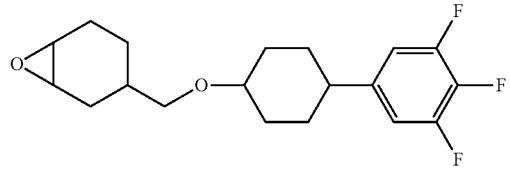
(1-4-24)
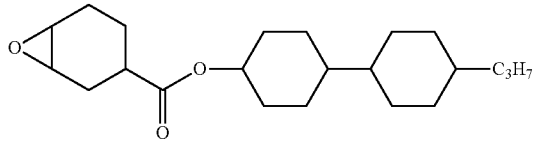
(1-4-25)
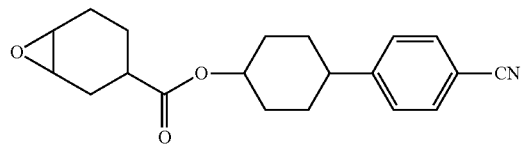
(1-4-26)
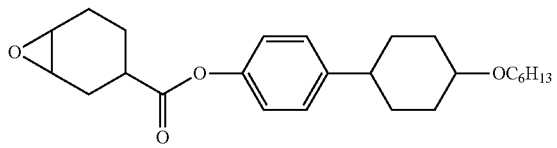
(1-4-27)
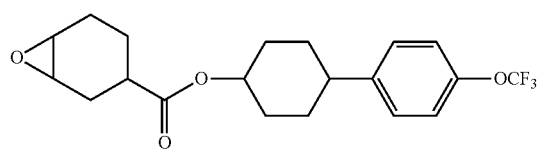
(1-4-28)
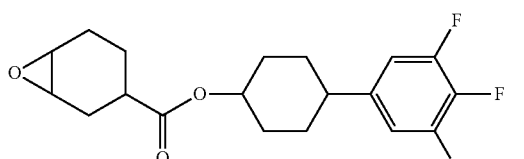
(1-4-29)
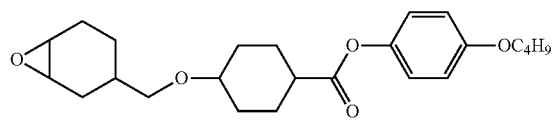
(1-4-30)
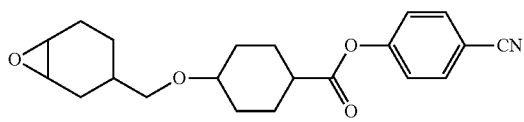
(1-4-31)
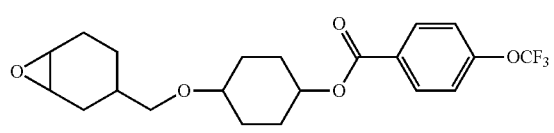
(1-4-32)
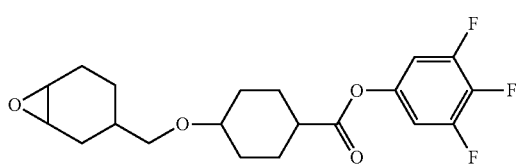

-continued

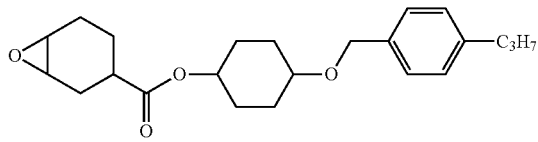
(1-4-33)

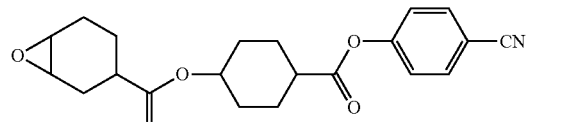
(1-4-34)

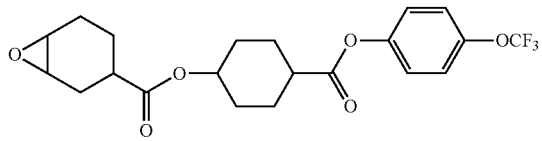
(1-4-35)

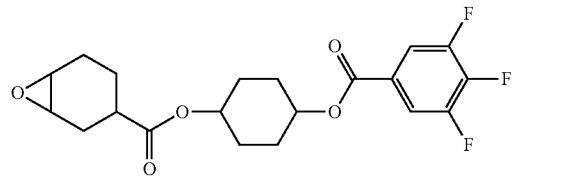
(1-4-36)

Next, the polymerizable liquid crystal composition of the invention will be explained. The composition of the invention includes at least one of the compound (1). The composition of the invention may include at least one of the compound (1) and at least one compound selected from the group of compounds represented by formula (M1) and formula (M2). The compound (M1) has the ability to exhibit a wide range of a liquid crystal phase and also can form a three-dimensional network, because it has two polymerizable groups in its structure, and they make it possible to form a polymer having a high mechanical strength. Since the compound (M2) has one polymerizable group, and an adjustment of orientation in a liquid crystal state can be attained, since it has a substituent such as a polar group at the opposite side of the polymerizable group in the major axis direction of the molecules. In any one of the compound (M1) and the compound (M2), a compound in which the ring $A^3$ is 1,4-phenylene gives a composition having a high optical anisotropy (Δn), and a compound in which the ring $A^3$ is naphthalene-2,6-diyl or fluorene-2,7-diyl gives a composition having an even higher optical anisotropy, and a compound in which the ring $A^3$ is 1,4-cyclohexylene gives a composition having a low optical anisotropy.

Desirable examples of the compounds (M1) and (M2) include the following compounds.

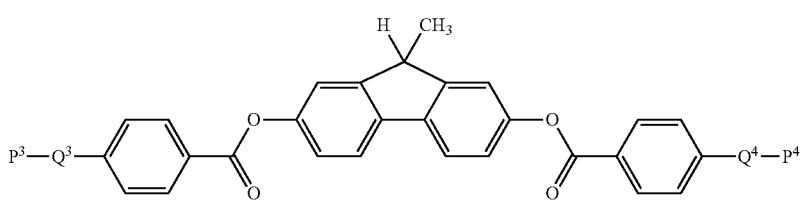
(M1-1)

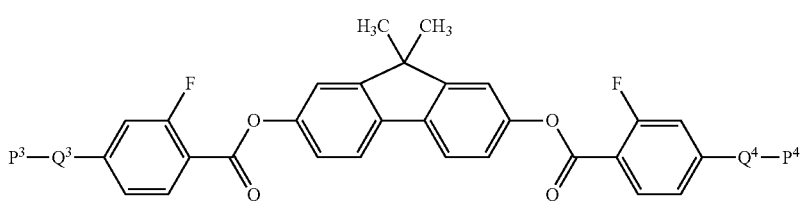
(M1-2)

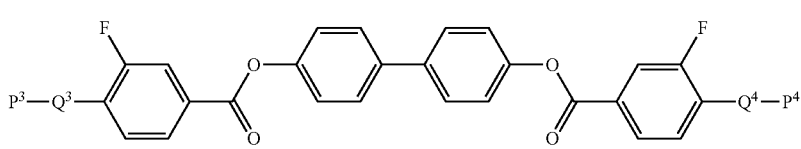
(M1-3)

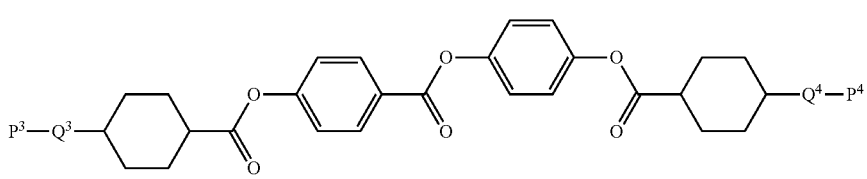
(M1-4)

-continued
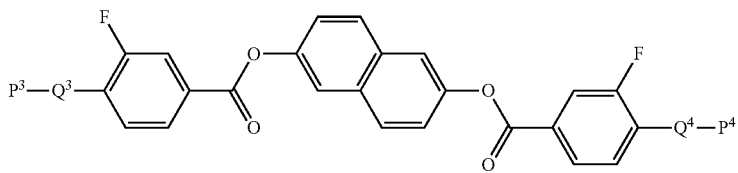 (M1-5)
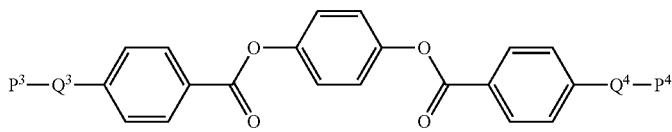 (M1-6)
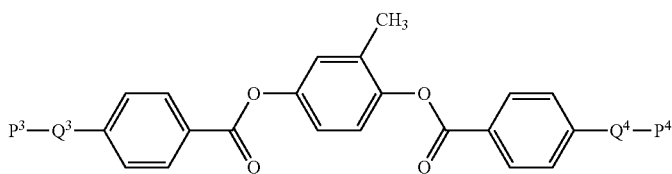 (M1-7)
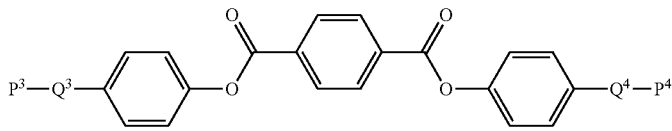 (M1-8)
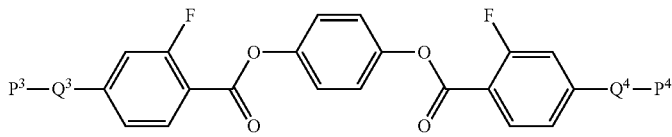 (M1-9)
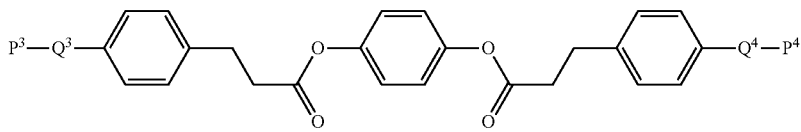 (M1-10)
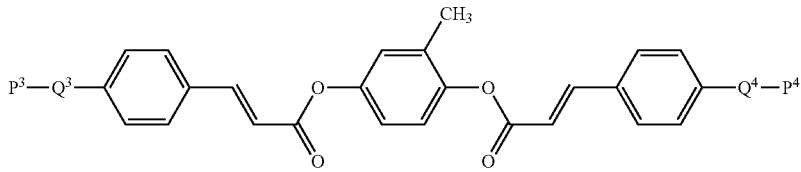 (M1-11)
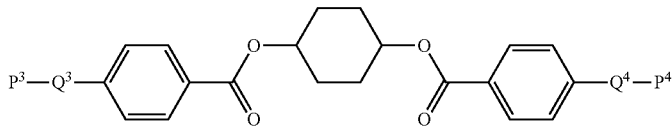 (M1-12)
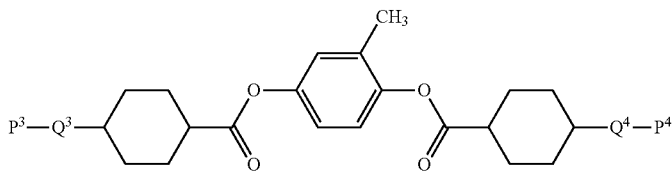 (M1-13)
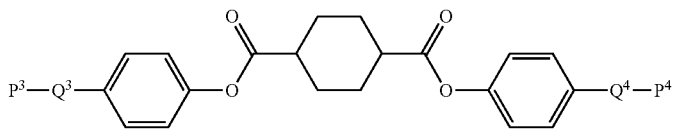 (M1-14)

-continued
(M1-15) 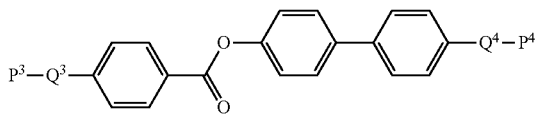
(M1-16) 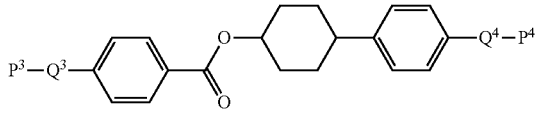
(M1-17) 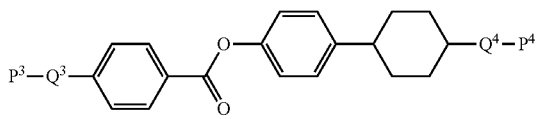
(M1-18) 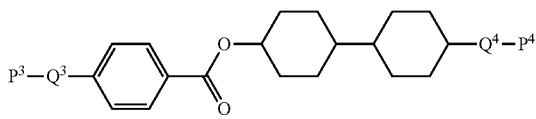
(M1-19) 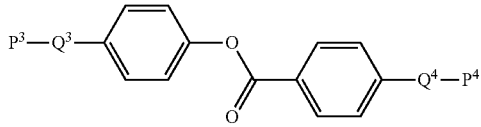
(M1-20) 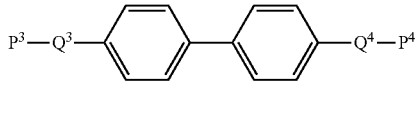
(M1-21) 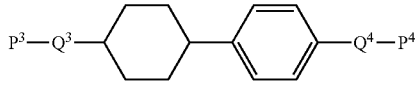
(M1-22) 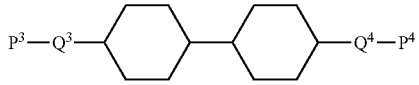
(M2-1) 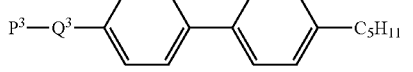
(M2-2) 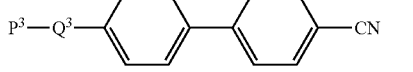
(M2-3) 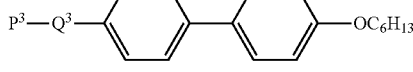
(M2-4) 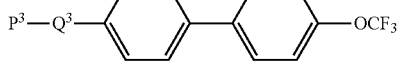
(M2-5) 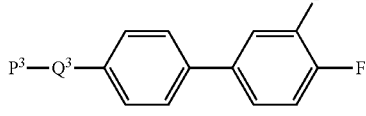
(M2-6) 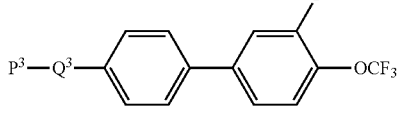
(M2-7) 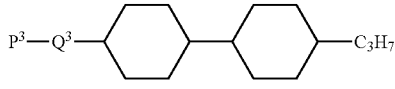
(M2-8) 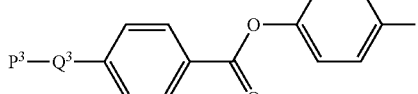
(M2-9) 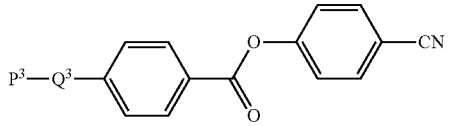
(M2-10) 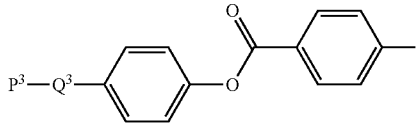
(M2-11) 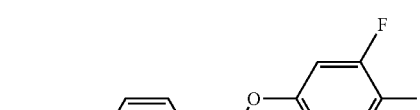
(M2-12) 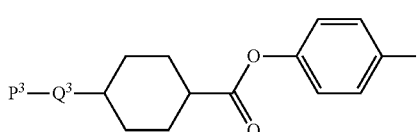
(M2-13) 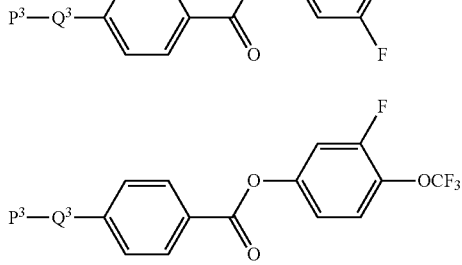

In these compounds, $Q^3$ and $Q^4$ have the same meanings with those in formula (M1) and formula (M2) described above, and $P^3$ and $P^4$ are each independently a group represented by any one of formula (2-2) to formula (2-4).

In the following explanation, the compound (M1) and the compound (M2) may be generically referred to as the compound (M). The polymerizable liquid crystal composition of the invention includes at least one of the compound (1). The polymerizable liquid crystal composition of the invention may include at least one of the compound (1) and at least one of the compound (M), as described above. A desirable ratio of the compound (1) in the polymerizable liquid crystal composition of the invention is in the range of approximately 5% to approximately 95% by weight based on the total amount of the compound (1) and the compound (M). A more desirable ratio is in the range of approximately 10% to approximately 90% by weight, and an even more desirable ratio is in the range of approximately 30% to approximately 80% by weight, and an especially desirable ratio is in the range of approximately 40% to approximately 70% by weight. A desirable ratio of the compound (M) is in the range of approximately 5% to approximately 95% by weight based on the total amount of the compound (1) and the compound (M). A more desirable ratio is in the range of approximately 10% to approximately 90% by weight, and an even more desirable ratio is in the range of approximately 20% to approximately 70% by weight, and an especially desirable ratio is in the range of approximately 30% to approximately 60% by weight.

The polymerizable liquid crystal composition of the invention includes the compound (1) and the compound (M), and the composition may further include another polymerizable compound. The polymerizable liquid crystal compound may include a non-polymerizable compound, an additive, a solvent and so forth. An example of the non-polymerizable liquid crystal compound is compounds listed in LiqCryst (LCI Publisher GmbH, Hamburg, Germany) that is a database of liquid crystal compounds. An example of the additive includes a nonionic surfactant, a cationic photopolymerization initiator, a photo-radical polymerization initiator, a hardener and a photosensitizer.

The non-polymerizable liquid crystal compound includes compounds represented by the following formula (A).

In formula (A), the meanings of $A^4$ and n are the same with those in formula (M1) described before, $Z^4$ is independently a single bond or alkylene having 1 to 10 carbons, and the alkylene, arbitrary —CH$_2$— may be replaced by —O—, —CO—, —COO—, —OCO—, —CH=CH—, —CF=CF— or —C≡C—, arbitrary hydrogen may be replaced by halogen, $R^4$ is alkyl having 1 to 10 carbons, alkenyl having 2 to 10 carbons, alkoxy having 1 to 10 carbons, hydrogen, chlorine, fluorine, —CM, —CF$_3$ or —OCF$_3$. Specific examples are as follows.

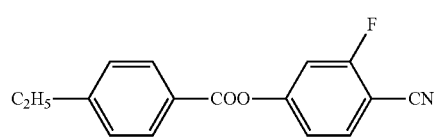

(LC-1)

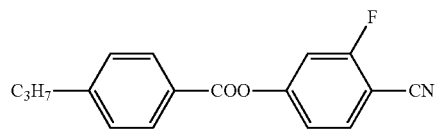

(LC-2)

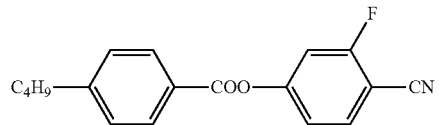

(LC-3)

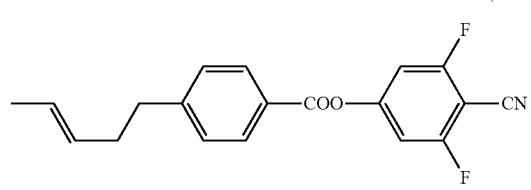

(LC-4)

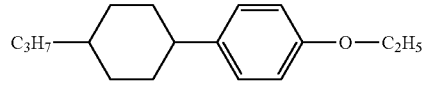

(LC-5)

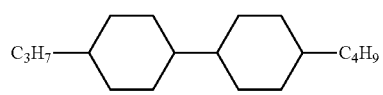

(LC-6)

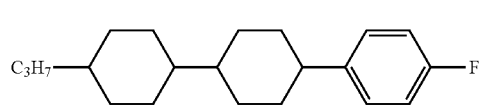

(LC-7)

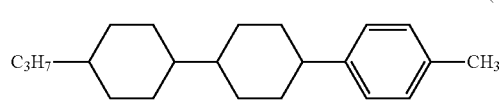

(LC-8)

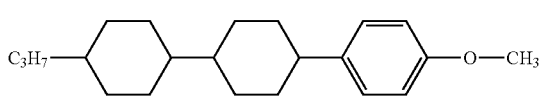

(LC-9)

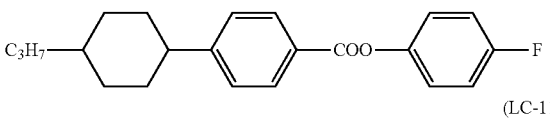

(LC-10)

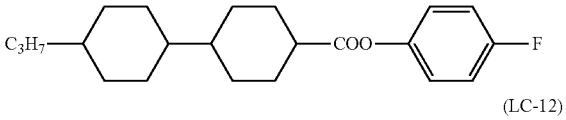

(LC-11)

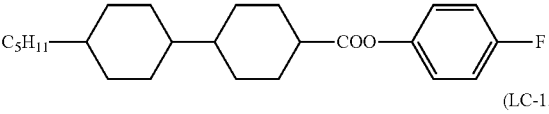

(LC-12)

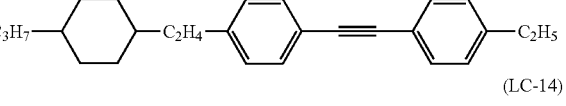

(LC-13)

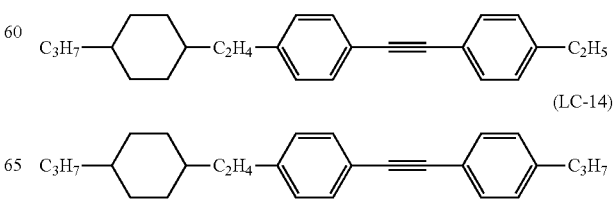

(LC-14)

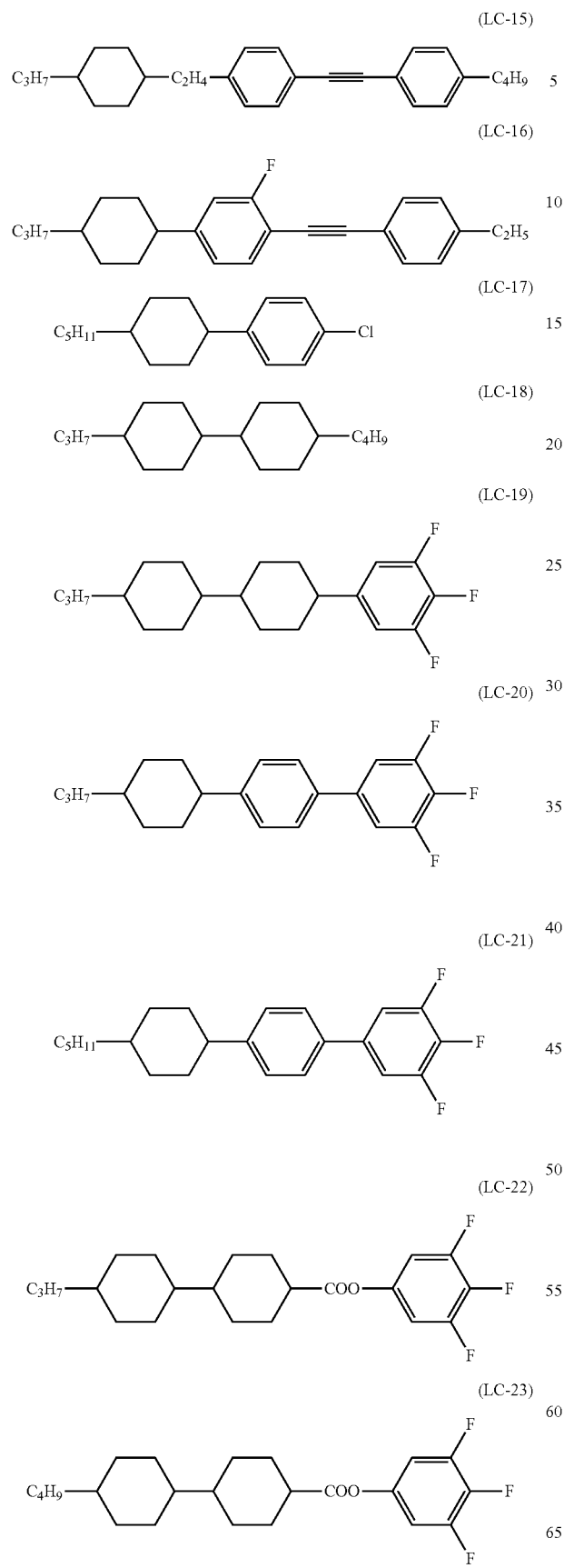
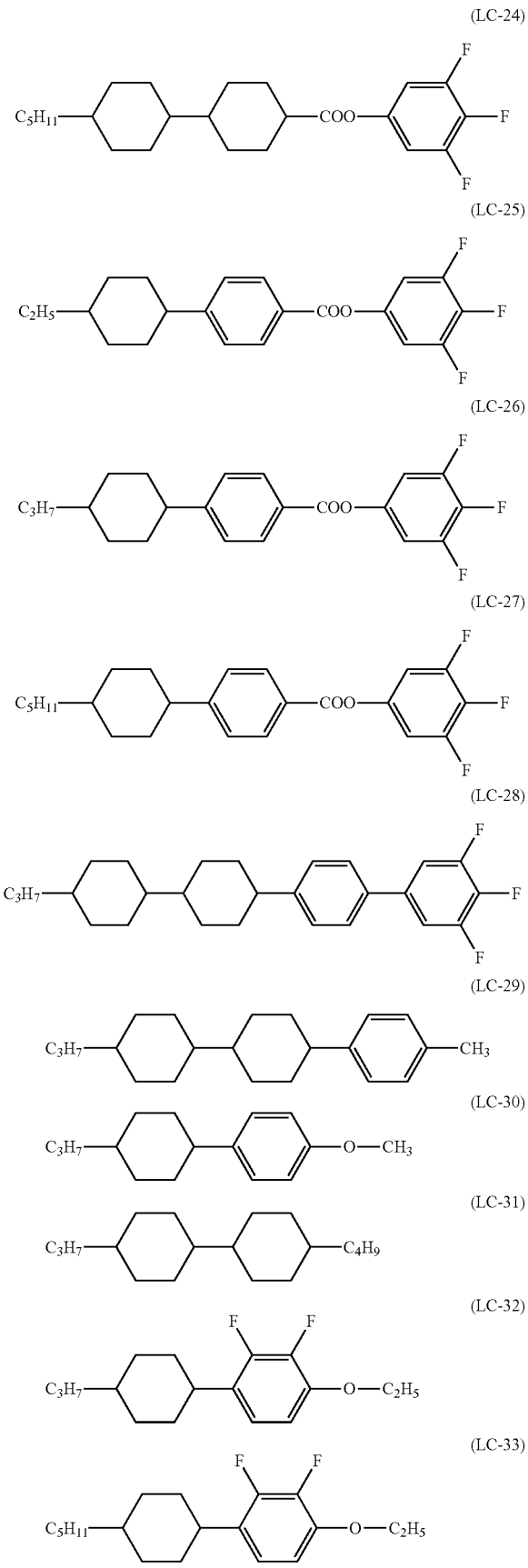

-continued

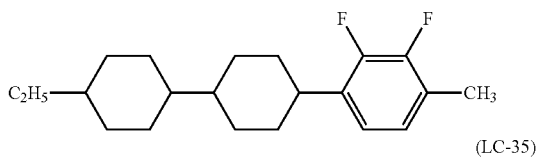
(LC-34)

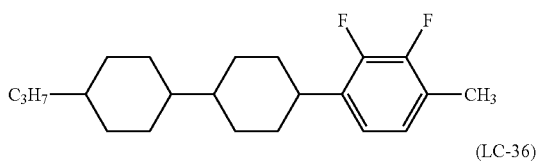
(LC-35)

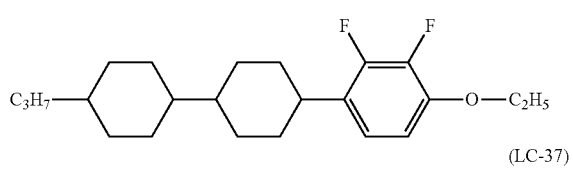
(LC-36)

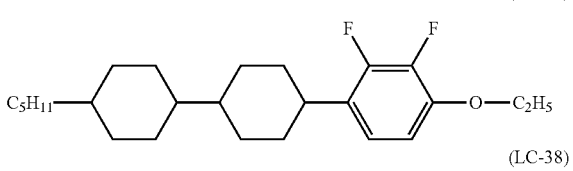
(LC-37)

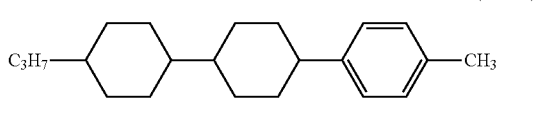
(LC-38)

Non-liquid crystal polymerizable compound can be added for the purpose of adjusting the ability to form a coat, mechanical strength or the like. A desirable example of the non-liquid crystal polymerizable compound includes (meth) acrylate compounds, vinyl compounds, styrene compounds, vinyl ether compounds, allyl ether compounds, epoxy compounds and oxetane compounds.

A desirable example of the non-liquid crystal polymerizable compound includes methyl(meth)acrylate, ethyl(meth) acrylate, butyl(meth)acrylate, 2-ethylhexyl(meth)acrylate, phenyl(meth)acrylate, vinyl chloride, vinyl fluoride, vinyl acetate, vinyl pivalate, vinyl 2,2-dimethylbutanoate, vinyl 2,2-dimethylpentanoate, vinyl 2-methyl-2-butanoate, vinyl propionate, vinyl stearate, vinyl 2-ethyl-2-methylbutanoate, N-vinylacetoamide, vinyl p-t-butylbenzoate, vinyl N,N-dimethylaminobenzoate, vinyl benzoate, stylene, o-, m- or p-chloromethylstylene, α-methylstylene, tetrafluoroethylene and hexafluoropropene, and further includes ethyl vinyl ether, hydroxybutyl monovinyl ether, t-amyl vinyl ether, cyclohexanedimethanol methyl vinyl ether, hydroxybutyl allyl ether, glycerol monoallyl ether and allyl glycidyl ether. 3-Ethyl-3-hydroxymethyloxetane, 3-methyl-3-hydroxymethyloxetane, bis[(1-ethyl-3-oxetanyl)methyl]ether or 3-ethyl-3-(2-ethylhexyloxymethyl) oxetane may also added for the purpose of adjusting the viscosity of the composition or avoiding shrinkage caused by curing.

A polyfunctional acrylate can be added to the composition for further increasing the ability to form a coat. A desirable polyfunctional acrylate includes 1,4-butanedioldiacrylate, 1,6-hexanedioldiacrylate, 1,9-nonanedioldiacrylate, neopentyl glycol diacrylate, triethylene glycol diacrylate, dipropylene glycol diacrylate, tripropylene glycol diacrylate, tetraethylene glycol diacrylate, trimethylolpropane triacrylate, ethylene oxide modified trimethylolpropane triacrylate, pentaerythritol triacrylate, tris(acryloyloxyethy)phosphate, ethylene oxide modified bisphenol A diacrylate, bisphenol A glycidyl diacrylate (trade name: Viscoat #700 available from Osaka Organic Chemical Industry Ltd.) and polyethylene glycol diacrylate.

A compound having a polyfunctional cationic polymerizable group can also be added to the composition for increasing the ability to form a coat. A desirable example of the compound includes the following compounds (5-1) to (5-9). The compound may be added to the polymerizable liquid crystal composition of the invention for adjusting the viscosity, adjusting the alignment, or increasing the hardness of the polymer.

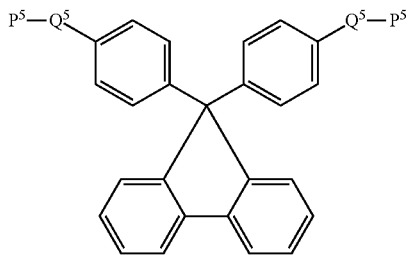
(5-1)

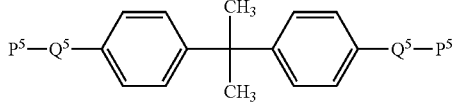
(5-2)

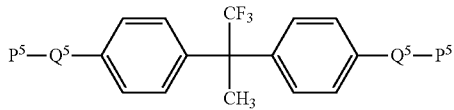
(5-3)

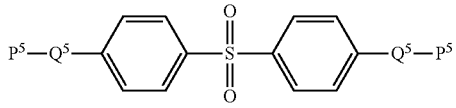
(5-4)

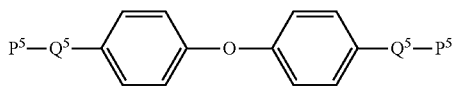
(5-5)

-continued

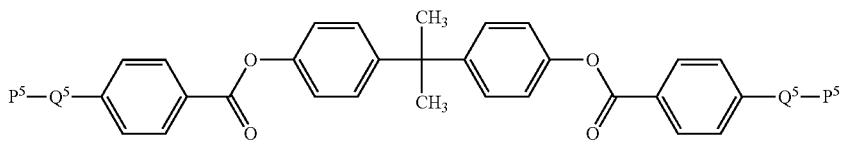
(5-6)

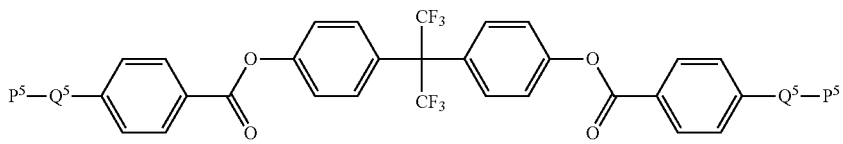
(5-7)

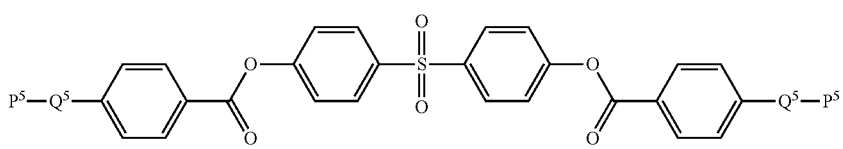
(5-8)

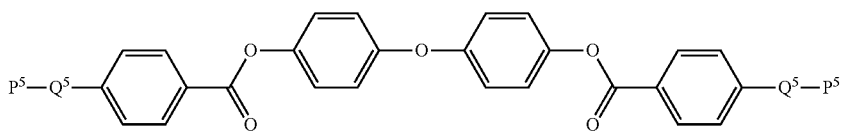
(5-9)

In these compounds, $Q^5$ is independently alkylene having 2 to 20 carbons, and in the alkylene arbitrary hydrogen may be replaced by fluorine or chlorine and arbitrary —$CH_2$— may be replaced by —O—, —COO—, —OCO—, —CH=CH— or —C≡C—; and $P^5$ is independently a group represented by any one of formula (2-2) to formula (2-4) as described above.

An example of another polymerizable compound includes an epoxy-type compound having one polymerizable group and an epoxy-type compound having two or more polymerizable groups. An example of epoxy resins that may be added to the composition includes, but is not limited to, epoxy resins that can be derived from divalent phenols, such as bisphenol A-type epoxy resins, bisphenol F-type epoxy resins, bisphenol S-type epoxy resins, bisphenol AD-type epoxy resins, resorcinol-type epoxy resins, hydroquinone-type epoxy resins, catechol-type epoxy resins, dihydroxynaphthalene-type epoxy resins, biphenyl-type epoxy resins and tetramethylbiphenyl-type epoxy resins; epoxy resins that can be derived from trivalent or polyvalent phenols, such as phenol novolactype epoxy resins, cresol novolac-type epoxy resins, triphenylmethane-type epoxy resins, tetraphenylethane-type epoxy resins, dicyclopentadiene-phenol modified epoxy resins, phenol aralkyl-type epoxy resins, biphenyl aralkyl-type epoxy resins, naphthol novolac-type epoxy resins, naphthol aralkyl-type epoxy resins, naphthol-phenol cocondensated novolac-type epoxy resins, naphthol-cresol cocondensated novolac-type epoxy resins, aromatic hydrocarbon formaldehyde resin-modified phenol resin-type epoxy resins and biphenyl-modified novolac-type epoxy resins; tetrabromobisphenol A-type epoxy resins, brominated phenol novolactype epoxy resins, polycarboxylic acid polyglycidyl ester, polyol polyglycidyl ether, aliphatic acid-type epoxy resins, alicyclic epoxy resins, glycidylamine-type epoxy resins, triphenolmethane-type epoxy resins and dihydroxybenzene-type epoxy resins. These epoxy compounds may be solely used or two or more epoxy resins may be mixed.

A specific example of epoxy-type compounds includes, alkyl monoglycidyl ether having 2 to 25 carbons (for example, butyl glycidyl ether, 2-ethylhexyl glycidyl ether, decyl glycidyl ether, stearyl glycidyl ether), butanediol diglycidyl ether, 1,6-hexanediol diglycidyl ether, neopentylglycol diglycidyl ether, dodecanediol diglycidyl ether, pentaerythritol polyglycidyl ether, trimethylolpropane polyglycidyl ether, glycerol polyglycidyl ether, phenyl glycidyl ether, p-sec-butylphenyl glycidyl ether, p-tert-butylphenyl glycidyl ether, resorcinol glycidyl ether, allyl glycidyl ether, tetrafluoropropyl glycidyl ether, octafluoropropyl glycidyl ether, dodecafluoropentyl glycidyl ether, stylene oxide, 1,7-octadiene diepoxide, limonene diepoxide, limonene monoxide, α-pinene epoxide, β-pinene epoxide, cyclohexene epoxide, cyclooctene epoxide, vinylcyclohexene oxide, butoxy polyethylene glycol glycidyl ether, polyethylene glycol diglycidyl ether, 3,4-epoxycyclohexenylmethyl-3',4'-epoxycyclohexene carboxylate, 3,4-epoxycyclohexenylethyl-3',4'-epoxycyclohexene carboxylate, 1,2-epoxy-4-vinylcyclohexane, vinylcyclohexene dioxide, allylcyclohexene dioxide, 1-epoxyethyl-3,4-epoxycyclohexane, 3,4-epoxy-4-methylcyclohexyl-2-propylene oxide, bis (3,4-epoxycyclohexyl)ether, bis(3,4-epoxycyclohexylmethyl) adipate, diglycidyl phthalate, diglycidyl terephthalate, diglycidyl hexahydrophthalate, diglycidyl tetrahydrophthalate, tris(2,3-epoxypropyl)isocyanurate, 3-ethyl-3-hydroxymethyloxetane, 3-ethyl-3-(phenoxymethyl)oxetane, bis[(1-ethyl-3-oxetanyl)methyl]ether, 3-ethyl-3-hydroxymethyloxetane, 3-methyl-3-hydroxymethyloxetane, and 3-ethyl-3-(2-ethylhexyloxymethyl) oxetane. A specific example further includes vinyl-type compounds such as ethyl vinyl ether, hydroxybutyl monovinyl ether, t-amyl vinyl ether and cyclohexanedimethanol methyl vinyl ether in addition to the epoxy-type compounds described above.

A desirable example of a nonionic surfactant includes a fluorine-based nonionic surfactant, a silicone-based nonionic surfactant and a hydrocarbon-based nonionic surfactant. An example of the fluorine-based nonionic surfactant includes BYK-340, Ftergent 251, Ftergent 221MH, Ftergent 250, FTX-215M, FTX-218M, FTX-233M, FTX-245M, FTX-290M, FTX-209F, FTX-213F, Ftergent 222F, FTX-233F, FTX-245F, FTX-208G, FTX-218G, FTX-240G, FTX-206D, Ftergent 212D, FTX-218, FTX-220D, FTX-230D, FTX-240D, FTX-720C, FTX-740C, FTX-207S, FTX-211S, FTX- 2205, FTX-230S, KB-L82, KB-L85, KB-L97, KB-L109, KB-L110, KB-F2L, KB-F2M, KB-F 25, KB-F3M and KB-FaM.

An example of the silicone-based nonionic surfactant includes Polyflow ATF-2, Glanol 100, Glanol 115, Glanol 400, Glanol 410, Glanol 435, Glanol 440, Glanol 450, Glanol B-1484, Polyflow KL-250, Polyflow KL-260, Polyflow KL-270, Polyflow KL-280, BYK-300, BYK-302, BYK-306, BYK-307, BYK-310, BYK-315, BYK-320, BYK-322, BYK-323, BYK-325, BYK-330, BYK-331, BYK-333, BYK-337, BYK-341, BYK-344, BYK-345, BYK-346, BYK-347, BYK-348, BYK-370, BYK-375, BYK-377, BYK-378, BYK-3500, BYK-3510 and BYK-3570. An example of the hydrocarbon-based nonionic surfactant includes Polyflow No. 3, Polyflow No. 50EHF, Polyflow No. 54N, Polyflow No. 75, Polyflow No. 77, Polyflow No. 85HF, Polyflow No. 90, Polyflow No. 95, BYK-350, BYK-352, BYK-354, BYK-355, BYK-358N, BYK-361N, BYK-380N, BYK-381, BYK-392 and BYK-Silclean3700, where the main component is an acryl-type polymer.

Incidentally, both Polyflow and Glanol described above are trade names of the products available from Kyoeisha Chemical Co., Ltd. BYK is a trade name of the product available from BYK Additives & Instruments. Ftergent, FTX and KB are trade names of the products available from Neos Company Limited.

A surfactant other than the types described above may be used as required. A specific example includes a variety of compounds such as polyether-type compounds, acrylic acid copolymer-type compounds, titanate-type compounds, imidazoline, tertiary ammonium salts, alkylamine oxides, polyamine derivatives, polyoxyethylene-polyoxypropylene condensates, polyethylene glycol and its esters, sodium lauryl sulfate, ammonium lauryl sulfate, amine lauryl sulfates, alkyl-substituted aromatic sulfonates, alkyl phosphates, aliphatic or aromatic sulfonate formaldehyde condensates, lauryl amidopropyl betaine, lauryl aminoacetic acid betaine, polyethylene glycol aliphatic acid esters, polyoxyethylene alkylamines, perfluoroalkylsulfonic acid salts and perfluoroalkylcarboxylic acid salts. These surfactants are effective in facilitating application of the composition to a supporting substrate and so forth.

A cationic photopolymerization initiator may be added to the composition of the invention. The photopolymerization initiator includes diaryliodonium salts (hereinafter referred to as DAS) and triarylsulfonium salts (hereinafter referred to as TAS). An example of DAS includes diphenyliodonium tetrafluoroborate, diphenyliodonium hexafluorophosphonate, diphenyliodonium hexafluoroarsenate, diphenyliodonium trifluoromethanesulfonate, diphenyliodonium trifluoroacetate, diphenyliodonium p-toluenesulfonate, diphenyliodonium tetra(pentafluorophenyl)borate, 4-methoxyphenylphenyliodonium tetrafluoroborate, 4-methoxyphenylphenyliodonium hexafluorophosphonate, 4-methoxyphenylphenyliodonium hexafluoroarsenate, 4-methoxyphenylphenyliodonium trifluoromethanesulfonate, 4-methoxyphenylphenyliodonium trifluoroacetate, 4-methoxyphenylphenyliodonium p-toluenesulfonate, 4-methoxyphenylphenyliodonium diphenyliodonium tetra(pentafluorophenyl)borate, bis(4-tert-butylphenyl)iodonium diphenyliodonium tetrafluoroborate, bis(4-tert-butylphenyl) iodonium diphenyliodonium hexafluoroarsenate, bis(4-tert-butylphenyl)iodonium diphenyliodonium trifluoromethanesulfonate, bis(4-tert-butylphenyl) iodonium trifluoroacetate, bis(4-tert-butylphenyl)iodonium p-toluenesulfonate and bis (4-tert-butylphenyl) iodonium diphenyliodonium tetra(pentafluorophenyl)borate.

DAS can be sensitized by the addition of a photosensitizer such as thioxanthone, phenothiazine, chlorothioxanthone, xanthone, anthracene, diphenylanthracene and rubrene.

An example of TAS includes triphenylsulfonium tetrafluoroborate, triphenylsulfonium hexafluorophosphonate, triphenylsulfonium hexafluoroarsenate, triphenylsulfonium trifluoromethanesulfonate, triphenylsulfonium trifluoroacetate, triphenylsulfonium p-toluenesulfonate, triphenylsulfonium tetra(pentafluorophenyl)borate, 4-methoxyphenyldiphenylsulfonium tetrafluoroborate, 4-methoxyphenyldiphenylsulfonium hexafluorophosphonate, 4-methoxyphenyldiphenylsulfonium hexafluoroarsenate, 4-methoxyphenyldiphenylsulfonium trifluoromethanesulfonate, 4-methoxyphenyldiphenylsulfonium trifluoroacetate, 4-methoxyphenyldiphenylsulfonium p-toluenesulfonate, 4-methoxyphenyldiphenylsulfonium triphenylsulfonium tetra(pentafluorophenyl)borate, 4-phenylthiophenyldiphenylsulfonium tetrafluoroborate, 4-phenylthiophenyldiphenylsulfonium hexafluorophosphonate, 4-phenylthiophenyldiphenylsulfonium hexafluoroarsenate, 4-phenylthiophenyldiphenylsulfonium trifluoromethanesulfonate, 4-phenylthiophenyldiphenylsulfonium p-toluenesulfonate and 4-phenylthiophenyldiphenylsulfonium tetra(p-entafluorophenyl)borate.

A specific trade name of the cationic photopolymerization initiator includes Cyracure UVI-6990, Cyracure UVI-6974 and Cyracure UVI-6992 available from UCC; Adeka Optomer SP-150, SP-152, SP-170 and SP-172 available from Asahi Denka Kogyo K.K.; Photoinitiator 2074 available from Rhodia Japan Ltd.; Irgacure 250 available from Ciba Japan K. K.; UV-9380C available from GE silicones Inc.; and HS series and CPI series available from San-Apro Ltd, and also includes TPS-series, TAZ-series, DPI-series, BPI-series, MDS-series, DTS-series, SI-series, PI-series, NDI-series, PAI-series, NAI-series, NI-series, DAM-series, MBZ-series, PYR-series, DNB-series and NB-series available from Midori Kagaku Co., Ltd.

A hybrid curing system in which a cationic photopolymerization initiator is added to a radical photopolymerization initiator can be used for the composition of the invention. An example of the radical photopolymerization initiator includes Darocure 1173 (2-hydroxy-2-methyl-1-phenylpropan-1-one), Irgacure 184 (1-hydroxycyclohexyl phenyl ketone), Irgacure 651 (2,2-dimethoxy-1,2-diphenylethan-1-one), Irgacure 500, Irgacure 2959, Irgacure 907, Irgacure 369, Irgacure 1300, Irgacure 819, Irgacure 1700, Irgacure 1800, Irgacure 1850, Darocure 4265 and Irgacure 784 available from Ciba Japan K. K.

Another example of the radical photopolymerization initiator includes p-methoxyphenyl-2,4-bis(trichloromethyl)triazine, 2-(p-butoxystyryl)-5-trichloromethyl-1,3,4-oxadiazole, 9-phenylacridine, 9,10-benzphenazine, a mixture of benzophenone/Michler's ketone, a mixture of hexaarylbiimidazole/mercaptobenzimidazole, 1-(4-isopropylphenyl)-2-hydroxy-2-methylpropan-1-one, benzyldimethylketal, 2-methyl-1-[4-(methylthio)phenyl]-2-morphorinopropan-1-one, a mixture of 2,4-diethylxanthone/methyl p-dimethylaminobenzoate and a mixture of benzophenone/methyltriethanolamine.

A thermal polymerization initiator may be used in the invention. An example of a specific trade name includes San-Aid SI-60, SI-80, SI-100, SI-110, SI-145, SI-150, SI-160 and SI-180 (these are a main agent), and San-Aid SI (an auxiliary agent) available from Sanshin Chemical Industry Co., Ltd. The initiator may be used together with a radical photopolymerization-initiator and a cationic photopolymerization initiator, or together with a radical photopolymerization initiator.

The polymerizable liquid crystal composition of the invention may include a hardener. Examples of the hardener include an acidic or basic compound having a group such as amino, carboxyl or mercapt, and a compound having a phenol moiety or an acid anhydride moiety. A more desirable hardener is a basic compound having an amino group, a compound having a phenol moiety and a compound having an acid anhydride moiety. These compounds may be used with a cationic photopolymerization initiator or a photo-radical polymerization initiator.

Examples of the hardener having an amino group include diethylenetriamine, triethylenetetraamine, tetraethylenepentamine, m-xylenediamine, trimethylhexamethylenediamine, 2-methylpentamethylenediamine, diethylaminopropylamine, isophoronediamine, 1,3-bisaminomethylcyclohexane, bis(4-aminocyclohexyl) methane, norbornenediamine, 1,2-diaminocyclohexane, laromin, diaminodiphenylmethane, methaphenylenediamine, diaminodiphenylsulfone, polyoxypropylenediamine, polyoxypropylenetriamine, polycyclohexylpolyamine mixture and N-aminoethylpyperadine.

Examples of the hardener of a phenol moiety include phenol novolac, xylylene novolac, bisphenol A novolac, triphenylmethane novolac, biphenyl novolac, dicyclopentadiene phenol novolac and terpene phenol novolac.

Examples of the hardener of an acid anhydride moiety include tetrahydrophthalic anhydride, hexahydrophthalic anhydride, methyltetrahydrophthalic anhydride, methylhexahydrophthalic anhydride, nadic methyl anhydride, hydrogenated nadic methyl anhydride, trialkyltetrahydrophthalic anhydride, methylcyclohexene tetracarboxylic anhydride, phthalic anhydride, trimellitic anhydride, pyromellitic anhydride, benzophenonetetracarboxylic dianhydride, ethylene glycol bis(anhydro-trimellitate), glycerin bis(anhydro-trimellitate) monoacetate, dodecenyl succinic anhydride, polyanhydrides of aliphatic dibasic acid and chlorendic anhydride.

The polymerizable liquid crystal composition of the invention may include a photosensitizer. An example of the photosensitizer includes thioxanetone derivatives, anthraquinone derivatives and naphthoquinone derivatives. A desirable example of the photosensitizer includes the following compounds (Z-1) to (Z-6). An especially desirable example of the photosensitizer includes the compound (Z-1) and the compound (Z-2). The photosensitizer can be used solely or in combination of two or more of them.

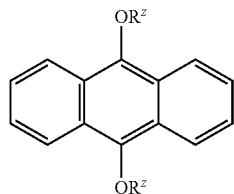

(Z-1)

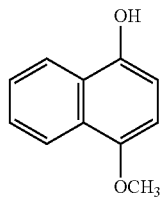

(Z-2)

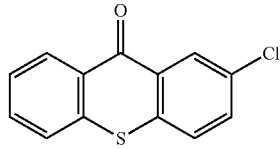

(Z-3)

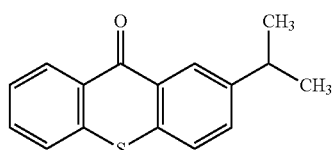

(Z-4)

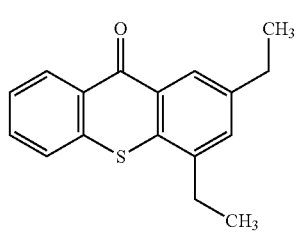

(Z-5)

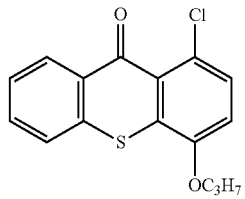

(Z-6)

In these formulas, $R^z$ is independently straight-chain alkyl having 1 to 10 carbons.

The compound (Z-1) where $R^z$ is n-butyl is available from Kawasaki Kasei Chemicals Ltd. in the trade name of Anthracure UVS-1331. The compound (Z-2) is available from Kawasaki Kasei Chemicals Ltd. in the trade name of Anthracure ET-2111. The compound (Z-3) is available from Lambson Ltd. in the trade name of Speedcure CTX. The compound (Z-4) is available from Shell Chemical Co. in the trade name of Quantacure ITX. The compound (Z-5) is available from Nippon Kayaku Co., Ltd. in the trade name of Kayacure DETX-S. The compound (Z-6) is available from Lambson Ltd. in the name of Speedcure CPTX.

A combination of DAS and a photosensitizer increases sensitivity to light. A desirable mixing ratio of the photosensitizer is in the rage of approximately 10 to approximately 200 weight parts based on 100 weight parts of DAS. A more desirable mixing ratio is in the range of approximately 20 to approximately 100 weight parts based on 100 weight parts of DAS. An ultraviolet absorber, a light stabilizer (a radical scavenger), an antioxidant or the like may be added for further increasing weather resistance of the polymerizable liquid crystal composition. An example of the ultraviolet absorber includes Tinuvin PS, Tinuvin P, Tinuvin 99-2, Tinuvin 109, Tinuvin 213, Tinuvin 234, Tinuvin 326, Tinuvin 328, Tinuvin 329, Tinuvin 384-2, Tinuvin 571, Tinuvin 900, Tinuvin 928, Tinuvin 1130, Tinuvin 400, Tinuvin 405, Tinuvin 460, Tinuvin 479, Tinuvin 5236, Adeka Stab LA-32, Adeka Stab LA-34, Adeka Stab LA-36, Adeka Stab LA-31, Adeka Stab 1413 and Adeka Stab LA-51. "Tinuvin" is a trade name of Ciba Japan K. K. and "Adeka Stab" is a trade name of Adeka Corporation.

An example of the light stabilizer includes Tinuvin 111FDL, Tinuvin 123, Tinuvin 144, Tinuvin 152, Tinuvin 292, Tinuvin 622, Tinuvin 770, Tinuvin 765, Tinuvin 780, Tinuvin 905, Tinuvin 5100, Tinuvin 5050, 5060, Tinuvin 5151, Chimassorb 119FL, Chimassorb 944FL, Chimassorb 944LD, Adeka Stab LA-52, Adeka Stab LA-57, Adeka Stab LA-62, Adeka Stab LA-67, Adeka Stab LA-63P, Adeka Stab LA-68LD, Adeka Stab LA-77, Adeka Stab LA-82 and Adeka Stab LA-87; Cyasorb UV-3346 available from Cytec Industries Inc.; and Goodrite UV-3034 available from Goodrich Corporation. "Chimassorb" is a trade name of Ciba Japan K. K.

An example of the antioxidant includes Adeka Stab AO-20, AO-30, AO-40, AO-50, AO-60 and AO-80 available from Adeka Corporation; Sumilizer BHT, Sumilizer BBM-S and Sumilizer GA-80 available from Sumitomo Chemical Co., Ltd.; and Irganox 1076, Irganox 1010, Irganox 3114 and Irganox 245 available from Ciba Japan K.K. These commercial products may be used.

The composition of the invention may be cured by use of base-amplifying reaction under irradiation with light (K. Arimitsu, M. Miyamoto, K. Ichimura, Angew. Chem. Int. Ed, 2000, 39, 3425).

The polymerizable liquid crystal composition of the invention may include a solvent, which is described above. Usually, the polymerizable liquid crystal composition is prepared by dissolving each component described above in a solvent. The polymerizable liquid crystal composition may be further diluted with a solvent to adjust the viscosity for an easy application. The solvent can be used solely or in combination of two or more of them. An example of a solvent includes ester-type solvents, amide-type solvents, alcohol-type solvents, ether-type solvents, glycol monoalkyl ether-type solvents, aromatic hydrocarbon-type solvents, halogenated aromatic hydrocarbon-type solvents, aliphatic hydrocarbon-type solvents, halogenated aliphatic hydrocarbon-type solvents, alicyclic hydrocarbon-type solvents, ketone-type solvents and acetate-type solvents.

A desirable example of the ester-type solvents includes alkyl acetates (for example, methyl acetate, ethyl acetate, propyl acetate, isopropyl acetate, butyl acetate, 3-methoxybutyl acetate, isobutyl acetate, pentyl acetate and isopentyl acetate), ethyl trifluoroacetate, alkyl propionate (for example, methyl propionate, methyl 3-methoxypropionate, ethyl propionate, propyl propionate and butyl propionate), alkyl butanoates (for example, methyl butanoate, ethyl butanoate, butyl butanoate, isobutyl butanoate and propyl butanoate), dialkyl malonates (for example, diethyl malonates), alkyl glycolates (for example, methyl glycolate and ethyl glycolate), alkyl lactates (for example, methyl lactate, ethyl lactate, isopropyl lactate, n-propyl lactate, butyl lactate and ethylhexyl lactate), monoacetin, γ-butyrolactone and γ-valerolactone.

A desirable example of the amide-type solvents includes N-methyl-2-pyroridone, N,N-dimethylacetamide, N-methylpropionamide, N,N-dimethylformamide, N,N-diethylformamide, N,N-diethylacetamide, N,N-dimethylacetamide dimethyl acetal, N-methylcaprolactam and dimethylimidazolidinone.

A desirable example of the alcohol-type solvents includes methanol, ethanol, 1-propanol, 2-propanol, 1-methoxy-2-propanol, t-butyl alcohol, sec-butyl alcohol, butanol, 2-ethylbutanol, n-hexanol, n-heptanol, n-octanol, 1-dodecanol, ethylhexanol, 3,5,5-trimethylhexanol, n-amyl alcohol, hexafluoro-2-propanol, glycerine, ethylene glycol, diethylene glycol, triethylene glycol, tetraethylene glycol, propylene glycol, dipropylene glycol, tripropylene glycol, hexylene glycol, 1,3-butanediol, 1,4-butanediol, 2,3-butanediol, 1,5-pentanediol, 2,4-pentanediol, 2,5-hexanediol, 3-methyl-3-methoxybutanol, cyclohexanol and methylcyclohexanol.

A desirable example of the ether-type solvents includes ethylene glycol dimethyl ether, diethylene glycol dimethyl ether, bis(2-propyl)ether, 1,4-dioxane and tetrahydrofuran (THF).

A desirable example of the glycol monoalkyl ether-type solvents includes ethylene glycol monoalkyl ethers (for example, ethylene glycol monomethyl ether and ethylene glycol monobutyl ether), diethylene glycol monoalkyl ethers (for example, diethylene glycol monoethyl ether), triethylene glycol monoalkyl ethers, propylene glycol monoalkyl ethers (for example, propylene glycol monobutyl ether), dipropylene glycol monoalkyl ethers (for example, dipropylene glycol monomethyl ether), ethylene glycol monoalkyl ether acetates (for example, ethylene glycol monobutyl ether acetate), diethylene glycol monoalkyl ether acetates (for example, diethylene glycol monoethyl ether acetate), triethylene glycol monoalkyl ether acetates, propylene glycol monoalkyl ether acetates (for example, propylene glycol monomethyl ether acetate, propylene glycol monoethyl ether acetate and propylene glycol monobutyl ether acetate), dipropylene glycol monoalkyl ether acetates (for example, dipropylene glycol monomethyl ether acetate) and diethylene glycol methyl ethyl ether.

A desirable example of the aromatic hydrocarbon-type solvents includes benzene, toluene, xylene, mesitylene, ethylbenzene, diethylbenzene, i-propylbenzene, n-propylbenzene, t-butylbenzene, s-butylbenzene, n-butylbenzene and tetraline. A desirable example of the halogenated aromatic hydrocarbon-type solvents includes chlorobenzene. A desirable example of the aliphatic hydrocarbon-type solvents includes hexane and heptane. A desirable example of the halogenated aliphatic hydrocarbon-type solvents includes chloroform, dichloromethane, carbon tetrachloride, dichloroethane, trichloroethylene and tetrachloroethylene. A desirable example of the alicyclic hydrocarbon-type solvents includes cyclohexane and decaline.

A desirable example of the ketone-type solvents includes acetone, methyl ethyl ketone, methyl isobutyl ketone, cyclohexanone, cyclopentanone and methyl propyl ketone.

A desirable example of the acetate-type solvents includes ethylene glycol monomethyl ether acetate, propylene glycol monomethyl ether acetate, propylene glycol monoethyl ether acetate, methyl acetoacetate and 1-methoxy-2-propyl acetate.

The amide-type solvents, the aromatic hydrocarbon-type solvents and the ketone-type solvents are desirable in view of the solubility of the polymerizable liquid crystal compound. The ester-type solvents, the alcohol-type solvents, the ether-type solvents and the glycol monoalkyl ether-type solvents are desirable in consideration of the boiling points of the solvents. Although selection of the solvent is not especially limited, it is necessary to decrease drying temperature in order to avoid deformation of a supporting substrate and to prevent erosion of the solvent to the supporting substrate when a plastic substrate is used as the supporting substrate. A desirable example of the solvent used in such cases includes the aromatic hydrocarbon-type solvents, the ketone-type solvents, the ester-type solvents, the ether-type solvents, the alcohol-type solvents, the acetate-type solvents and the glycol monoalkyl ether-type solvents. In such solvents, it is very important that solubility in a highly safe organic solvent is high. An example of the solvent is ethyl lactate, ethyl pyruvate, 2-heptanone, butyl acetate, methyl 3-methoxypropionate, methyl 3-ethoxypropionate and propylene glycol monoethyl ether acetate.

The ratio of the solvent in the polymerizable liquid crystal composition of the invention is in the range of 0% to approximately 95% by weight. A desirable ratio is in the range of approximately 40% to approximately 95% by weight in view of the solubility of the polymerizable liquid crystal compound and an optimum viscosity for applying the solution, and also in an economic view of the solvent cost, and the period of time and calorific values during evaporation of the solvent. A more desirable ratio is in the range of approximately 45% to approximately 90% by weight and an even more desirable ratio is in the range of approximately 50% to approximately 85% by weight.

In the polymerizable liquid crystal composition of the invention, factors determining orientation of liquid crystal molecules includes (1) the kinds of compounds included in the composition, (2) the kinds of a supporting substrate, and (3) the kinds of methods of alignment treatment. A desirable method of the alignment treatment includes oblique-deposition of silicon oxide and slit etching. An especially desirable method for alignment treatment includes rubbing treatment in which the surface is rubbed with a rayon cloth in one direction. In the rubbing treatment, a supporting substrate itself may be rubbed. A supporting substrate that is coated with a thin film of polyimide, polyvinyl alcohol or the like may be rubbed. A specific thin film on which an excellent alignment is possible without rubbing treatment is also known. A supporting substrate coated with a liquid crystal polymer having a side chain is also effective.

A classification of orientation in liquid crystal molecules includes homogeneous (parallel) orientation, homeotropic (perpendicular) orientation and hybrid orientation. The homogeneous orientation means the state in which the directors are parallel to a supporting substrate and are arranged in one direction. The homeotropic orientation means the state in which the directors are perpendicular to a supporting substrate. The hybrid orientation means the state in which the director are going to stand up, from a parallel direction to a perpendicular direction to the substrate as the distance from a substrate is increased. These orientations are observed in the composition having a nematic phase and so forth.

A film having a variety of optical characteristics can be formed by fixing orientation of liquid crystal molecules. The optical anisotropy of the film can be expressed as a indicatrix by three dimensional refractive index, where $n_x$, $n_y$ and $n_z$ are defined as x axis direction, y axis direction and z axis direction, respectively, and the z axis is in the thickness direction of the film and the x and y axes are in the right angle directions on the film plane. A polymer having homogeneous orientation is classified into an A-plate, in which the relationship of the three dimensional reflective index can be expressed as $n_x > n_y = n_z$, because a light axis is in the $n_x$ direction and the reflective index in the light axis direction is larger than that in the right angle direction. A polymer having homeotropic orientation is classified into a C-plate, in which the relationship of the three dimensional reflective index can be expressed as $n_x = n_y < n_z$, because the light axis is in the $n_z$ direction and the reflective index in the light axis direction is larger than that in the right angle direction. A polymer having hybrid orientation has optical characteristics of an O-plate. For example, the polymer can be applied to a viewing angle-compensation film for a twisted nematic (TN) mode device.

The polymerizable liquid crystal composition of the invention may include an optically active compound. The composition in which a suitable amount of an optically active compound has been added is applied to an aligned substrate and then is polymerized, giving an optical retardation plate having a helical structure (a twist structure). The helical structure is fixed by the polymerization of the compound (1). Characteristics of the formed body having optical anisotropy depend on a helical pitch in the helical structure formed. The length of the helical pitch can be adjusted by the kinds and the amount of the optically active compound. Only one optically active compound may be added, or a plurality of optically active compounds may be added for the purpose of compensating the temperature dependence of the helical pitch.

The selective reflection of visible light, which is the characteristics of the formed body having optical anisotropy described above, arises from the action of a helical structure on incident light, which leads to the reflection of circularly polarized light or elliptically polarized light. Characteristics of the selective reflection are expressed as a function of $\lambda = n \cdot \text{Pitch}$; where $\lambda$ stands for the central wavelength of selective reflection, n stands for an average refractive index of a formed body having optical anisotropy and Pitch stands for a helical pitch. Hence, $\lambda$, and its bandwidth ($\Delta\lambda$) can be suitably adjusted by the value of n or Pitch. When a helical pitch is 1/n of a wavelength of light, right- or left-circularly polarized light among light with the wavelength can be reflected according to Bragg's law, depending on the direction of the helix. This phenomenon can be utilized to, for example, a functional device that separates circularly polarized light. The direction of the helix depends on configuration of an optically active compound. A desired helical direction can be induced by a suitable selection of configuration of an optically active compound. For example, a formed body having optical anisotropy can be obtained in which a helical pitch changes consecutively in the thickness-direction of the formed body, according to the method disclosed in JP H06-281814 A (1994), and then it can reflect light with a wavelength range that depends on the pitch. The bandwidth $\Delta\lambda$ should be decreased for an improvement of color purity, and $\Delta\lambda$ should be increased for broadband reflection. Furthermore, the selective reflection is greatly affected by cell thickness. The cell thickness should not be made too small for maintaining color purity. The thickness should not be made too large for maintaining orientation uniformity. Thus, a suitable adjustment of the cell thickness is necessary, and a desirable cell thickness is in the range of approximately 0.5 μm to approximately 25 μm, and a more desirable thickness is in the range of approximately 0.5 μm to approximately 5 μm.

The negative-type C-plate (negative C-plate) described in W. H. de Jeu, Physical Properties of Liquid Crystalline Materials, Gordon and Breach, New York (1980) can be prepared by making the helical pitch shorter than the wavelengths of visible light. A shorter helical pitch can be achieved by use of an optically active compound having a large twisting power (HTP: helical twisting power) and by increasing the amount of the compound. The negative-type C-plate can be formed specifically when $\lambda$ is approximately 350 nm or less, and preferably approximately 200 nm or less. This negative-type C-plate serves as an optical compensation film suitable for a display device of a VAN-type, a VAC-type, an OCB-type or the like, among liquid crystal display devices.

Any optically active compound described above may be used if the optically active compound can induce a helical structure and can be mixed appropriately with the polymerizable liquid crystal composition as a base. The optically active compound may be polymerizable or non-polymerizable, and an optimum compound can be added in accordance with a purpose. The polymerizable compound is more suitable when heat resistance and solvent resistance are taken into consideration. An example of a skeleton which exhibits optical activity includes alkylene and alkenylene having one or more asymmetric carbons, or compounds having the following partial structures.

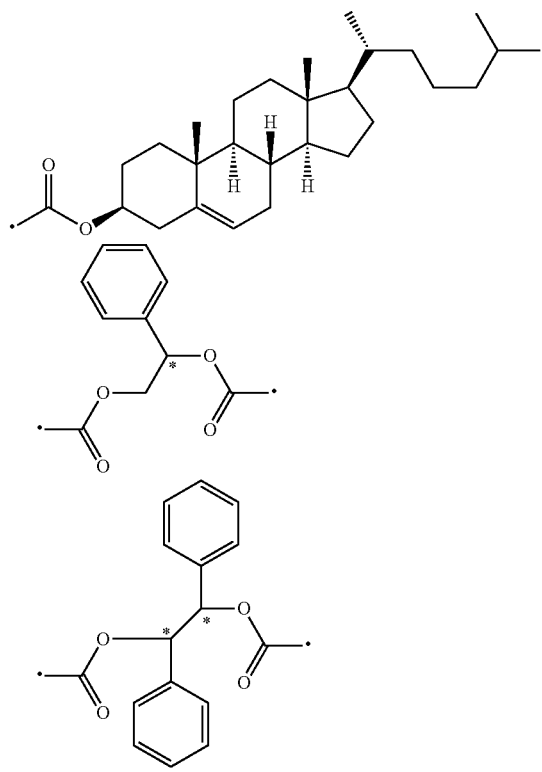

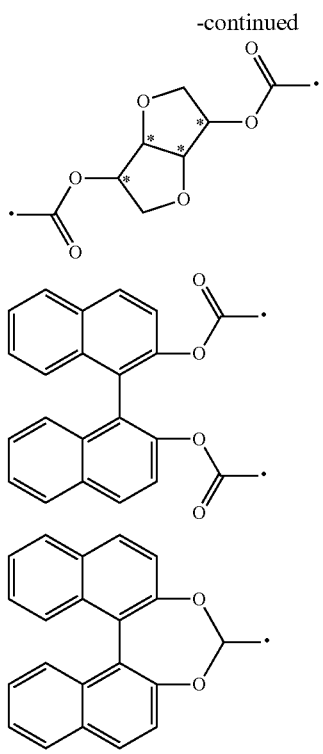

An optically active compound having a large twisting power (HTP: helical twisting power) among the compounds described above is suitable for decreasing the helical pitch. A representative example of a compound having a large twisting power is described in GB 2,298,202 A and DE 10,221,751 A1.

A more desirable example of a polymerizable compound having optical activity includes, but is not limited to, the following compounds.

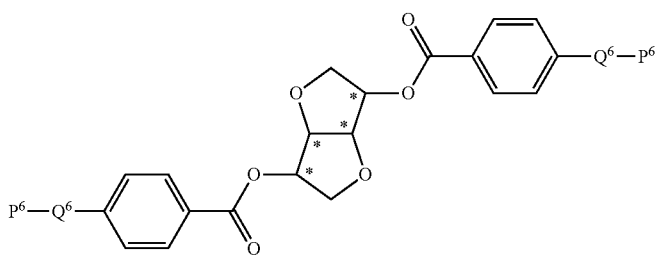

(6-1)

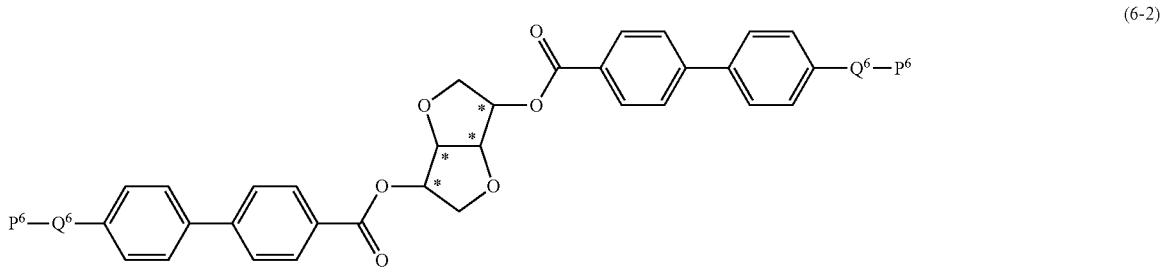

(6-2)

(6-3)
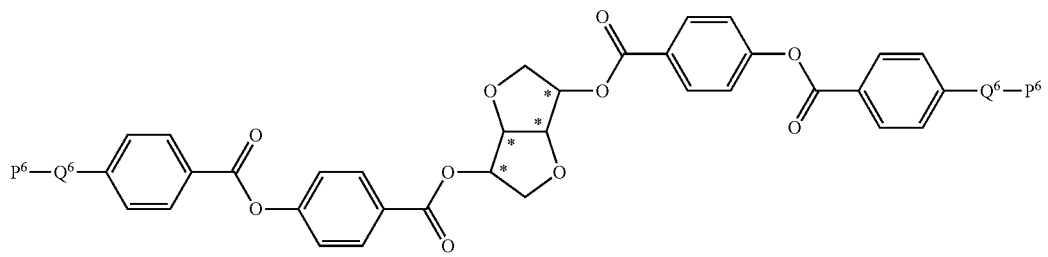
(6-4)
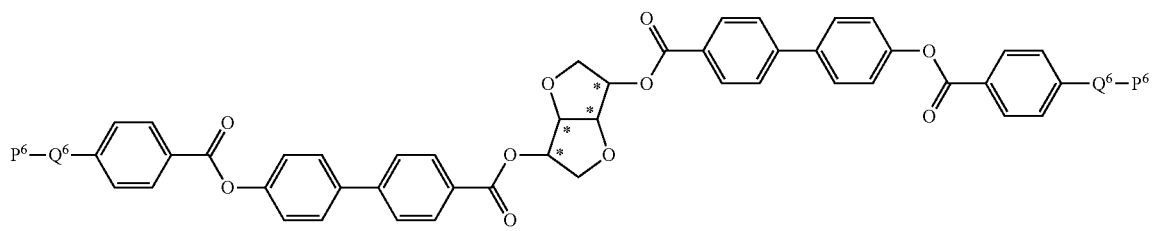
(6-5)
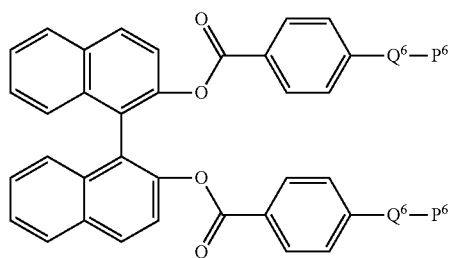
(6-6)
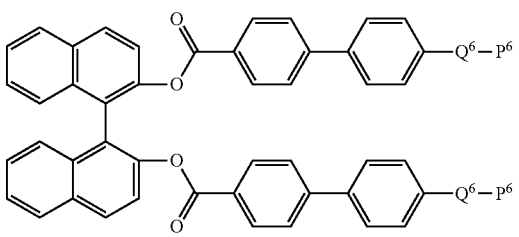
(6-7)
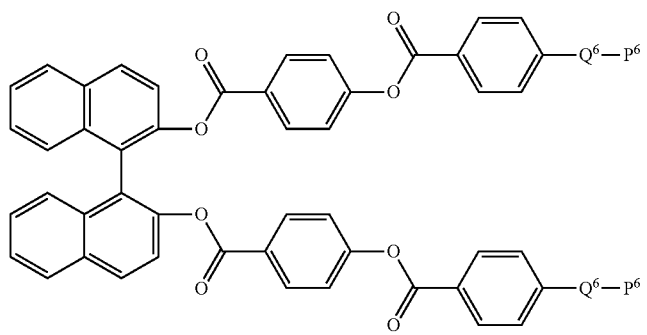
(6-8)
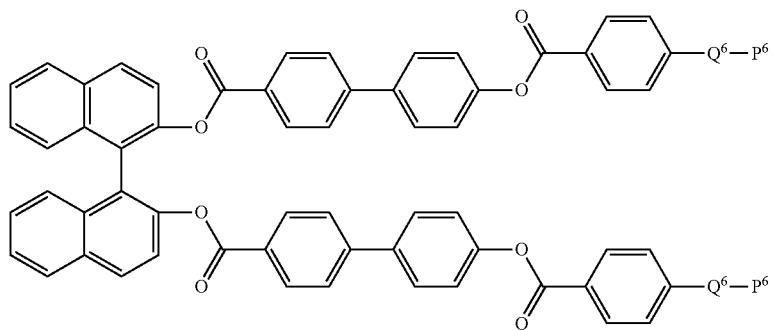

In these compounds, $Q^6$ is independently alkylene having 1 to 20 carbons, and in the alkylene arbitrary hydrogen may be replaced by fluorine and arbitrary —$CH_2$— may be replaced by —O—, —COO—, —OCO—, —CH=CH— or —C≡C—; and $P^6$ is independently a group represented by any one of formula (2-2) to formula (2-4) as described above.

Next, polymerization conditions of the composition in the invention will be explained. A polymer is formed by polymerization of the polymerizable liquid crystal composition of the invention. Polymerization in the presence of a photopolymerization catalyst is preferable to thermal polymerization when a polymer with an excellent orientation is desired. This is because the polymerization can be carried out readily under the conditions that the composition exhibits a liquid crystal state.

Desirable kinds of light used for photopolymerization include ultraviolet light, visible light and infrared light. Electromagnetic waves such as electron beams and X-rays may be used. Ultraviolet light and visible light are usually desirable. Desirable wavelengths are in the range of approximately 150 nm to approximately 500 nm. More desirable wavelengths are in the range of approximately 250 nm to approximately 450 nm and most desirable wavelengths are in the range of approximately 300 nm to approximately 400 nm. An example of a light source includes a low-pressure mercury lamp (a germicidal lamp, a chemical fluorescent lamp and a black light), a high-pressure discharge lamp (a high-pressure mercury lamp and a metal halide lamp) and a short-arc lamp (an ultra high-pressure mercury lamp, a xenon lamp and a mercury-xenon lamp). A desirable light source is a high-pressure mercury lamp. The composition may be irradiated directly with light from the light source. The composition may be irradiated with light of a specific wavelength (or specific range of wavelengths) selected by a filter. Desirable irradiation energy density is in the range of approximately 2 to approximately 5,000 mJ/cm$^2$. More desirable irradiation energy density is in the range of approximately 10 to approximately 3,000 mJ/cm$^2$. Most desirable irradiation energy density is in the range of approximately 100 to approximately 2,000 mJ/cm$^2$. Desirable illuminance is in the range of approximately 0.1 to approximately 5,000 mW/cm$^2$. More desirable illuminance is in the range of approximately 1 to approximately 2,000 mW/cm$^2$. Temperature on irradiation with light is set up in order that the composition exhibits a liquid crystal phase. A desirable temperature for illuminance is approximately 100° C. or lower. An excellent orientation may not be attained at approximately 100° C. or higher because of the possibility of thermal polymerization.

Next, the polymer of the invention will be explained. The polymer is formed by polymerization of the compound (1). A homopolymer is formed by polymerization of only one of the compound (1). The polymer has one polymer unit. A copolymer is formed when a composition including at least two of the compound (1) is polymerized. The copolymer has at least two polymer units. A cationic photopolymerization method is especially desirable for the production of a film having optical anisotropy that is a purpose of the invention, since polymerization under the conditions of oriented liquid crystals is desirable. The polymer that is formed by polymerization of the compound (1) satisfies a plurality of characteristics such that it is colorless and transparent, photoelasticity is small, it is hard to be peeled, it has a sufficient hardness, heat resistance is large, and weather resistance is large.

Usage of the polymer is as follows. The polymer can be used as a formed body having optical anisotropy. An example of the polymer includes an optical film such as an optical retardation plate (a ½ wave plate, a ¼ wave plate and so forth), an antireflection film, a selective reflection film and a viewing angle-compensation film. The polymer having an orientation such as homogeneous, hybrid, homeotropic or twist can be utilized for an optical retardation plate, a polarizer, a liquid crystal alignment film, an antireflection film, a selective reflection film, a viewing angle-compensation film, and so forth. Such a polymer is utilized for an optical retardation plate and a viewing angle-compensation film of a liquid crystal display device, for the purpose of optical compensation. An important use example in industry includes viewing angle-compensation in the liquid crystal display device with a mode of VA, IPS, TN or MVA.

Application of the polymer is as follows. The polymer can be utilized for epoxy resins having a high thermal conductivity, adhesives, synthetic polymers having mechanical anisotropy such as strength, a modulus of elasticity and an elongation percentage, cosmetics, an ornament, non-linear optical materials, information storage materials and so forth. A thermoplastic resin is utilized for these applications. The thermoplastic resin, which is a linear polymer with less branched chain, can be obtained by polymerization of the liquid crystal composition that mainly includes a monofunctional compound. The weight average molecular weight of the resin is in the range of approximately 500 to approximately 1,000,000, preferably in the range of approximately 1,000 to approximately 500,000, and more preferably approximately 5,000 to approximately 100,000.

An optical retardation plate, which is one of example of usage of the polymer, has a function that converts the state of polarized light. A ½ wave plate has a function in which the direction of oscillation in linearly polarized light is rotated 90 degrees. The composition applied to a supporting substrate so as to satisfy the equation of d=λ/2×Δn, wherein d is the thickness of the composition, λ is a wavelength and Δn is optical anisotropy. After the orientation of the composition, photopolymerization gives a ½ wave plate. On the other hand, a ¼ wave plate has a function in which linearly polarized light is converted to circularly polarized light or circularly polarized light is converted to linearly polarized light. In this case, the paint film of the composition may be prepared so as to satisfy the equation of d=λ/4×Δn. The thickness (d) of the polymer is adjusted as follows. A paint film having an objective thickness can be obtained by a suitable selection of the concentration of the composition, a method of application, conditions of application and so forth, when the composition is diluted with a solvent and then applied to a supporting substrate. A method that utilizes a liquid crystal cell is also desirable. The liquid crystal cell is convenient because it contains an alignment film such as polyimide. The thickness of a paint film can be adjusted by regulating the interval of a liquid crystal cell, when the composition is injected to the liquid crystal cell.

A patterned optical retardation plate can be provided by a combination of photopolymerization and thermal polymerization. After the polymerizable liquid crystal composition has been applied to a supporting substrate, and has been oriented, only a irradiated part is photopolymerized by irradiation with light passed through a photomask. Then, in an uncured part, orientation is disordered, and optical anisotropy is decreased or disappeared by the transition to an isotropic phase, when the polymer is heated. The patterned optical retardation plate can be prepared by the thermal polymerization of the uncured part.

The form of the polymer may be filmy, platy, granular, powdery and so forth. The polymer may be molded. A supporting substrate is generally employed to form a filmed polymer. The polymer film is obtained by application of the composition to the supporting substrate and then by polymerization of the paint film exhibiting a liquid crystal phase. A desirable thickness of the polymer depends on the value of optical anisotropy and usage of the polymer. A desirable thickness is in the range of approximately 0.05 to approximately 50 μm. A more desirable thickness is in the range of approximately 0.1 to approximately 20 μm. An especially desirable thickness is in the range of approximately 0.5 to approximately 10 μm. A haze value (cloudiness) of the polymer is generally approximately 1.5% or less. Transmissivity of the polymer is generally approximately 80% or more in the visible light range. Such a polymer is suitable for a thin film with optical anisotropy used for a liquid crystal display device.

An example of a supporting substrate includes triacetyl cellulose (may be referred to as TAC), polyvinyl alcohol, polyimide, polyester, polyarylate, polyetherimide, polyethylene terephthalate and polyethylene naphthalate. An example of the trade name includes "Afton" of JSR Corporation, "Zeonex" and "Zeonor" of Zeon Corporation and "Apel" of Mitsui Chemicals, Inc. The supporting substrate includes a uniaxially stretched film and a biaxially stretched film. A desirable supporting substrate is a triacetyl cellulose film. The film may be used without pre-treatment. The film may be processed by means of a surface-treatment as required, such as a saponification-treatment, a corona-treatment, an UV-ozone treatment and a plasma-treatment. An additional example includes a supporting substrate made of metal such as aluminum, iron and copper, and a supporting substrate made of glass such as alkali glass, borosilicate glass and flint glass.

A paint film on a supporting substrate is prepared by application of the composition as a neat liquid. The paint film is also prepared by dissolution of the composition in a suitable solvent and then by evaporation of the solvent. An application method includes spin coating, roll coating, curtain coating, flow coating, printing, micro-gravure coating, gravure coating, wire-bar coating, dip coating, spray coating, meniscus coating and casting film-forming.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention is explained by way of the following Examples, but not limited to Examples. The structures of compounds were characterized by means of their nuclear magnetic resonance spectra, infrared spectra, mass spectra and so forth. The transition temperature was expressed in the degree Celsius (° C.), and the symbols C and I stand for crystals and an isotropic liquid phase, respectively. A parenthesized value shows that the phase transition is monotropic. In Example, the symbol L represents the liter that is a unit of volume. Methods of measurement are as follows.

<Structural Determination of Compounds>

The structures of synthesized compounds were determined by means of a 500 MHz-proton NMR spectroscopy Bruker Model DRX-500. A unit of described values is ppm and symbols s, d, t and m stand for singlet, doublet, triplet and multiplet, respectively.

<Phase Transition Temperature>

A sample was placed on a hot plate of a melting point apparatus equipped with a polarizing microscope and heated at a rate of 3° C./minute. Temperature was measured when a liquid crystal phase was transformed to another liquid crystal phase. The symbols C, N and I stand for crystals, a nematic phase and isotropic liquid, respectively. A clearing point (NI-point) means the maximum temperature of a nematic phase or transition temperature from a nematic phase to isotropic liquid. "C 50 N 63 I" shows that crystals were transformed to a nematic phase at 50° C. and the nematic phase was transformed to isotropic liquid at 63° C.

<Orientation of Liquid Crystal Molecules>

A polymer film (a liquid crystal alignment film) was formed on a glass substrate having a rubbed polyimide alignment film. Orientation of the polymer was determined by visual observation in the following way based on the angle dependence of transmitted light intensity.

(1) Visual Observation:

A polymer film was placed between two polarizers that were arranged in the crossed Nicols and the film surface was irradiated with light vertically (the tilt angle was zero degrees). The change of transmitted light intensity was observed while the tilt angle of irradiation increased, for example, from zero degrees to 50 degrees. The tilted direction of irradiation was the same with that of the rubbing (a major axis direction of liquid crystal molecules). Orientation was determined to be homogeneous when transmitted light in the vertical direction was maximum. The polymer film functions as an A-plate, because the director of liquid crystal molecules is parallel to the glass substrate in the homogeneous orientation. On the other hand, orientation was determined to be homeotropic when transmitted light in the vertical direction was minimum, and transmitted light increased as a tilt angle was increased. The polymer film functions as a C-plate, because the director of liquid crystal molecules is perpendicular to the glass substrate in the homeotropic orientation.

(2) Measurement with a Polarimeter:

An Optipro polarimeter made by Shintech, Inc. was used. A polymer film was irradiated with light of wavelength at 550 nm. Retardation (Δn×d) was measured while the incident angle of light to the film surface was decreased from 90 degrees.

<Cationic Photopolymerization>

Heat of polymerization generated by cationic photopolymerization was measured using a PDC121 photochemical reaction calorimeter (Seiko Instruments Inc.). A sample on an aluminum pan was irradiated with ultraviolet light under a stream of dried air at 25° C.

Example 1

<Preparation of the Compound (1-1-20)>
First Step:

Sodium hydroxide (11.1 g) was added to a mixture of toluene (30 mL) and water (30 mL) under an atmosphere of nitrogen and the mixture was stirred at room temperature. Cyclohexenemethanol (6.2 g), 1,4-dibromobutane (18.0 g) and tetrabutylammoniumbromide (1.8 g) were added and the stirring was continued under reflux for another 3 hours. The organic phase was separated, washed sequentially with a saturated aqueous solution of sodium hydrogencarbonate and aqueous 10% solution of sodium chloride, and then dried over anhydrous magnesium sulfate. The solvent was distilled off and the residue was purified by means of column chromatography (silica gel, eluent: toluene), giving colorless oil [H1] (5.9 g).

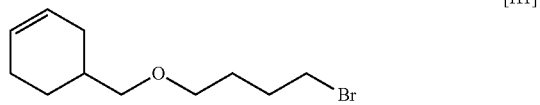

[H1]

NMR analysis data of the compound [H1] were as follows: $^1$H-NMR (CDCl$_3$; δ ppm): 5.67 (s, 2H), 3.47-3.42 (m, 4H), 3.33-3.25 (m, 2H), 2.15-2.02 (m, 3H), 2.00-1.68 (m, 7H) and 1.32-1.22 (m, 1H).

Second Step:

A mixture of the compound [H1] (5.9 g), 4-hydroxybenzoic acid methyl ester (4.0 g), potassium hydroxide (1.5 g) and DMF (60 mL) was heated at 80° C. for 6 hours under an atmosphere of nitrogen. Precipitates were removed by filtration under reduced pressure. Toluene (100 mL) and water (100 mL) was added to the filtrate, and an organic phase was separated. The organic phase was washed successively with a saturated aqueous solution of sodium hydrogencarbonate and water and the solvent was distilled off under reduced pressure. To the residue, methanol (20 mL), water (20 mL) and potassium hydroxide (1.5 g) was added and the mixture was stirred under reflux for 3 hours. The solvent was distilled off under reduced pressure and 3N-hydrochloric acid (100 mL) and toluene (100 mL) were added, and an organic phase was separated. The resultant organic phase was washed with water and the solvent was distilled off under reduced pressure. Recrystallization from ethanol gave colorless crystals of the compound [H2] (2.6 g).

[H2]

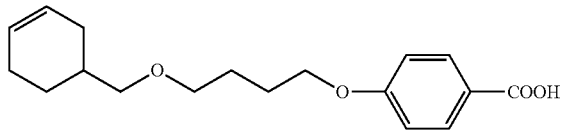

NMR analysis data of the compound [H2] were as follows: $^1$H-NMR (CDCl$_3$; δ ppm): 8.05 (d, 2H), 6.93 (d, 2H), 5.67 (s, 2H), 4.07 (t, 2H), 3.50 (t, 2H), 3.35-3.27 (m, 2H), 2.15-2.03 (m, 3H), 1.95-1.68 (m, 7H) and 1.33-1.23 (m, 1H).

Third Step:

DCC (1,3-dicyclohexylcarbodiimide) (1.9 g) was added to a cooled mixture of the compound [H2] (2.6 g), methylhydroquinone (0.5 g), DMAP (4-dimethylamonopyridine) (0.2 g) and dichloromethane (30 mL) under an atmosphere of nitrogen and the stiffing was continued at room temperature for another 16 hours. Precipitates were removed by filtration under reduced pressure and water was added to the filtrate, separating an organic phase. The organic phase was washed sequentially with 2N-hydrochloric acid and water, and then dried over anhydrous magnesium sulfate. The solvent was distilled off under reduced pressure and the residue was purified by column chromatography (silica gel, eluent: toluene/ethyl acetate=8/1 by volume), and then by recrystallization (toluene/methanol=1/10 by volume), giving colorless crystals of the compound [H3] (2.3 g).

[H3]

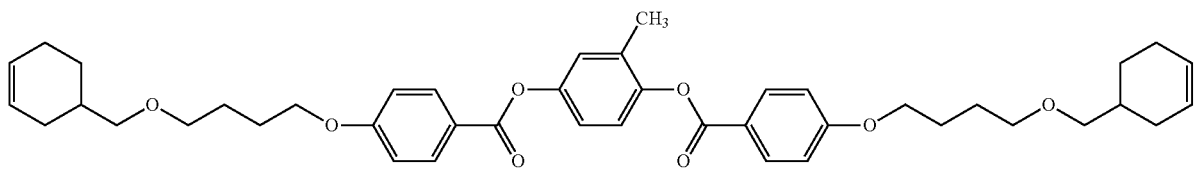

NMR analysis data and the phase transition temperature of the compound [H3] were as follows: C 72 N 98 I. $^1$H-NMR (CDCl$_3$; δ ppm): 8.16 (d, 2H), 8.14 (d, 2H), 7.17 (d, 1H), 7.13 (d, 1H), 7.10-7.06 (m, 1H), 6.99 (d, 2H), 6.97 (d, 2H), 5.68 (s, 2H), 4.12-4.07 (m, 4H), 3.51 (t, 4H), 3.36-3.29 (m, 4H), 2.25 (s, 3H), 2.15-2.02 (m, 6H), 1.96-1.70 (m, 16H) and 1.34-1.24 (m, 2H).

Final Step-Preparation of the Compound (1-1-20):

m-Chloroperbenzoic acid (1.9 g) was added to a cooled mixture of the compound [H3] (2.3 g) and dichloromethane (25 mL) under an atmosphere of nitrogen and the stirring was continued at room temperature for another 16 hours. Precipitates were removed by filtration under reduced pressure and the filtrate was washed sequentially with an aqueous 10% solution of sodium hydrogen sulfite, an aqueous 3% solution of sodium hydroxide and water, and dried over anhydrous magnesium sulfate. The solvent was distilled off under reduced pressure and the residue was purified by column chromatography (silica gel, eluent: toluene/ethyl acetate=4/1 by volume), and then by recrystallization (toluene/methanol=1/10 by volume), giving colorless crystals of the compound (1-1-20) (0.9 g).

(1-1-20)

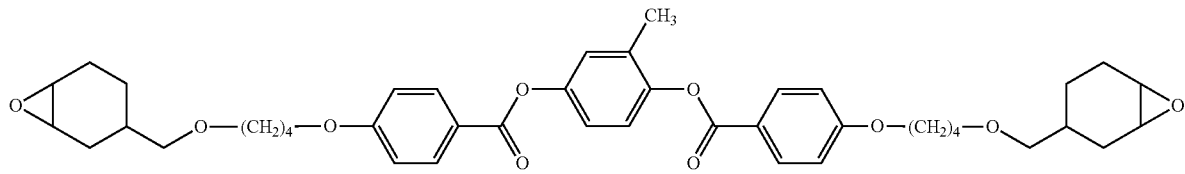

NMR analysis data and the phase transition temperature of the compound (1-1-20) were as follows: C 62 N 85 I.
¹H-NMR (CDCl₃; δ ppm): 8.18 (d, 2H), 8.14 (d, 2H), 7.18 (d, 1H), 7.13 (d, 1H), 7.10-7.06 (m, 1H), 6.99 (d, 2H), 6.97 (d, 2H), 3.47 (t, 4H), 3.28-3.13 (m, 8H), 2.25 (s, 3H), 2.20-1.97 (m, 4H), 1.94-1.70 (m, 10H), 1.62-1.40 (m, 10H), 1.20-1.10 (m, 1H) and 1.06-0.96 (m, 1H).

Example 2

<Preparation of the Compound (1-3-21)>
First Step:

p-Toluenesulfonyl chloride (37.4 g) was added to a mixture of cyclohexenemethanol (20.0 g), pyridine (20 mL) and toluene (60 mL) at room temperature and the stirring was continued at room temperature for another 16 hours. Precipitates were removed by filtration under reduced pressure and water (40 mL) was added to the filtrate, and the mixture was heated with stirring at 40° C. for 3 hours. The organic phase was separated and washed sequentially with 1N-hydrochloric acid, a saturated aqueous solution of sodium hydrogencarbonate and water, and then dried over anhydrous magnesium sulfate. The solvent was distilled off, giving a colorless oil of the compound [H4] (45.2 g).

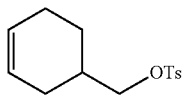

[H4]

Second Step:

A mixture of the compound [H4] (30.0 g), 4-hydroxybenzoic acid methyl ester (18.9 g), potassium hydroxide (7.0 g) and methanol (300 mL) was heated under reflux with stirring for 20 hours under an atmosphere of nitrogen. Precipitated salts were removed by filtration under reduced pressure and the solvent was distilled off from the filtrate under reduced pressure. Toluene (100 mL) and water (100 mL) were added to the residue and an organic phase was separated. The organic phase was washed sequentially with a saturated aqueous solution of sodium hydrogencarbonate and water, and the solvent was distilled off under reduced pressure. Then, methanol (60 mL), water (60 mL) and potassium hydroxide (7.6 g) were added to the residue and the mixture was heated under reflux with stirring for 3 hours. The solvent was distilled off under reduced pressure and the residue was poured into 3N-hydrochloric acid (300 mL). The compound [H5] precipitated was filtered under reduced pressure and purified by recrystallization from ethanol, giving colorless crystals of the compound [H5] (18.5 g).

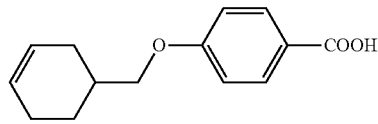

[H5]

NMR analysis data of the compound [H5] were as follows:
¹H-NMR (CDCl₃; δ ppm): 8.06 (d, 2H), 6.94 (d, 2H), 5.70 (s, 2H), 3.92 (d, 2H), 2.24-2.08 (m, 4H), 1.97-1.84 (m, 2H) and 1.59-1.50 (m, 1H).

Third Step:

Thionyl chloride (245.6 g) was added to a cooled mixture of allyl alcohol (100.0 g) and THF (248.3 g) under an atmosphere of nitrogen and the mixture was heated with stirring at 60° C. for 4 hours. The solvent was distilled off under reduced pressure, giving colorless oil. Then, hydroquinone (10.0 g), potassium hydroxide (5.1 g), potassium iodide (1.0 g) and Solmix (100 mL) were added to the oil and the mixture was heated under reflux for 8 hours. The solvent was distilled off under reduced pressure and toluene (200 mL) and 10%-hydrochloric acid (200 mL) were added to the residue and an organic phase was separated. The organic phase was washed sequentially with a saturated aqueous solution of sodium hydrogencarbonate and water, and the solvent was distilled off under reduced pressure. The residue was purified by column chromatography (silica gel; eluent: toluene/ethyl acetate=4/1 by volume), giving colorless oil of the compound [H6] (5.1 g).

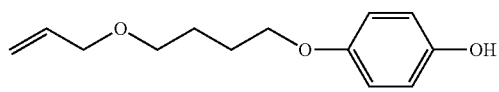

[H6]

NMR analysis data of the compound [H6] were as follows:
¹H-NMR (CDCl₃; δ ppm): 6.73 (s, 4H), 5.97-5.87 (m, 1H), 5.27 (d, 1H), 5.18 (d, 1H), 4.00 (d, 2H), 3.89 (t, 2H) and 1.88-1.72 (m, 4H).

Fourth Step:

DCC (4.7 g) was added to a cooled mixture of the compound [H5] (5.0 g), the compound [H6] (4.8 g), DMAP (0.5 g) and dichloromethane (50 mL) under an atmosphere of nitrogen, and the stirring was continued at room temperature for another 16 hours. Precipitates were removed by filtration under reduced pressure and water was added to the filtrate, separating an organic phase. The organic phase was washed sequentially with 2N-hydrochloric acid and water, and dried over anhydrous magnesium sulfate. The solvent was distilled off under reduced pressure and the residue was purified by column chromatography (silica gel; eluent: toluene/ethyl acetate=8/1 by volume), and then by recrystallization (toluene/methanol=1/10 by volume), giving colorless crystals of the compound [H7] (6.0 g).

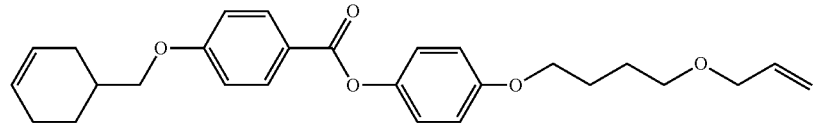

[H7]

NMR analysis data of the compound [H7] were as follows: $^1$H-NMR (CDCl$_3$; δ ppm): 8.13 (d, 2H), 7.10 (d, 2H), 6.97 (d, 2H), 6.92 (d, 2H), 5.97-5.87 (m, 1H), 5.72 (s, 2H), 5.29 (d, 1H), 5.19 (d, 1H), 4.02-3.97 (m, 4H), 3.93 (d, 2H), 2.30-2.10 (m, 5H), 1.98-1.84 (m, 5H), 1.82-1.74 (m, 2H) and 1.50-1.40 (m, 1H).

Final Step-Preparation of the compound (1-3-21):

m-Chloroperbenzoic acid (8.0 g) was added to a cooled mixture of the compound [H7] (6.0 g) and dichloromethane (60 mL) under an atmosphere of nitrogen and the stirring was continued at room temperature for another 16 hours. Precipitates were removed by filtration under reduced pressure and the filtrate was washed sequentially with an aqueous 10% solution of sodium hydrogen sulfite, aqueous 3% sodium hydroxide solution and water, and dried over anhydrous magnesium sulfate. The solvent was distilled off under reduced pressure and the residue was purified by column chromatography (silica gel, eluent: toluene/ethyl acetate=4/1 by volume), and then by recrystallization (toluene/methanol=1/10 by volume), giving colorless crystals of the compound (1-3-21) (3.1 g).

NMR analysis data of the compound [H8] were as follows: $^1$H-NMR (CDCl$_3$; δ ppm): 6.97 (d, 2H), 6.87 (d, 2H), 5.93-5.87 (m, 1H), 5.73 (s, 2H), 5.28 (d, 1H), 5.18 (d, 1H), 4.01-3.94 (m, 4H), 3.50 (t, 2H), 2.84-2.76 (m, 1H), 2.39 (d, 2H), 2.23-2.11 (m, 3H) and 1.91-1.74 (m, 5H).

Final Step-Preparation of the Compound (1-3-7):

m-Chloroperbenzoic acid (19.4 g) was added to a cooled mixture of the compound [H8] (11.0 g) and dichloromethane (110 mL) under an atmosphere of nitrogen and the stirring was continued at room temperature for another 16 hours. Precipitates were removed by filtration under reduced pressure. The filtrate was washed sequentially with an aqueous 10% solution of sodium hydrogen sulfite, an aqueous 3% solution of sodium hydroxide and water, and dried over anhydrous magnesium sulfate. The solvent was distilled off under reduced pressure and the residue was purified by column chromatography (silica gel; eluent: toluene/ethyl acetate=4/1 by volume), giving colorless oil of the compound (1-3-7) (3.5 g).

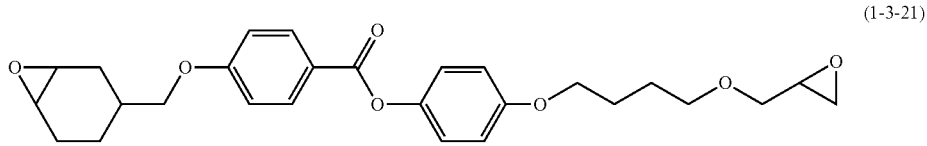 [SMILES: O=C(Oc1ccc(OCCCCOCC2CO2)cc1)c1ccc(OCC2CCC3OC3C2)cc1]

(1-3-21)

NMR analysis data and the phase transition temperature of the compound (1-3-21) were as follows: C 86 (SmA 22 N 70) I. $^1$H-NMR (CDCl$_3$; δ ppm): 8.12 (d, 2H), 7.09 (d, 2H), 6.94 (d, 2H), 6.92 (d, 2H), 3.99 (t, 2H), 3.90-3.79 (m, 2H), 3.77-3.73 (m, 1H), 3.63-3.52 (m, 2H), 3.43-3.37 (m, 1H), 3.28-3.24 (m, 1H), 3.23-3.14 (m, 3H), 2.81 (t, 1H), 2.64-2.61 (m, 1H), 2.33-2.18 (m, 2H), 2.12-2.03 (m, 1H), 1.98-1.75 (m, 6H), 1.72-1.52 (m, 3H), 1.37-1.27 (m, 1H) and 1.22-1.13 (m, 1H).

Example 3

<Preparation of the Compound (1-3-7)>

First Step:

DCC (8.9 g) was added to a cooled mixture of 3-cyclohexene-1-carboxylic acid (5.0 g), the compound [H6] (8.8 g), DMAP (1.0 g) and dichloromethane (50 mL) under an atmosphere of nitrogen, and the stirring was continued at room temperature for another 16 hours. Precipitates were removed by filtration under reduced pressure and water was added to the filtrate, separating an organic phase. The organic phase was washed sequentially with 2N-hydrochloric acid and water, and then dried over anhydrous magnesium sulfate. The solvent was distilled off under reduced pressure and the residue was purified by column chromatography (silica gel; eluent: toluene/ethyl acetate=8/1 by volume), giving colorless oil of the compound [H8] (11.5 g).

[H8]

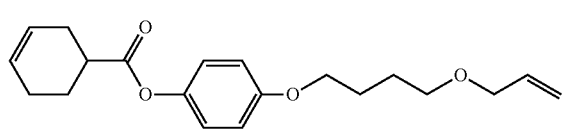

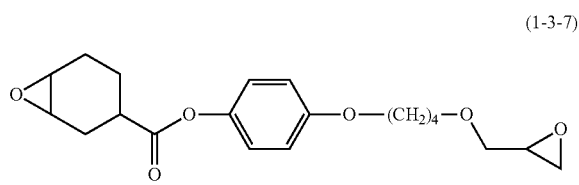

(1-3-7)

NMR analysis data of the compound (1-3-7) were as follows: $^1$H-NMR (CDCl$_3$; δ ppm): 6.95 (d, 2H), 6.87 (d, 2H), 3.96 (t, 2H), 3.74 (d, 2H), 3.62-3.50 (m, 2H), 3.41-3.36 (m, 1H), 3.32-3.13 (m, 3H), 2.83-2.72 (m, 2H), 2.63-2.60 (m, 1H), 2.54-2.24 (m, 2H) and 2.15-1.53 (m, 8H).

Example 4

<Preparation of the Compound (1-4-24)>

First Step:

DCC (17.2 g) was added to a cooled mixture of 3-cyclohexene-1-carboxylic acid (10.0 g), 1-hydroxy-4-propylcyclohexane (12.6 g), DMAP (1.9 g) and dichloromethane (100 mL) under an atmosphere of nitrogen and the stirring was continued at room temperature for another 16 hours. Precipitates were removed by filtration under reduced pressure and water was added to the filtrate, separating an organic phase. The organic phase was washed sequentially with 2N-hydrochloric acid and water, and then dried over anhydrous magnesium sulfate. The solvent was distilled off under reduced pressure and the residue was purified by column chromatography (silica gel, eluent: toluene), and then by recrystallization (toluene/methanol=1/5 by volume), giving colorless crystals of the compound [H9] (14.3 g).

[H9]

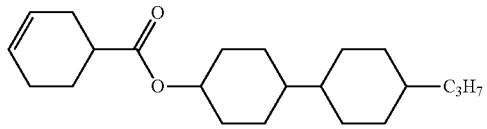

NMR analysis data of the compound [H9] were as follows: $^1$H-NMR (CDCl$_3$; δ ppm): 5.67 (s, 2H), 4.69-4.61 (m, 1H), 2.55-2.47 (m, 1H), 2.23 (d, 2H), 2.12-2.06 (m, 2H), 2.02-1.94 (m, 3H), 1.80-1.63 (m, 7H), 1.35-1.25 (m, 4H) and 1.17-0.79 (m, 14H).

Final Step-Preparation of the Compound (1-4-24):

m-Chloroperbenzoic acid (12.3 g) was added to a cooled mixture of the compound [H9] (14.0 g) and dichloromethane (140 mL) under an atmosphere of nitrogen and stirring was continued at room temperature for another 16 hours. Precipitates were removed by filtration under reduced pressure and the filtrate was washed sequentially with an aqueous 10% solution of sodium hydrogen sulfite, an aqueous 3% solution of sodium hydroxide and water, and dried over anhydrous magnesium sulfate. The solvent was distilled off under reduced pressure and the residue was purified by column chromatography (silica gel, eluent: toluene/ethyl acetate=8/1 by volume), and then by recrystallization (toluene/methanol=1/5 by volume), giving colorless crystals of the compound (1-4-24) (11.0 g).

(1-4-24)

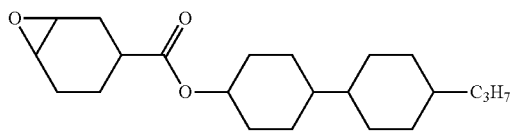

NMR analysis data and the phase transition temperature of the compound (1-4-24) were as follows: C 127 I. $^1$H-NMR (CDCl$_3$; δ ppm): 4.67-4.58 (m, 1H), 3.25-3.22 (m, 1H), 3.18-3.13 (m, 1H), 2.50-2.43 (m, 1H), 2.27-2.10 (m, 2H), 2.02-1.88 (m, 3H), 1.81-1.52 (m, 8H), 1.48-1.38 (m, 1H), 1.34-1.23 (m, 4H) and 1.19-0.79 (m, 14H).

Example 5

<Preparation of the Compound (1-2-7)>
First Step:

DCC (3.6 g) was added to a cooled mixture of the compound [H2] (5.0 g), 4-cyanophenol (2.0 g), DMAP (0.4 g) and dichloromethane (100 mL) under an atmosphere of nitrogen and the stirring was continued at room temperature for another 16 hours. Precipitates were removed by filtration under reduced pressure and water was added to the filtrate, separating an organic phase. The organic phase was washed sequentially with 2N-hydrochloric acid and water, and then dried over anhydrous magnesium sulfate. The solvent was distilled off under reduced pressure and the residue was purified by column chromatography (silica gel, eluent: toluene/ethyl acetate=8/1 by volume), and then by recrystallization (toluene/methanol=1/10 by volume), giving colorless crystals of the compound [H10] (5.2 g).

[H10]

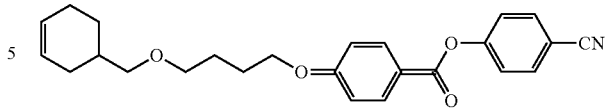

NMR analysis data of the compound [H10] were as follows: $^1$H-NMR (CDCl$_3$; δ ppm): 8.12 (d, 2H), 7.74 (d, 2H), 7.35 (d, 2H), 6.98 (d, 2H), 5.67 (s, 2H), 4.09 (t, 2H), 3.50 (t, 2H), 3.36-3.29 (m, 2H), 2.15-2.03 (m, 3H), 1.97-1.70 (m, 7H) and 1.33-1.24 (m, 1H).

Final Step-Preparation of the Compound (1-2-7):

m-Chloroperbenzoic acid (3.6 g) was added to a cooled mixture of the compound [H10] (5.0 g) and dichloromethane (50 mL) under an atmosphere of nitrogen and the stirring was continued at room temperature for another 16 hours. Precipitates were removed by filtration under reduced pressure and the filtrate was washed sequentially with an aqueous 10% solution of sodium hydrogen sulfite, an aqueous 3% solution of sodium hydroxide and water, and dried over anhydrous magnesium sulfate. The solvent was distilled off under reduced pressure and the residue was purified by column chromatography (silica gel, eluent: toluene/ethyl acetate=8/1 by volume), and then by recrystallization (toluene/methanol=1/5 by volume), giving colorless crystals of the compound (1-2-7) (3.7 g).

(1-2-7)

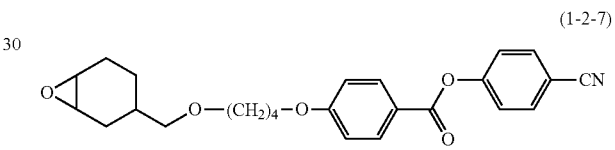

NMR analysis data and the phase transition temperature of the compound (1-2-7) were as follows: C 61 I. $^1$H-NMR (CDCl$_3$; δ ppm): 8.13 (d, 2H), 7.73 (d, 2H), 7.35 (d, 2H), 6.98 (d, 2H), 4.08 (t, 2H), 3.46 (t, 2H), 3.29-3.14 (m, 4H), 2.19-2.12 (m, 1H), 2.10-1.97 (m, 1H), 1.95-1.70 (m, 6H), 1.60-1.4 (m, 2H) and 1.20-0.95 (m, 1H).

Example 6

<Preparation of the Compound (1-1-3)>
First Step:

A mixture of hydroquinone (52.9 g), the compound [H1] (59.3 g), sodium hydroxide (19.2 g) and DMF (300 mL) was heated at 80° C. for 6 hours under an atmosphere of nitrogen. Precipitated salts were removed by filtration under reduced pressure. Toluene (500 mL) and water (500 mL) were added to the filtrate and an organic phase was separated. The organic phase was washed sequentially with a saturated aqueous solution of sodium hydrogencarbonate and water and dried over anhydrous magnesium sulfate. The solvent was distilled off under reduced pressure and the residue was purified by column chromatography (silica gel, eluent: toluene/ethyl acetate=4/1 by volume), giving colorless oil of the compound [H11] (39.9 g).

[H11]

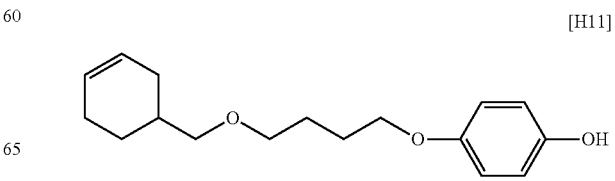

NMR analysis data of the compound [H11] were as follows: $^1$H-NMR (CDCl$_3$; δ ppm): 6.80-6.72 (m, 4H), 5.66 (s, 2H), 5.27 (s, 1H), 3.91 (t, 2H), 3.50 (t, 2H), 3.38-3.29 (m, 2H), 2.16-2.02 (m, 3H), 1.97-1.68 (m, 7H) and 1.32-1.21 (m, 1H).
Second Step:

DCC (17.8 g) was added to a cooled mixture of the compound [H2] (25.0 g) the compound [H11] (20.2 g), DMAP (2.0 g) and dichloromethane (250 mL) and the stirring was continued at room temperature for another 16 hours. Precipitates were removed by filtration under reduced pressure and water was added to the filtrate, separating an organic phase. The organic phase was washed sequentially with 2N-hydrochloric acid and water, and then dried over anhydrous magnesium sulfate. The solvent was distilled off under reduced pressure and the residue was purified by column chromatography (silica gel, eluent: toluene/ethyl acetate=8/1 by volume), and then by recrystallization (toluene/methanol=1/10 by volume), giving colorless crystals of the compound [H12] (35.4 g).

Example 7

<Preparation of the Compound (1-2-6)>
First Step:

DCC (14.2 g) was added to a mixture of the compound [H2] (20.0 g), 4-methoxyphenol (8.2 g), DMAP (1.6 g) and dichloromethane (200 mL) under an atmosphere of nitrogen and the stirring was continued at room temperature for another 16 hours. Precipitates were removed by filtration under reduced pressure and water was added to the filtrate, separating an organic phase. The organic phase was washed sequentially with 2N-hydrochloric acid and water, and then dried over anhydrous magnesium sulfate. The solvent was distilled off under reduced pressure and the residue was purified by column chromatography (silica gel, eluent: toluene/ethyl acetate=8/1 by volume), and then by recrystallization (toluene/methanol=1/10 by volume), giving colorless crystals of the compound [H13] (23.1 g).

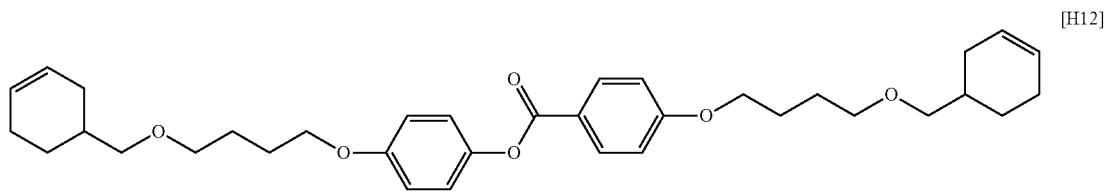 [SMILES: O=C(Oc1ccc(OCCCCOCC2CC=CCC2)cc1)c1ccc(OCCCCOCC2CC=CCC2)cc1]

[H12]

NMR analysis data of the compound [H12] were as follows: $^1$H-NMR (CDCl$_3$; δ ppm): 8.12 (d, 2H), 7.09 (d, 2H), 6.96 (d, 2H), 6.91 (d, 2H), 5.67 (s, 2H), 4.08 (t, 2H), 3.99 (t, 2H), 3.53-3.47 (m, 4H), 3.36-3.27 (m, 4H), 2.17-2.02 (m, 6H), 1.97-1.70 (m, 14H) and 1.34-1.23 (m, 2H).
Final Step-Preparation of the Compound (1-1-3):

m-Chloroperbenzoic acid (31.1 g) was added to a cooled mixture of the compound [H12] (30.0 g) and dichloromethane (300 mL) under an atmosphere of nitrogen and the stirring was continued at room temperature for another 16 hours. Precipitates were removed by filtration under reduced pressure and the filtrate was washed sequentially with an aqueous 10% solution of sodium hydrogen sulfite, an aqueous 3% solution of sodium hydroxide and water, and dried over anhydrous magnesium sulfate. The solvent was distilled off under reduced pressure and the residue was purified by column chromatography (silica gel, eluent: toluene/ethyl acetate=4/1 by volume), and then by recrystallization (toluene/methanol=1/10 by volume), giving colorless crystals of the compound (1-1-3) (18.7 g).

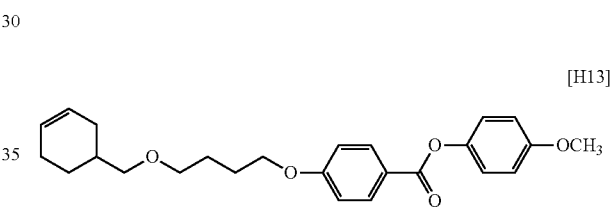

[H13]

NMR analysis data of the compound [H13] were as follows: $^1$H-NMR (CDCl$_3$; δ ppm): 8.13 (d, 2H), 7.11 (d, 2H), 6.97 (d, 2H), 6.94 (d, 2H), 5.67 (s, 2H), 4.08 (t, 2H), 3.82 (s, 3H), 3.50 (t, 2H), 3.36-3.29 (m, 2H), 2.18-2.07 (m, 3H), 1.96-1.71 (m, 7H) and 1.34-1.25 (m, 1H).
Final Step-Preparation of the Compound (1-2-6):

m-Chloroperbenzoic acid (16.2 g) was added to a cooled mixture of the compound [H13] (22.7 g) and dichloromethane (230 mL) under an atmosphere of nitrogen and the stirring was continued at room temperature for another 16 hours. Precipitates were removed by filtration under reduced pressure and the filtrate was washed sequentially with an

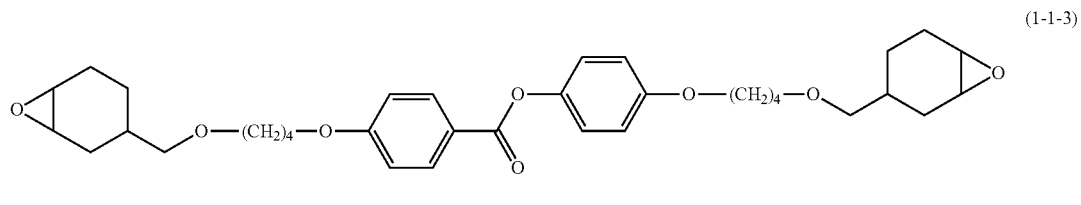

(1-1-3)

NMR analysis data and the phase transition temperature of the compound (1-1-3) were as follows: C 46 (N-6) I. $^1$H-NMR (CDCl$_3$; δ ppm): 8.13 (d, 2H), 7.89 (d, 2H), 6.96 (d, 2H), 6.91 (d, 2H), 4.07 (t, 2H), 3.98 (t, 2H), 3.49-3.43 (m, 4H), 3.28-3.13 (m, 8H), 2.20-1.70 (m, 15H), 1.62-1.40 (m, 5H) and 1.20-0.97 (m, 2H).

aqueous 10% solution of sodium hydrogen sulfite, an aqueous 3% solution of sodium hydroxide and water, and dried over anhydrous magnesium sulfate. The solvent was distilled off under reduced pressure and the residue was purified by column chromatography (silica gel, eluent: toluene/ethyl acetate=8/1 by volume), and then by recrystallization (toluene/methanol=1/5 by volume), giving colorless crystals of the compound (1-2-6) (17.9 g).

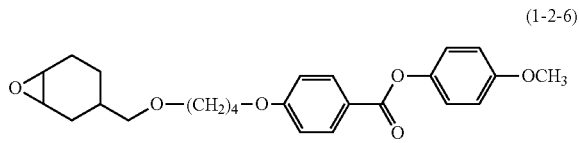
(1-2-6)

NMR analysis data and the phase transition temperature of the compound (1-2-6) were as follows: C 61 I. $^1$H-NMR (CDCl$_3$; δ ppm): 8.13 (d, 2H), 7.11 (d, 2H), 6.96 (d, 2H), 6.93 (d, 2H), 4.07 (t, 2H), 3.82 (s, 2H), 3.45 (t, 2H), 3.28-3.14 (m, 4H), 2.18-1.97 (m, 2H), 1.92-1.72 (m, 6H), 1.58-1.42 (m, 3H) and 1.22-0.94 (m, 1H).

Example 8

<Preparation of the Compound (1-1-45)>
First Step:

DCC (7.1 g) was added to a cooled mixture of the compound [H2] (10.0 g), methoxyhydriqunone (2.3 g), DMAP (0.8 g), dichloromethane (100 mL) under an atmosphere of nitrogen and the stirring was continued at room temperature for another 16 hours. Precipitates were removed by filtration under reduced pressure and water was added to the filtrate, separating an organic phase. The organic phase was washed sequentially with 2N-hydrochloric acid and water, and then dried over anhydrous magnesium sulfate. The solvent was distilled off under reduced pressure and the residue was purified by column chromatography (silica gel, eluent: toluene/ethyl acetate=8/1 by volume), and then by recrystallization (toluene/methanol=1/10 by volume), giving colorless crystals of the compound [H14] (7.8 g).

Final Step-Preparation of the Compound (1-1-45):

m-Chloroperbenzoic acid (6.4 g) was added to a cooled mixture of the compound [H14] (7.8 g) and dichloromethane (80 mL) under an atmosphere of nitrogen and the stirring was continued at room temperature for another 16 hours. Precipitates were removed by filtration under reduced pressure and the filtrate was washed sequentially with an aqueous 10% solution of sodium hydrogen sulfite, an aqueous 3% solution of sodium hydroxide and water, and dried over anhydrous magnesium sulfate. The solvent was distilled off under reduced pressure and the residue was purified by column chromatography (silica gel, eluent: toluene/ethyl acetate=4/1 by volume), and then dried under reduced pressure, giving colorless oil of the compound (1-1-45) (5.2 g). The compound was liquid crystal at room temperature.

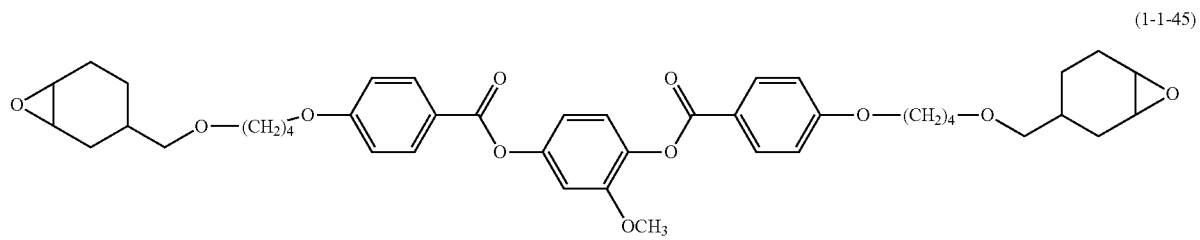
(1-1-45)

NMR analysis data and the phase transition temperature of the compound (1-1-45) were as follows: N 55 I. $^1$ H-NMR (CDCl$_3$ ; δppm): 8.15(t, 4H), 7.17(d, 1H), 7.00-6.95(m, 4H), 6.89(d, 1H), 6.86-6.82(m, 1H), 4.11-4.05(m, 4H), 3.80(s, 3H), 3.46(t, 4H), 3.29-3.12(m, 8H), 2.19-2.12(m, 2H), 2.11-1.96(m, 2H), 1.94-1.70(m, 12H), 1.61-1.40(m, 4H), 1.24-1.10(m, 1H) 1.06-0.95(m, 1H).

Example 9

<Preparation of the Compound (1-1-46)>
First Step:

DCC (7.1 g) was added to a cooled mixture of the compound [H2] (10.0 g), 4,4'-dihydroxybiphenyl (3.1 g), DMAP (0.8 g) and dichloromethane (100 mL) under an atmosphere of nitrogen and the stirring was continued at room temperature for another 16 hours. Precipitates were removed by filtration under reduced pressure and water was added to the filtrate, separating an organic phase. The organic phase was washed sequentially with 2N-hydrochloric acid and water,

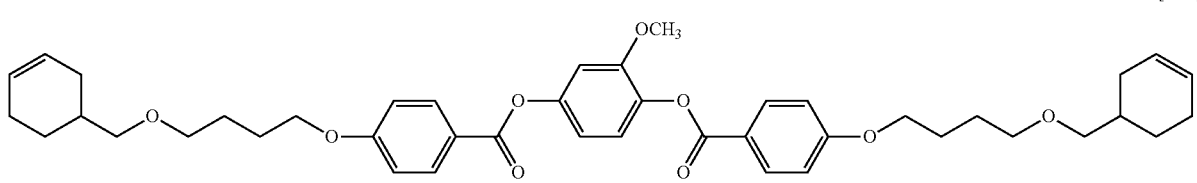
[H14]

NMR analysis data of the compound [H14] were as follows: $^1$H-NMR (CDCl$_3$; δ ppm): 8.15 (t, 4H), 7.17 (d, 1H), 7.01-6.96 (m, 4H), 6.88 (d, 1H), 6.86-6.82 (m, 1H), 5.68 (s, 4H), 4.12-4.07 (m, 4H), 3.81 (s, 3H), 3.51 (t, 4H), 3.37-3.29 (m, 4H), 2.16-2.03 (m, 6H), 1.96-1.86 (m, 6H), 1.86-1.70 (m, 8H) and 1.34-1.24 (m, 2H).

and then dried over anhydrous magnesium sulfate. The solvent was distilled off under reduced pressure and the residue was purified by column chromatography (silica gel, eluent: toluene/ethyl acetate=8/1 by volume), and then by recrystallization from ethyl acetate, giving colorless crystals of the compound [H15] (8.1 g).

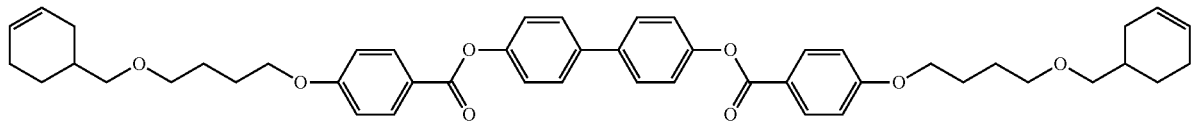
[H15]

NMR analysis data of the compound [H15] were as follows: ¹H-NMR (CDCl₃; δ ppm): 8.17 (d, 4H), 7.63 (d, 4H), 7.29 (d, 4H), 6.99 (d, 4H), 5.68 (s, 4H), 4.09 (t, 4H), 3.51 (t, 4H), 3.37-3.29 (m, 4H), 2.16-2.03 (m, 6H), 1.97-1.86 (m, 6H), 1.86-1.70 (m, 8H), and 1.34-1.24 (m, 2H).

Final Step-Preparation of the Compound (1-1-46):

m-Chloroperbenzoic acid (6.1 g) was added to a cooled mixture of the compound [H15] (7.9 g) and dichloromethane (80 mL) under an atmosphere of nitrogen and the stirring was continued at room temperature for another 16 hours. Precipitates were removed by filtration under reduced pressure and the filtrate was washed sequentially with an aqueous 10% solution of sodium hydrogen sulfite, an aqueous 3% solution of sodium hydroxide and water, and dried over anhydrous magnesium sulfate. The solvent was distilled off under reduced pressure and the residue was purified by column chromatography (silica gel, eluent: toluene/ethyl acetate=2/1 by volume), and then dried under reduced pressure, giving colorless oil of the compound (1-1-45) (4.6 g).

¹H-NMR (CDCl₃; δ ppm): 8.17 (d, 4H), 7.63 (d, 4H), 7.28 (d, 4H), 6.99 (d, 4H), 4.08 (t, 4H), 3.29-3.13 (m, 8H), 2.20-2.13 (m, 2H), 2.11-1.97 (m, 2H), 1.95-1.64 (m, 12H), 1.62-1.40 (m, 4H), 1.21-1.10 (m, 1H) and 1.06-0.96 (m, 1H).

Component compounds excluding the compound (1) used in Examples of the following polymerizable liquid crystal compositions are shown below. These compounds can be synthesized by means of a combination of techniques in synthetic organic chemistry. Methods for an introduction of objective terminal groups, rings and bonding groups to starting materials are described in books such as Houben-Weyl, Methods of Organic Chemistry, Georg Thieme Verlag, Stuttgart; Organic syntheses, John Wily & Sons, Inc.; Organic Reactions, John Wily & Sons Inc.; Comprehensive Organic Synthesis, Pergamon Press; and New Experimental Chemistry Course (Shin Jikken Kagaku Kouza, in Japanese title), Maruzen Co., LTD.

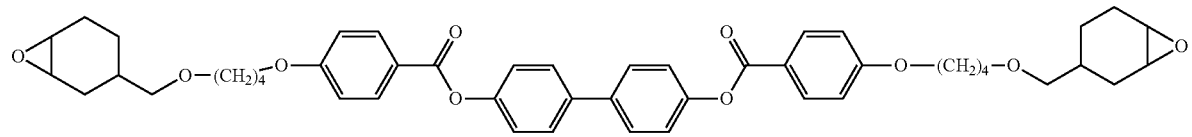
(1-1-46)

NMR analysis data and the phase transition temperature of the compound (1-1-46) were as follows: C 117 N 250<I.

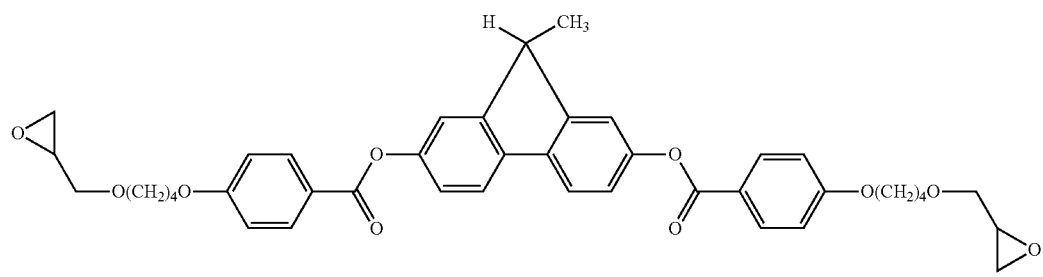
(M1-1-1)

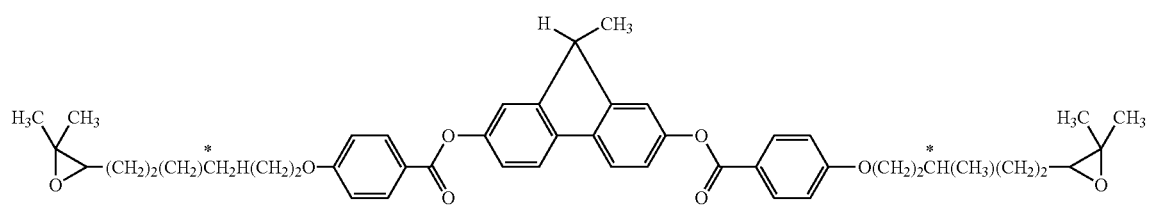
(M1-1-2)

-continued

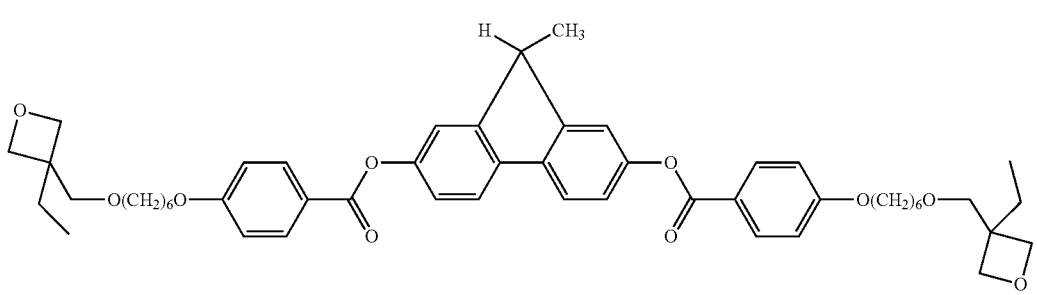

(M1-1-3)

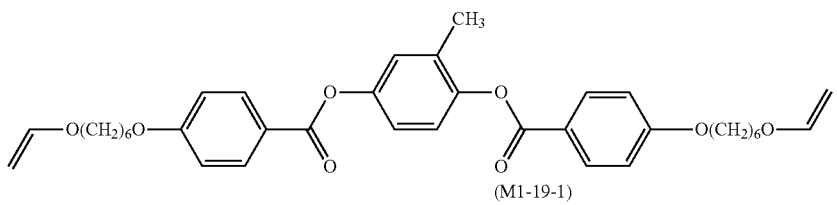

(M1-7-1)

(M1-19-1)

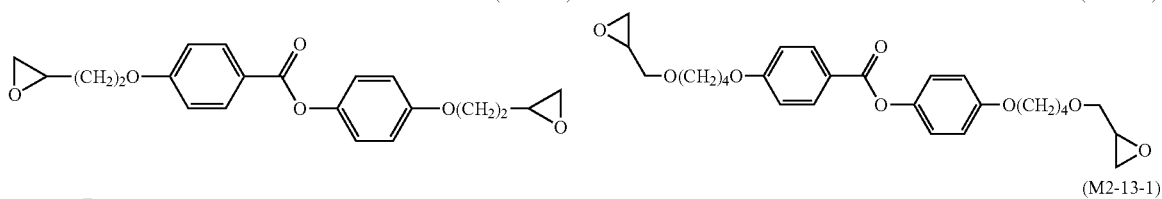

(M1-19-2)

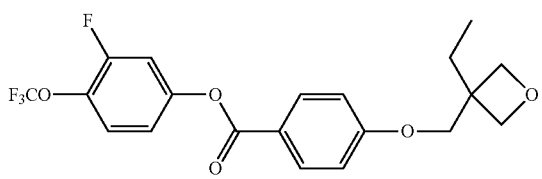

(M2-13-1)

(6-8-1)

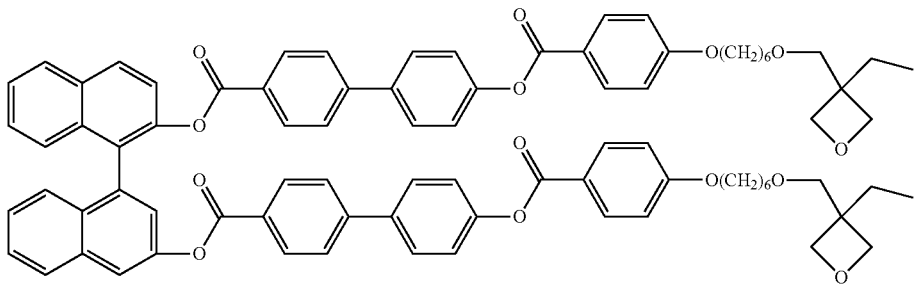

(M1-7-2)

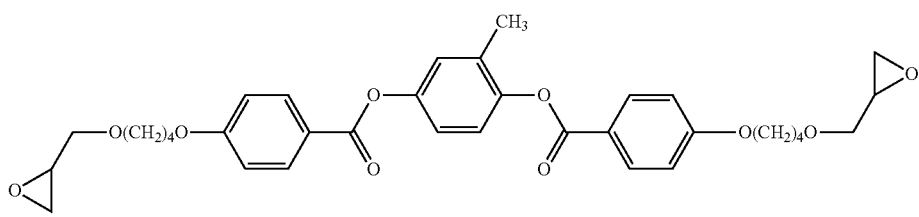

Concrete methods for synthesizing the compounds described above are explained. The compound (M1-1-1) and the compound (M1-1-3) are prepared by the method described in JP 2005-60373 A. The compound (M1-1-2) is prepared by the method described in JP 2005-097281 A. The compound (M1-7-1) is prepared by the method described in Polymer, 34 (8), 1736-1740 (1993). The compound (M1-19-1) and the compound (M1-19-2) are prepared by the method described in Macromolecules, 26, 1244-1247 (1993). The compound (M2-13-1) is prepared by the method described in JP 2005-320317 A. The compound (6-8-1) is prepared by the method described in JP 2005-263778 A. The compound (M1-7-2) can be prepared in a manner similar to that for the compound (M1-1-1) using methylhydroquinone instead of 9-methyl-2,7-dihydroxyfluorene. The compound (M1-7-3) is described in Makromol. Chem., 190, 2255-2268 (1989).

Example 10

A mixture of the compound (1-1-20)/a polymerization initiator CPI-110P (San-Apro Ltd.) in a weight ratio of 100/0.02 was dissolved in cyclopentanone, and a solution in which the concentration of the compounds was 20% by weight was prepared. The solution was spread on an aluminum pan, which was placed on a hot plate heated at 80° C. for 30 minutes and the solvent was evaporated. A large exothermic peak and a quick arrival to the top of the peak was observed when the sample on the aluminum pan was irradiated with ultraviolet light (365 nm, 15 mW/cm$^2$) under a flow of dried air by use of a PDC121 photochemical reaction calorimeter (Seiko Instruments Inc.).

Comparative Example 1

A sample was prepared in the same way as described in Example 10 except for replacement of the compound (1-1-20) with the compound (M1-7-2). A slow arrival to the top of the peak was observed when heat of reaction was measured by the method described in Example 10.

Example 11

A mixture of the compound (1-2-14) and the compound (M1-19-1) in a weight ratio of 70/30 was dissolved in a mixed solvent of PGMEA/MMP=9/1 by volume, and a composition in which the concentration of the compounds was 30% by weight was prepared. Deposition of crystals and so forth were not observed when the composition was allowed to stand for more than 3 days at room temperature. PGMEA and MMP stand for propylene glycol monoethyl ether acetate and methyl 3-methoxypropionate, respectively.

Comparative Example 2

A composition was prepared by the method described in Example 11 except for replacement of the compound (1-2-14) with the compound (M1-7-2). Crystals were deposited for 1 hour when the composition was allowed to stand at room temperature.

Example 12

A mixture of the compound (1-1-20)/the compound (1-2-7) in a weight ratio of 80/20 was dissolved in n-butyl acetate, and a composition in which the concentration of the compounds was 20% by weight was prepared. A silicone-based nonionic surfactant BYK-333 (BYK Additives & Instruments) in a weight ratio of 0.001 and a polymerization initiator CPI-110P in a weight ratio of 0.02 were added to the composition. The resultant solution was applied with a spin-coater to a glass substrate having a rubbed polyimide alignment film. The glass substrate was placed on a hot plate at 70° C. for 120 seconds, evaporating the solvent and forming a paint film. Then, the paint film was photopolymerized in air at room temperature for 30 seconds, with irradiance of 30 mW/cm$^2$ (a central wavelength at 365 nm) using a 250 W-ultra high-pressure mercury lamp. The formed thin film was fixed in a homogeneous orientation and exhibited optical properties of an A-plate.

Example 13

A mixture of the compound (1-1-20)/the compound (M1-19-1)/the compound (M1-1-3) in a weight ratio of 60/30/10 was dissolved in a mixed solvent of PGMEA/cyclopentanone=1/1 by volume, and a composition in which the concentration of the compounds was 20% by weight was prepared. A fluorine-based nonionic surfactant FTX-218 (Neos Company Limited) in a weight ratio of 0.002 and a polymerization initiator CPI-110P in a weight ratio of 0.02 were added to the composition. The thin film formed from the resultant solution according to the method described in Example 12 exhibited optical properties of an A-plate.

Example 14

A mixture of the compound (1-3-21)/the compound (M1-19-2) in a weight ratio of 70/30 was dissolved in PGMEA/MMP=1/1 by volume, and a composition in which the concentration of the compounds was 20% by weight was prepared. A hydrocarbon-based nonionic surfactant Polyflow No. 75 (Kyoeisha Chemical Co., Ltd.) in a weight ratio of 0.002 and a polymerization initiator CPI-110P in a weight ratio of 0.02 were added. The thin film formed from the resultant solution according to the method described in Example 12 exhibited optical properties of an A-plate.

Example 15

A mixture of the compound (1-1-20)/the compound (M1-7-1)/the compound (M1-1-3) in a weight ratio of 80/10/10 was dissolved in cyclopentanone, and a composition in which the concentration of the compounds was 20% by weight was prepared. A fluorine-based nonionic surfactant FTX-218 in a weight ratio of 0.002 and a polymerization initiator DTS-102 (Midori Kagaku Co., Ltd.) in a weight ratio of 0.02 were added to the composition. The thin film formed from the resultant solution according to the method described in Example 12 exhibited optical properties of an A-plate.

Example 16

A mixture of the compound (1-3-21)/the compound (M1-19-1)/the compound (M2-13-1) in a weight ratio of 35/30/35 was dissolved in a mixed solvent of PGMEA/MMP=9/1 by volume, and a composition in which the concentration of the compounds was 20% by weight was prepared. A polymerization initiator CPI-110P in a weight ratio of 0.02 was added to the composition. The resultant solution was applied to a glass substrate with a spin-coater, giving a thin film. The glass substrate was placed on a hot plate at 70° C. for 120 seconds, evaporating the solvent and forming a paint film. Then, the paint film was polymerized in air at room temperature for 30 seconds, with irradiance of 30 mW/cm$^2$ (a central wavelength at 365 nm) using a 250 W-ultra high-pressure mercury lamp. The formed thin film was fixed in a homogeneous orientation and exhibited optical properties of a C-plate.

Example 17

A mixture of the compound (1-1-20)/the compound (1-3-21)/the compound (M1-1-1)/the compound (6-8-1) in a weight ratio of 60/15/15/10 was dissolved in a mixed solvent of PGMEA/cyclopentanone=3/7 by volume, and a composition in which the concentration of the compounds was 20% by weight was prepared. A fluorine-based nonionic surfactant FTX-218 in a weight ratio of 0.002 and a polymerization initiator CPI-110P in a weight ratio of 0.02 were added to the composition. The thin film formed from the resultant solution according to the method described in Example 12 exhibited optical properties of a negative C-plate.

Example 18

A mixture of the compound (1-1-20)/the compound (M1-19-1)/the compound (M1-1-2) in a weight ratio of 30/40/30 was dissolved in methyl ethyl ketone, and a composition in which the concentration of the compounds was 20% by weight was prepared. A fluorine-based nonionic surfactant FTX-218 in a weight ratio of 0.002 and a polymerization initiator CPI-110P in a weight ratio of 0.02 were added to the composition. The thin film formed from the resultant solution according to the method described in Example 12 exhibited optical properties of selective reflection of visible light.

Example 19

A mixture of the compound (1-4-24)/the compound (M1-1-1)/the compound (M2-13-1) in a weight ratio of 10/75/15 was dissolved in toluene, and a composition in which the concentration of the compounds was 20% by weight was prepared. A polymerization initiator DTS-102 in a weight ratio of 0.02 was added to the composition. The thin film formed from the resultant solution according to the method described in Example 12 exhibited optical properties of an O-plate.

Example 20

A mixture of the compound (1-1-46)/the compound (1-1-3)/the compound (M1-7-3)/the compound (6-8-1) in a weight ratio of 40/20/30/10 was dissolved in a mixed solvent of PGMEA/cyclopentanone=3/7 by volume, and a composition in which concentration of the compounds 20% by weight was prepared. A polymerization initiator Irgacure 250 in a weight ratio of 0.02, a polymerization initiator Irgacure 184 in a weight ratio of 0.02 and a photosensitizer Z-4 in a weight ratio of 0.01 were added to the composition. The thin film formed from the resultant solution according to the method described in Example 12 exhibited optical properties of a negative C plate.

Applicability In Industry

The compound of the invention can be used as a polymerizable liquid crystal compound and can be used for a component of the polymerizable liquid crystal composition. The polymer of the invention can be utilized, for example, for an element of a liquid crystal display device, such as an optical retardation plate, a polarizer, a selective reflection film, a brightness enhancement film and a viewing angle-compensation film.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

What is claimed is:

1. A polymerizable liquid crystal compound represented by formula (1):

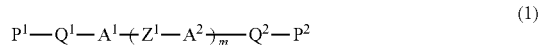
(1)

wherein
$A^1$ and $A^2$ are each independently 1,4-cyclohexylene, 1,4-phenylene, pyridine-2,5-diyl, pyrimidine-2,5-diyl, naphthalene-2,6-diyl, tetrahydronaphthalene-2,6-diyl, 1,3-dioxane-2,5-diyl or fluorene-2,7-diyl, and in the 1,4-phenylene and fluorene-2,7-diyl, arbitrary hydrogen may be replaced by fluorine, chlorine, cyano, methyl, ethyl, methoxy, hydroxy, formyl, acetoxy, acetyl, trifluoroacetyl, difluoromethyl or trifluoromethyl;

$Z^1$ is a single bond, —O—, —COO—, —OCO—CH=CH—COO—, —OCO—CH=CH—, —OCO—CH$_2$CH$_2$—, —CH$_2$CH$_2$—COO—, C≡C—COO—, —OCO—C≡C—, —CH$_2$O—, —OCH$_2$—, —CF$_2$—, —OCF$_2$—, —CONH—, —NHCO—, —(CH$_2$)$_4$—, —CH$_2$CH$_2$—, —CF$_2$CF$_2$—, —CH=CH—, —CF=CF— or —C≡C—;

m is an integer from 1 to 5, where arbitrary two of $A^2$ may be the same rings or different rings and arbitrary two of $Z^1$ may be the same bonding groups or different bonding groups, when m is 2 or more;

$P^1$ is a polymerizable group represented by formula (2-1);

$Q^1$ is —CH$_2$O—, —CH$_2$O(CH$_2$)$_n$O—, —COO— or —COO(CH$_2$)$_n$O—, wherein n is an integer from 1 to 17;

$P^2$ is a polymerizable group represented by any one of formula (2-1) to formula (2-4), hydrogen, fluorine, chlorine, cyano, trifluoromethyl, trifluoromethoxy, alkyl having 1 to 20 carbons or alkoxy having 1 to 20 carbons;

$Q^2$ is alkylene having 1 to 20 carbons, and in the alkylene arbitrary hydrogen may be replaced by fluorine and arbitrary —CH$_2$— may be replaced by —O—, —COO—, —OCO—, —CH=CH— or —C≡C— when $P^2$ is a polymerizable group, and $Q^2$ is a single bond when $P^2$ is not a polymerizable group:

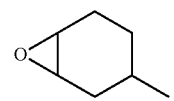
(2-1)

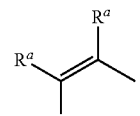
(2-2)

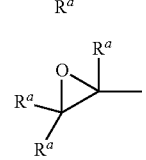
(2-3)

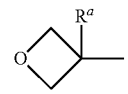
(2-4)

wherein $R^a$ is independently hydrogen, halogen or alkyl having 1 to 5 carbons.

2. The polymerizable liquid crystal compound according to claim 1, wherein $A^1$ and $A^2$ are each independently 1,4-cyclohexylene, 1,4-phenylene, naphthalene-2,6-diyl or fluorene-2,7-diyl, and in the 1,4-phenylene and fluorene-2,7-diyl, arbitrary one or two hydrogens may be replaced by fluorine, methyl or trifluoromethyl.

3. The polymerizable liquid crystal compound according to claim 1, wherein $A^1$ and $A^2$ are each independently 1,4-cyclohexylene, 1,4-phenylene, naphthalene-2,6-diyl or fluorene-2,7-diyl, and in the 1,4-phenylene and fluorene-2,7-diyl, arbitrary hydrogen may be replaced by fluorine, methyl or trifluoromethyl; $Z^1$ is a single bond, —COO—, —OCO—, —CH=CH—COO—, —CH$_2$CH$_2$—COO—, —OCO—CH=CH—, —OCO—CH$_2$CH$_2$—, —CH$_2$CH$_2$—or —C≡C—; m is an integer from 1 to 3; $P^2$ is a polymerizable group represented by any one of formula (2-1) to formula (2-4); $Q^1$ is —$CH_2O$—, —$CH_2O(CH_2)_nO$—, —COO— or —$COO(CH_2)_nO$—, wherein n is an integer from 1 to 11; $Q^2$ is alkylene having 1 to 14 carbons in which arbitrary —$CH_2$— may be replaced by —O— and arbitrary hydrogen may be replaced by fluorine when $P^2$ is a polymerizable group represented by formula (2-2) and $Q^2$ is —COO—, —OCO— or alkylene having 2 to 14 carbons, and in the alkylene arbitrary hydrogen may be replaced by fluorine and arbitrary —$CH_2$— may be replaced by —O—, —COO—, —OCO—, —CH=CH— or —C≡C— when $P^2$ is a polymerizable group represented by formula (2-1), formula (2-3) or formula (2-4); and $R^a$ in formula (2-2) to formula (2-4) is independently hydrogen, methyl or ethyl.

4. The polymerizable liquid crystal compound according to claim 1, wherein $A^1$ and $A^2$ are each independently 1,4-cyclohexylene or 1,4-phenylene, and in the 1,4-phenylene arbitrary one or two hydrogens may be replaced by fluorine or methyl; $Z^1$ is a single bond, —COO— or —OCO—; m is 1 or 2; $P^2$ is a polymerizable group represented by any one of formula (2-1) to formula (2-4); $Q^1$ is —$CH_2O$— —$CH_2O(CH_2)_nO$—, —COO— or —$COO(CH_2)_nO$—, wherein n is an integer from 1 to 11; $Q^2$ is alkylene having 1 to 14 carbons in which arbitrary —$CH_2$— may be replaced by —O— when $P^2$ is a polymerizable group represented by formula (2-2) and $Q^2$ is a group defined in —COO—, —OCO— or alkylene having 2 to 14 carbons, and in the alkylene arbitrary —$CH_2$— may be replaced by —O—, —COO— or —OCO— when $P^2$ is a polymerizable group represented by formula (2-1), formula (2-3) or formula (2-4); and $R^a$ in formula (2-2) to formula (2-4) is independently hydrogen, methyl or ethyl.

5. The polymerizable liquid crystal compound according to claim 1, wherein $A^1$ and $A^2$ are each independently 1,4-cyclohexylene or 1,4-phenylene, and in the 1,4-phenylene arbitrary one or two hydrogens may be replaced by fluorine or methyl; $Z^1$ is a single bond, —COO— or —OCO—; m is 1 or 2; $P^2$ is a polymerizable group represented by formula (2-1); $Q^1$ is —$CH_2O(CH_2)_nO$—, —COO— or —$COO(CH_2)_nO$—, wherein n is an integer from 1 to 11; $Q^2$ is —$OCH_2$—, —$O(CH_2)_nOCH_2$—, —OCO— or —$COO(CH_2)_n$—OCO—, wherein n is an integer from 1 to 11.

6. The polymerizable liquid crystal compound according to claim 1, wherein $A^1$ and $A^2$ are each independently 1,4-cyclohexylene or 1,4-phenylene, and in the 1,4-phenylene arbitrary one or two hydrogens may be replaced by fluorine or methyl; $Z^1$ is a single bond, —COO— or —OCO—; m is 1 or 2; $P^2$ is a polymerizable group represented by formula (2-2); $Q^{n1}$ is —$CH_2O$—, —$CH_2O(CH_2)_nO$—, —COO— or —$COO(CH_2)_nO$—, wherein n is an integer from 1 to 11; $Q^2$ is alkylene having 1 to 14 carbons in which arbitrary —$CH_2$— may be replaced by —O—; and $R^a$ in formula (2-2) is hydrogen.

7. The polymerizable liquid crystal compound according to claim 1, wherein $A^1$ and $A^2$ are each independently 1,4-cyclohexylene or 1,4-phenylene, and in the 1,4-phenylene arbitrary one or two hydrogens may be replaced by fluorine or methyl; $Z^1$ is a single bond, —COO— or —OCO—; m is 1 or 2; $P^2$ is a polymerizable group represented by formula (2-3); $Q^1$ is —$CH_2O$—, —$CH_2O(CH_2)_nO$—, —COO— or —COO$(CH_2)_nO$—, wherein n is an integer from 1 to 11; $Q^2$ is —$OCH_2$—, —$O(CH_2)_nOCH_2$—, —OCO— or —$O(CH_2)_n$—OCO—, wherein n is an integer from 1 to 11; and $R^a$ in formula (2-3) is hydrogen.

8. The polymerizable liquid crystal compound according to claim 1, where $A^1$ and $A^2$ are each independently 1,4-cyclohexylene or 1,4-phenylene, and in the 1,4-phenylene arbitrary one or two hydrogens may be replaced by fluorine or methyl; $Z^1$ is a single bond, —COO— or —OCO—; m is 1 or 2; $P^2$ is a polymerizable group represented by formula (2-4); $Q^1$ is —$CH_2O$—, —$CH_2O(CH_2)_nO$—, —COO— or —COO$(CH_2)_nO$—, wherein n is an integer from 1 to 11; $Q^2$ is —$OCH_2$—, —$O(CH_2)_nO$—, —OCO— or —$O(CH_2)_n$OCO—, wherein n is an integer from 1 to 11; and $R^a$ in formula (2-4) is methyl or ethyl.

9. A film having optical anisotropy, comprising a polymer formed by polymerization of at least one of compounds according to claim 1.

10. The film having optical anisotropy according to claim 9, wherein the film has optical properties of an A-plate.

11. The film having optical anisotropy according to claim 9, wherein the film has optical properties of a C-plate.

12. The film having optical anisotropy according to claim 9, wherein the film has optical properties of a negative C-plate.

13. The film having optical anisotropy according to claim 9, wherein the film has optical properties of an O-plate.

14. A liquid crystal display device containing the film having optical anisotropy according to claim 9.

* * * * *